US012655209B2

(12) United States Patent
Ling et al.

(10) Patent No.: US 12,655,209 B2
(45) **Date of Patent: \*Jun. 16, 2026**

(54) FcRn ANTIBODIES AND METHODS OF USE THEREOF

(71) Applicant: Momenta Pharmaceuticals, Inc., Titusville, NJ (US)

(72) Inventors: Leona E. Ling, Spring House, PA (US); Sucharita Roy, Acton, MA (US); Nathaniel Washburn, Littleton, MA (US); Marilyn Kehry, San Diego, CA (US); David J. King, Encinitas, CA (US); Anthony Manning, Cambridge, MA (US); James Meador, III, Framingham, MA (US); Jan Hillson, Cambridge, MA (US)

(73) Assignee: Momenta Pharmaceuticals, Inc., Titusville, NJ (US)

( \* ) Notice: Subject to any disclaimer, the term of this patent is extended or adjusted under 35 U.S.C. 154(b) by 848 days.

This patent is subject to a terminal disclaimer.

(21) Appl. No.: 17/661,070

(22) Filed: Apr. 28, 2022

(65) Prior Publication Data

US 2023/0049725 A1 Feb. 16, 2023

Related U.S. Application Data

(63) Continuation of application No. 16/321,801, filed as application No. PCT/US2017/044765 on Jul. 31, 2017, now Pat. No. 11,345,751.

(60) Provisional application No. 62/368,803, filed on Jul. 29, 2016, provisional application No. 62/368,770, filed on Jul. 29, 2016.

(51) Int. Cl.
*C07K 16/28* (2006.01)
*A61P 37/02* (2006.01)

(52) U.S. Cl.
CPC .............. *C07K 16/28* (2013.01); *A61P 37/02* (2018.01); *C07K 2317/565* (2013.01)

(58) Field of Classification Search
CPC .................................................. A61K 39/3955
See application file for complete search history.

(56) References Cited

U.S. PATENT DOCUMENTS

| | | |
|---|---|---|
| 1,345,751 A | 7/1920 | Dewrance |
| 7,662,928 B2 | 2/2010 | Balthasar et al. |
| 9,943,642 B2 | 4/2018 | Kondo |
| 10,676,526 B2 | 6/2020 | Kehry et al. |
| 11,345,751 B2 \* | 5/2022 | Ling .......................... A61P 9/00 |
| 11,354,751 B2 | 6/2022 | Hurry |
| 11,732,047 B2 | 8/2023 | Kehry et al. |
| 11,773,168 B2 | 10/2023 | Ling et al. |
| 2005/0053598 A1 | 3/2005 | Burke et al. |
| 2009/0131639 A1 | 5/2009 | Kakuta et al. |

| | | |
|---|---|---|
| 2009/0297535 A1 | 12/2009 | Kolkman et al. |
| 2010/0330076 A1 | 12/2010 | Georgiou et al. |
| 2011/0027262 A1 | 2/2011 | Das et al. |
| 2011/0059101 A9 | 3/2011 | Kolkman et al. |
| 2012/0183549 A1 | 7/2012 | Bradley et al. |
| 2013/0111507 A1 | 5/2013 | Naka et al. |
| 2014/0235482 A1 | 8/2014 | George et al. |
| 2014/0308206 A1 | 10/2014 | Sexton et al. |
| 2015/0118240 A1 | 4/2015 | Finney et al. |
| 2015/0157709 A1 | 6/2015 | Everett et al. |
| 2015/0291689 A1 | 10/2015 | Padley et al. |
| 2015/0329628 A1 | 11/2015 | Antochshuk et al. |
| 2016/0194397 A1 | 7/2016 | TenHoor et al. |
| 2017/0209550 A1 | 7/2017 | Kjellman et al. |
| 2018/0016334 A1 | 1/2018 | Kehry et al. |
| 2019/0194277 A1 | 6/2019 | de Haard et al. |
| 2020/0003191 A1 | 1/2020 | Kraft et al. |
| 2020/0031917 A1 | 1/2020 | Kraft et al. |
| 2020/0044731 A1 | 2/2020 | Tsuzaki et al. |
| 2020/0299382 A1 | 9/2020 | Kehry et al. |
| 2021/0299255 A1 | 9/2021 | Zhang et al. |
| 2021/0340251 A1 | 11/2021 | Zhang et al. |

(Continued)

FOREIGN PATENT DOCUMENTS

| | | |
|---|---|---|
| CN | 101124245 A | 2/2008 |
| CN | 101421297 A | 4/2009 |

(Continued)

OTHER PUBLICATIONS

Anonymous Clinicaltrials: "A Study to Evaluate the Safety, Tolerability, Efficacy, Pharmacokinetics and Pharmacodynamics of M281 Administered to Adults With Generalized Myasthenia Gravis", NCT03772587, Version 16, Jun. 27, 2023, pp. 1-16.

Anonymous: "An Extension Study of MOM-M281-004 to Evaluate the Safety, Tolerability, and Efficacy of M281 Administered to Patients With Generalized Myasthenia Gravis", NCT03896295, Version 13, Jun. 27, 2023, pp. 1-14.

Guptill et al., "A Phase 2, multicenter, randomized, double-blind, placebo-controlled study to evaluate the safety, tolerability, efficacy, pharmacokinetics and pharmacodynamics of nipocalimab (M281) in adults with GE", Muscle & nerve, 2020, vol. 62, (SUPPL 1), 2020, S88.

(Continued)

*Primary Examiner* — Prema M Mertz

(74) *Attorney, Agent, or Firm* — BakerHostetler

(57) ABSTRACT

The present application features antibodies that bind to human neonatal Fc receptor (FcRn). These anti-FcRn antibodies are useful, e.g., to promote clearance of autoantibodies in a subject, to suppress antigen presentation in a subject, to block an immune response, e.g., block an immune complex-based activation of the immune response in a subject, and to treat immunological diseases (e.g., autoimmune diseases) in a subject. These anti-FcRn antibodies are also useful, e.g., to decrease pathogenic antibody transport across the placenta of a pregnant subject, to increase pathogenic antibody catabolism in a pregnant subject, and to treat an antibody-mediated enhancement of viral disease in a fetus or a neonate.

14 Claims, 32 Drawing Sheets

Specification includes a Sequence Listing.

(56) References Cited

U.S. PATENT DOCUMENTS

| | | |
|---|---|---|
| 2022/0064290 A1 | 3/2022 | Ling et al. |
| 2022/0144946 A1 | 5/2022 | Ramchandran et al. |
| 2022/0259308 A1 | 8/2022 | Arroyo et al. |
| 2024/0158508 A1 | 5/2024 | Kehry et al. |

FOREIGN PATENT DOCUMENTS

| | | |
|---|---|---|
| CN | 102149729 A | 8/2011 |
| CN | 103619353 A | 3/2014 |
| CN | 103717619 A | 4/2014 |
| CN | 104479017 A | 4/2015 |
| CN | 106103476 A | 11/2016 |
| CN | 109790221 A | 5/2019 |
| CN | 107567460 B | 4/2021 |
| EP | 2703010 A2 | 3/2014 |
| EP | 3010938 A1 | 4/2016 |
| EP | 3250610 A2 | 12/2017 |
| EP | 3491025 B1 | 6/2019 |
| JP | 06-217791 A | 8/1994 |
| JP | 2011-088913 A | 5/2011 |
| JP | 2011523351 A | 8/2011 |
| JP | 2014523737 A | 9/2014 |
| JP | 2015163618 A | 9/2015 |
| JP | 5853178 B2 | 2/2016 |
| JP | 2017516848 A | 6/2017 |
| JP | 6853178 B2 | 3/2021 |
| JP | 7094941 B2 | 7/2022 |
| KR | 20140036267 A | 3/2014 |
| KR | 10-2017-0109020 A | 9/2017 |
| WO | 93/19785 A1 | 10/1993 |
| WO | 2004041862 A2 | 5/2004 |
| WO | 2005013912 A2 | 2/2005 |
| WO | 2007087289 A3 | 10/2008 |
| WO | 2009124294 A2 | 10/2009 |
| WO | 2009131702 A9 | 9/2010 |
| WO | 2012167039 A1 | 12/2012 |
| WO | 2014019727 A1 | 2/2014 |
| WO | 2014204280 A1 | 12/2014 |
| WO | 2014179601 A3 | 1/2015 |
| WO | 2015100299 A1 | 7/2015 |
| WO | 2015167293 A1 | 11/2015 |
| WO | 2016065323 A2 | 4/2016 |
| WO | 2016123521 A3 | 9/2016 |
| WO | 2016183352 A1 | 11/2016 |
| WO | 2017015622 A2 | 1/2017 |
| WO | 2017/189556 A1 | 11/2017 |
| WO | 2018023136 A1 | 2/2018 |
| WO | 2018/055574 A1 | 3/2018 |
| WO | 2019/070714 A1 | 4/2019 |
| WO | 2019110823 A1 | 6/2019 |
| WO | 2019118791 A1 | 6/2019 |
| WO | 2019160979 A1 | 8/2019 |
| WO | 2019/194277 A1 | 10/2019 |
| WO | 2020018910 A1 | 1/2020 |
| WO | 2020023310 A1 | 1/2020 |
| WO | 2020/047029 A1 | 3/2020 |
| WO | 2020079086 A1 | 4/2020 |
| WO | 2020097099 A1 | 5/2020 |
| WO | 2021022249 A1 | 2/2021 |
| WO | 2021140202 A1 | 7/2021 |
| WO | 2021257668 A1 | 12/2021 |
| WO | 2022098955 A1 | 5/2022 |
| WO | 2022221239 A1 | 10/2022 |
| WO | 2022/240875 A1 | 11/2022 |

OTHER PUBLICATIONS

Casipit et al., "Improving the Binding Affinity of an Antibody using Molecular Modeling and Site-Directed Mutagenesis," Protein Science, Aug. 1, 1998, 7:1671-1680.

Chen et al., "Enhancement and destruction of antibody function by somatic mutation: unequal occurrence is controlled by V gene combinatorial associations", The EMBO Journal (1995) vol. 14 No. 12, pp. 2784-2794.

Chien et al., "Significant structural and functional change of an antigen-binding site by a distant amino acid substitution: Proposal of a structural mechanism,", Proc. Natl. Acad. Sci. USA, 1989, 86(14): 5532-5536.

Christensen, D et al., Trehalose preserves DDA/TDB liposomes and their adjuvant effect during freeze-drying, Biochimica et Biophysica Acta., Sep. 2007, Epub May 13, 2007, vol. 1768, No. 9, pp. 2120-2129.

Christianson et al., "Monoclonal antibodies directed against human FcRn and their applications," MAbs, 2012, 4 (2):208-216.

Committee on Obstetric Practice American Institute of Ultrasound in Medicine Society for Maternal-Fetal Medicine, "Committee Opinion. No. 700: Methods for Estimating the Due Date," Obstetrics & Gynecology, May 2017, 129(5): e150-e154.

Daugherty et al., "Formulation and Delivery Issues for Monoclonal Antibody Therapeutics", Current Trends In Monoclonal Antibody Development and Manufacturing (2010) pp. 103-129.

Ellinger et al., "Overexpression of the human neonatal Fc-receptor alpha-chain in trophoblast-derived BeWo cells Increases cellular retention of beta2-microglobulin," Placenta., 2005, 26(2-3): 171-182.

Extended European Search Report Application No. EP19840429. mailed Mar. 18, 2022.

Hiroyuki et al., "Tryptophan H33 plays an important role in pyrimidine (6-4) pyrimidone photoproduct binding by a higli-affinity antibody," Protein Engineering, 1999, 12(10): 879-884.

Hoftman et al., "Newborn illnesses caused by transplacental antibodies," Adv. Pediatr., 2008, 55: 271-304.

Hutson et al., "The human placental perfusion model: a systematic review and development of a model to predict in vivo transfer of theraeputic drugs," Clin. Pharmacol. Ther., 2011, 90(1): 67-76.

International Preliminary Report on Patentability in International Application No. PCT/US2017/044765, dated Jan. 29, 2019, 9 pages.

International Preliminary Report on Patentability in International Application No. PCT/US2018/065568, dated Jun. 16, 2020, 10 pages.

International Preliminary Report on Patentability in International Applications No. PCT/US2016/015720, dated Aug. 1, 2017.

International Search Report and Written Opinion in International Application No. PCT/US16/15720, dated Jul. 26, 2016.

International Search Report and Written Opinion in International Application No. PCT/US2017/44765, dated Jan. 9, 2018, 14 pages.

International Search Report and Written Opinion in International Application No. PCT/US2019/042597, dated Nov. 26, 2019.

International Search Report and Written Opinion in International Application No. PCT/US2019/042615, dated Nov. 15, 2019.

International Search Report and Written Opinion in International Application No. PCT/US2020/044731, dated Dec. 22, 2020.

International Search Report and Written Opinion in International Application No. PCT/US2021/058188, dated Apr. 5, 2022.

International Search Report and Witten Opinion in International Application No. PCT/US2018/065568, dated Apr. 2, 2019, 14 pages.

Junghans and Anderson, "The protection receptor for IgG catabolismis the beta2-microglobulin-containing neonatal Intestinal transport receptor," PNAS, May 1996, 93:5512-5516.

Kobrin et al., "A V Region Mutation in Phosphocholine-Binding Monoclonal Antibody Results in Loss of Antigen Binding,", J. of Immunol., Mar. 15, 1991, 146(6): 2017-2020.

Kussie et al., "A Single Engineered Amino Acid Substitution Changes Antibody Fine Specificity", Journal of Immunology (1994) 152(1): pp. 146-152.

Li et al., "The Maternal Immune Response to Fetal Platelet GPibalpha Causes Frequent Miscarriage in Mice That Can Be Prevented by Intravenous IgG and anti-FcRn Therapies," J. Clin. Invest., Nov. 2011, 121(11): 4537-4547.

Ling et al., "32: M281, an anti-FcRn antibody, inhibits IgG transfer in a human ex-vivo placental perfusion model," Jan. 2019, 220(1): 32.

(56) References Cited

OTHER PUBLICATIONS

Ling et al., "M281: A Therapeutic Anti-FcRn Blocking Antibody for Rapid Clearance of IgG and IgG Autoantibodies in Immune Cytopenias and Other Auto/Allm-Immune Disease", Blood (2015) 126, 23: 3472.

Liu et al., "Amelioration of Experimental Autoimmune Myasthenia Gravis in Rats by Neonatal FcR Blockage," J. of Immunol., Apr. 15, 2007, 178(8): 5390-5398.

Mahadevan eta l., "Placental transfer of anti-tumor necrosis factor agents in pregnant patients with inflammatory bowel disease," Clin. Gastroenterol. Hepatol., 2013, 11(3): 286-292.

Maleck, "Ex vivo human placenta models: transport of immunoglobulin G and its subclasses," Vaccine, 2003, 21: 3362-3364.

Mathiesen eta l., "Quality assessment of a placental perfusion protocol," Reproductive Toxicology, 2010, 30: 138-146.

Montes, T et al., Genetic Modification of the Penicillin G Acylase Surface to Improve its Reversible Immobilization on Ionic Exchangers, Applied and Environmental Microbiology, Jan. 2007, Epub Nov. 10, 2006, vol. 73, No. 1, pp. 312-319.

Morgan et al., "The effect of intravenous immunoglobulin on placental transfer of a platelet-specific antibody: Anti-P1A1," Transfusion Medicine, 1991, 1: 209-216.

Mørck et al., "Placental transport and in vitro effects of Bisphenol A," Reproductive Toxicol., 2010, 30: 131-137.

Nanovskaya et al., "Transplacental Transfer and Metabolism of Buprenophine," J. Pharmacol. Exp. Ther., 2002, 300 (1): 26-33.

Nonfinal Office Action mailed Jan. 21, 2022 received in U.S. Appl. No. 16/771,147.

Nonfinal Office Action mailed Jan. 22, 2022 received in U.S. Appl. No. 16/771,147.

Nonfinal Office Action mailed Jun. 29, 2021 received in U.S. Appl. No. 16/321,801.

Notice of Allowance mailed Jan. 28, 2022 received in U.S. Appl. No. 16/321,801.

Panka et al., "Defining the Structural Correlates Responsible for Loss of Arsonate Affinity in an IDCR Antibody Isolated From an Autoimmune Mouse," Mol. Immunol.,I Aug. 1, 1993, 30(11): 1013-1020.

Porter et al., "Certolizumab pegol does not bind the neonatal Fc receptor (FcRn): Consequences for FcRn-mediated in vitro transcytosis and ex vivo human placental transfer," J. Repro. Imm., 2016, 116: 7-12.

Roopenian et al., "Clinical Ramifications of the MHC Family Fc Receptor FcRn," J. Clin. Immunol., 2010, 30(6): 790-797.

Roopenian et al., "FcRn: the neonatal Fc receptor comes of age," Nature Immunol., 2007, 7: 715-25.

Rudikoff et al., "Single Amino Acid Substitution Altering Antigen-Binding Specificity," Proc. Natl. Acad. Sci. USA, Mar. 1, 1982, 79: 1979-1983.

Schildbach et al., "Modulation of antibody affinity by a non-contact residue," Protein Science, 1993, 2: 206-214.

Schneider et al., "Effect of flow rate ratio on the diffusion of antipyrine and 3H20 in the isolated dually in vitro perfused lobe of the human placenta," Contrib. Gynecol. Obstet., 1985, 13: 114-123.

Schneider et al., "Transfer across the perfused human placenta of antipyrine, sodium and leucine," Am. J. Obstet. Gynecol., 1972, 114: 822-828.

Sharma et al., "The Formulation and Delivery of Monoclonal Antibodies", Therapeutic Monoclonal Antibodies: From Bench to Clinic (2009) pp. 1-37.

Singapore Search Report and Written Opinion in Application No. 10202007232W, dated Feb. 17, 2022.

Gaudinski et al., "Safety and pharmacokinetics of the Fc-modified HIV-1 human monoclonal antibody VRC01LS: A Phase 1 open-label clinical trial in healthy adults", PLOS Medicine, vol. 15, No. 1, Jan. 24, 2018, pp. 1-20.

Tosi et al. Clinical Development Strategies and Outcomes in First-in-Human Trials of Monoclonal Antibodies. J Clin Oncol. Jul. 1, 2015; 33(19):2158-65.

International Search Report and Witten Opinion in International Application No. PCT/US2022/024354, dated Sep. 12, 2022.

Edelman et al., "The Covalent Structure Of An Entire Gimmunoglobulin Molecule," Proc. Natl. Acad. USA (1969) 63, pp. 78-85.

Extended European Search Report for European Patent Application No. 23189767.9 dated Jan. 17, 2024.

Extended European Search Report for European Patent Application No. 23195791.1 dated Jan. 17, 2024.

Haberger et al., "Rapid characterization of biotherapeutic proteins by size-exclusion chromatography coupled to native mass spectrometry," MABS (2016) vol. 8(2), pp. 331-339.

International Preliminary Report on Patentability for International PCT Application No. PCT/US2019/042615 dated Feb. 4, 2021.

Ling et al., "Targeting the Neonatal Fc Receptor (FcRn) to Mediate Autoantibody Clearance in IgG-Driven Autoimmune Disease," Momenta Pharmaceuticals, Inc., Abstract THU0057, Presented at the Annual European Congress of Rheumatology, Jun. 10-13, 2015.

Kortt et al., "Dimaric and trimeric antibodies: high avidity scFvs for cancer targeting", Biomolecular Engineering (2001) 18; 95-108.

Nonfinal Office Action mailed Aug. 5, 2022 received in U.S. Appl. No. 16/771,147.

Buyon et al., "Autoimmune associated congential heart block: integration of clinical and research clues in the management of the maternal/foetal dyad at risk", Journal of Internal Medicine (2009) 265: 653-662.

Nonfinal Office Action mailed Oct. 17, 2022 received in U.S. Appl. No. 17/519,811.

Ling, et al., "M281, and Anti-FcRn Antibody:Pharmacodynamics, Pharmacokinetics, and Safety Across the Full Range of IgG Reduction in a First-in-Human Study", Clinical Pharmacology & Therapeutics (2019) vol. 105 No. 4, pp. 1031-1039.

Lazaridis, et. al., "Autoantibody Specificities in Myasthenia Gravis; Implications for Improved Diagnostics and Therapeutics", Front. Immunol. (2020) 14; 11:212.

Roopenian, et. al., "Albumin-deficient mouse models for studying metabolism of of human albumin and pharmacokinetics of albumin-based drugs", mABS (2015) vol. 7, Issue 2, pp. 344-351.

Hui-Juan et. al., "Prokaryotic expression of porcine FcRn-CT and prepartion of polyclonal antibody", Chinese Journal of Vetenary Science (2012) vol. 32, No. 2, pp. 262-271.

Zdravic et al., "Fetal and neonatal alloimmune thrombocytopenia", Seminars in Fetal & neonatal Medicine (2016) 21; pp. 19-27.

Tannemaat et al., "Emerging therapies for autoimmune myasthenia gravis: Towards treatment without corticosteroids", Neuromuscular Disorders (2020 30: pp. 111-119.

Yu et al., "Estimation of Hemolytic Disease of the Newborn in the United States from 1996-2010", (2021).

Singapore Search Report and Written Opinion in Singapore Application No. 11201705475Q, dated Jul. 31, 2018.

Urbaniak et al., "Transfer of anti-D antibodies across the isolated perfused human placental lobule and inhibition by high dose intravenous immunoglobulin: a possible mechanism of action," Br. J. Hematol., 1997, 96: 186-93.

Urbaniak et al., "Variable inhibition of placental IgG transfer in vitro with commercial IVgG preparations," Br. J. Haematol., 1999, 107: 815-817.

Wang, et al., "Antibody Structure, Instability, and Formulation", Journal of Pharmaceutical Sciences, (2007) vol. 96, No. 1.

Warne et al., "Development of high concentration protein biopharmaceuticals: The use of platform approaches in formulation development", European Journal of Pharmaceutics and Biopharmaceutics (2011) 78: pp. 208-212.

Whittaker, MM et al., Burst Kinetics and Redox Transformations of the Active Site Manganese Ion in Oxalate Oxidase: Implications for the Catalytic Mechanism, The Journal of Biological Chemistry, Mar. 9, 2007, Epub Jan. 8, 2007, vol. 282, No. 10, pp. 7011-7023.

Whittamker, MM et al., Burst Kinetics and Redoc Transformations of the Active Site Manganesse Ion in Oxalate Oxidase: Implications for the Catalytic Mechanism, The Journal of Biological Chemistry, Mar. 9, 2007, Epub Jan. 8, 2007, vol. 282, No. 10, pp. 7011-7023.

(56)                    References Cited

OTHER PUBLICATIONS

Winkler et al., "Changing the Antigen Binding Specificity by Single Point Mutations of an Anti-p24 (HIV-1) Antibody," J. of Immunol., Oct. 15, 2000, 165(8): 4505-4514.

Zhu et al., "MHC class I-related neonatal Fc receptor for IgG is functionally expressed in monocytes, intestinal macrophages, and dendritic cells," J. Immunol., 2001, 166(5): 3266-3276.

Notice of Allowance mailed Nov. 22, 2022 received in U.S. Appl. No. 16/825,066.

Deng et al., "Neonatal Alloimmune Thrombocytopenia Associated with Maternal HLA Antibodies," Chinese Journal Of Blood Transfusion (Sep. 2016) vol. 29, No. 9, pp. 935-937.

European Search Report for European Patent Application No. 16744204.5 dated Jul. 24, 2018.

Ling, L.E., et al. "Targeting the Neonatal FC Receptor (FCRN) to Mediate Autoantibody Clearance in IgG-Driven Autoimmune Disease." Poster Presentations Rheumatoid arthritis—etiology, pathogenesis and animal models.

Wilcox et al., "Review of Transplacental Antibody Transfer," Frontiers in Immunology (Oct. 2017) vol. 8, Art. 1294, pp. 1-12.

Kang et al., "Rapid Formulation Development for Monoclonal Antibodies," BioProcess International (Apr. 2016) pp. 1-7.

European Search Report for European Patent Application No. 19838652.6 dated Nov. 10, 2022.

European Search Report for European Patent Application No. 20846154.1 dated Jul. 19, 2023.

International Preliminary Report on Patentability for International PCT Application No. PCT/US2019/042597 dated Feb. 4, 2021.

International Preliminary Report on Patentability for International PCT Application No. PCT/US2020/044731 dated Feb. 10, 2022.

International Preliminary Report on Patentability for International PCT Application No. PCT/US2021/058188 dated May 19, 2023.

European Search Repot for European Patent Application No. 17835436.1.

Akilesh et al., "The MHC class I-like Fc receptor promotes humorally mediated autoimmune disease," J Clin Invest (2004) 113(9): 1328-1333.

Chung et al., "Effects of Antibody Disulfide Bond Reduction on Purification Process Performance and Final Drug Substance Stability," Biotechnol. Bioeng. (Jun. 2017) vol. 114, No. 6, pp. 1264-1274.

Miniaci et al., "Loading Dose," StatPearls (2022) pp. 1-3.

Notice of Allowance for U.S. Appl. No. 16/771,147 dated May 19, 2023.

Qin, "Modern Surgery for Obstetric and Gynecological Diseases," Scientific Technical Documentation Press, 1st edition (2017) p. 172.

Vlasak et al., "Fragmentation of Monoclonal Antibodies," mAbs. (2011) 3(3) pp. 253-663.

International Preliminary Report on Patentability for International PCT Application No. PCT/US2022/024354 dated Oct. 26, 2023.

Restriction Requirement for U.S. Appl. No. 15/546,870 dated Jun. 6, 2019.

Restriction Requirement for U.S. Appl. No. 16/825,066 dated Aug. 4, 2022.

Nonfinal Office Action mailed Nov. 8, 2023 received in U.S. Appl. No. 17/519,811.

Final Office Action for U.S. Appl. No. 16/321,801 dated Dec. 3, 2021.

Final Office Action for U.S. Appl. No. 17/519,811 dated Apr. 26, 2023.

Notice of Allowance for U.S. Appl. No. 15/546,870 dated Apr. 3, 2020.

Notice of Allowance for U.S. Appl. No. 15/546,870 dated Mar. 17, 2020.

Notice of Allowance for U.S. Appl. No. 16/825,066 dated Apr. 12, 2023.

Liu, "Medical Immunology," China Press of Traditional Chinese Medicine, 1st edition (2008) p. 28.

Non-Final Office Action for U.S. Appl. No. 15/546,870 dated Oct. 18, 2019.

Vajdos et al., "Comprehensive Functional Maps of the Antigen-binding Site of an Anti-ErbB2 Antibody Obtained with Shotgun Scanning Mutagenesis," Journal of Molecular Biology (2002), vol. 320, pp. 415-428.

Brown et al., "Tolerance to Single, but Not Multiple, Amino Acid Replacements in Antibody VH CDR2," Journal of Immunology (1996), vol. 156, pp. 3285-3291.

Castleman et al., "Medical therapy to attenuate fetal anaemia in severe maternal red cell alloimmunisation", British Journal of Haematology, vol. 192, No. 3, Aug. 14, 2020, pp. 425-432.

Antozzi et al., "A Phase 2, Multicenter, Randomized, Double-Blind, Placebo-Controlled Study to Evaluate the Safety, Tolerability, Efficacy, Pharmacokinetics, Pharmacodynamics, and Immunogenicity of Nipocalimab Administered to Adults with Generalized Myasthenia Gravis," Poster Presented at the 16th International Congress on Neuromuscular Diseases (Virtual), May 21-22 & 28-29, 2021.

Choudhury, "Mode of Nipocalimab Action, PK-PD-Efficacy from Cells to Patients," FcRn-Targeted Therapies for Autoimmune Disorders Online Event, Mar. 23-25, 2021, pp. 1-23.

Danka et al., "Defining the Structural Correlates Responsible for Loss of Arsenate Affinity in an IDCR Antibody Isolated from an Autoimmune Mouse," Molecular Immunology, Aug. 1, 1993, vol. 30, No. 11, pp. 1013-1020.

Guptill et al., "Phase 2 Trial Evaluating the FcRn Antagonist Nipocalimab in Adults with Generalized Myasthenia Gravis," Momenta Pharmaceuticals, Inc., Presented at the 16th International Congress on Neuromuscular Diseases, Virtual Worldwide, May 21-22 & 28-29, 2021.

Guptill et al., "Vivacity-MG: A Phase 2, Multicenter, Randomized, Double-Blind, Placebo-Controlled Study to Evaluate the Safety, Tolerability, Efficacy, Pharmacokinetics, Pharmacodynamics, and Immunogenicity of Nipocalimab Administered to Adults with Generalized Myasthenia Gravis," Momenta Pharmaceuticals, Inc., 164, Presented at the American Association of Neuromuscular & Electrodiagnostic Medicine (AANEM) 2929 Virtual Annual Meeting, Oct. 7-10, 2020.

Guptill, "Vivacity-MG: A Phase 2, Multicenter, Randomized, Double-Blind, Placebo-Controlled Study to Evaluate the Safety, Tolerability, Efficacy, Pharmacokinetics, Pharmacodynamics, and Immunogenicity of Nipocalimab Administered to Adults with Generalized Myasthenia Gravis," American Academy of Neurology, Virtual Meeting, Apr. 17-22, 2021.

Junghans and Anderson, "The protection receptor for IgG catabolismis the ,32-microglobulin-containing neonatal intestinal transport receptor," PNAS, May 1996, 93:5512-5516.

Kósa et al., "High Risk of Depression, Anxiety, and an Unfavorable Complex Comorbidity Profile is Associated with SLE: A Nationwide Patient-Level Study," Arthritis Research & Therapy, 2022, vol. 24, Article 16.

Ling et al., "Nipocalimab's Selective Targeting of FcRn and IgG Clearance Preserves Key Immune Functions," American Academy of Neurology Annual Meeting, Apr. 24-26, 2022, pp. 1-12.

McCrae et al., "Identification of a Warm Autoimmune Hemolytic Anemia (wAIHA) Population Using Predictive Analytics of a Known Clinically Profiled Cohort," Momenta Pharmaceuticals, Inc., 2021, pp. 1-9.

McCrae et al., "Identification of a Warm Autoimmune Hemolytic Anemia (wAIHA) Population Using Predictive Analytics of a Known Clinically Profiled Cohort," Presented at the European Hematology Association (EHA), Virtual, Jun. 9-17, 2021, 1 page.

Minkler et al., "Changing the Antigen Binding Specificity by Single Point Mutations of an Anti-p24 (HIV-1) Antibody," Journal of Immunology, Oct. 15, 2000, vol. 165, No. 8, pp. 4505-4514.

Murakhovskaya et al., "Study Design of a Phase 2/3, Randomized, Double-Blind, Placebo-Controlled Study to Assess the Efficacy and Safety of Nipocalimab, an FcRn Antagonist, in Warm Autoimmune Haemolytic Anaemia (wAIHA)," Presented at the European Hematology Association (EHA), Virtual, Jun. 9-17, 2021.

Nhittamker et al., "Burst Kinetics and Redox Transformations of the Active Site Manganese Ion in Oxalate Oxidase: Implications for the Catalytic Mechanism," The Journal of Biological Chemistry, Mar. 9, 2007, Epub Jan. 8, 2007, vol. 282, No. 10, pp. 7011-7023.

(56)                    References Cited

OTHER PUBLICATIONS

Roy et al., "M281, an Anti-FcRn Antibody, Inhibits IgG Transfer in a Human Ex Vivo Placental Perfusion Model," American Journal of Obstetrics & Gynecology, May 2019, vol. 220, No. 5, pp. 498.e1-498.e9.

Vivacity-MG Phase 2 Interim Analysis Topline Results, Momenta Pharmaceuticals, Inc., 2020, pp. 1-22.

Zhang et al., "Real-World Resource Utilization and Productivity Loss Among Patients with Myasthenia Gravis in Sweden: A Nationwide Population-Based Study," Presented at the American Academy of Neurology, Apr. 24-26, 2022, pp. 1-13.

Zuercher et al., "Next-Generation Fc Receptor-Targeting Biologics for Autoimmune Diseases," Autoimmunity Reviews (2019) vol. 18, No. 10, Art. 102366, pp. 1-9.

Anonymous: "A Study of Nipocalimab in Children Aged 2 to Less Than 18 Years With Generalized Myasthenia Gravis", NCT05265273, Retrieved from https://clinicaltrials.gov/study/NCT05265273, Mar. 25, 2025, pp. 1-16.

Ling et al., "M281, an Anti-FcRn Antibody: Pharmacodynamics, Pharmacokinetics and Safety across the Full Range of IgG Reduction in a First-In-Human Study, Supplementary Materials", Apr. 1, 2019 (Apr. 1, 2019), XP093187207, DOI: https://doi.org/10.1002/cpt.1276, Retrieved from: URL:https://ascpt.onlinelibrary.wiley.com/action/downloadSupplement?doi=10.1002/cpt.1276&file=cpt1276-sup-0001-Supinfo.pdf.

Ling et al., "M281, an Anti-FcRn Antibody: Pharmacodynamics, Pharmacokinetics, and Safety Across the Full Range of IgG Reduction in a First-in-Human Study", Clinical Pharmacology & Therapeutics, vol. 105 No. 4, Apr. 2019, pp. 1031-1039.

Munot et al., "242nd ENMC International Workshop: Diagnosis and management of juvenile myasthenia gravis Hoofddorp, the Netherlands, Mar. 1-3, 2019", Neuromuscular Disorders, vol. 30, 2020, pp. 254-264.

O'Connell et al., "Management of Juvenile Myasthenia Gravis", Front. Neurol., vol. 11, Article 743, Jul. 2020, pp. 1-12.

Intravenous Immune Globulin (IVIG) Guideline, Intravenous Immune Globulin (IVIG) Administration in Neonates, ACTS Practice Committee, IVIG HDS Version May 10, 2007, 3pp.

RA | How to Prepare for RITUXAN® (rituximab) Infusions, Rituzan, accessed https://www. rituxan.com/ra/treatment/preparing.html, on Jan. 2, 2024, 1pp.

Simister et al., "Placental transport of immunoglobulin G, Vaccine", 21:3365-3369, 2003.

* cited by examiner

IgG Competition

Anti-FcRn mAbs compete effectively for IgG (Fc) binding to FcRn at pH 6.0

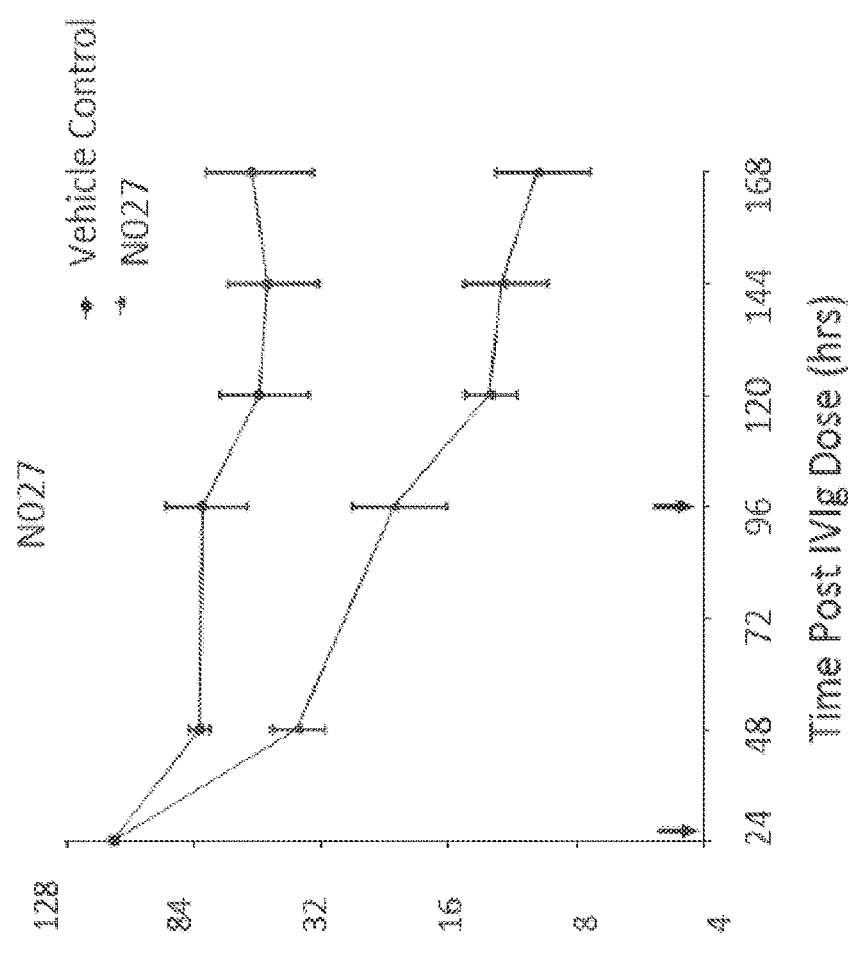
FIG. 2  Human IgG Catabolism

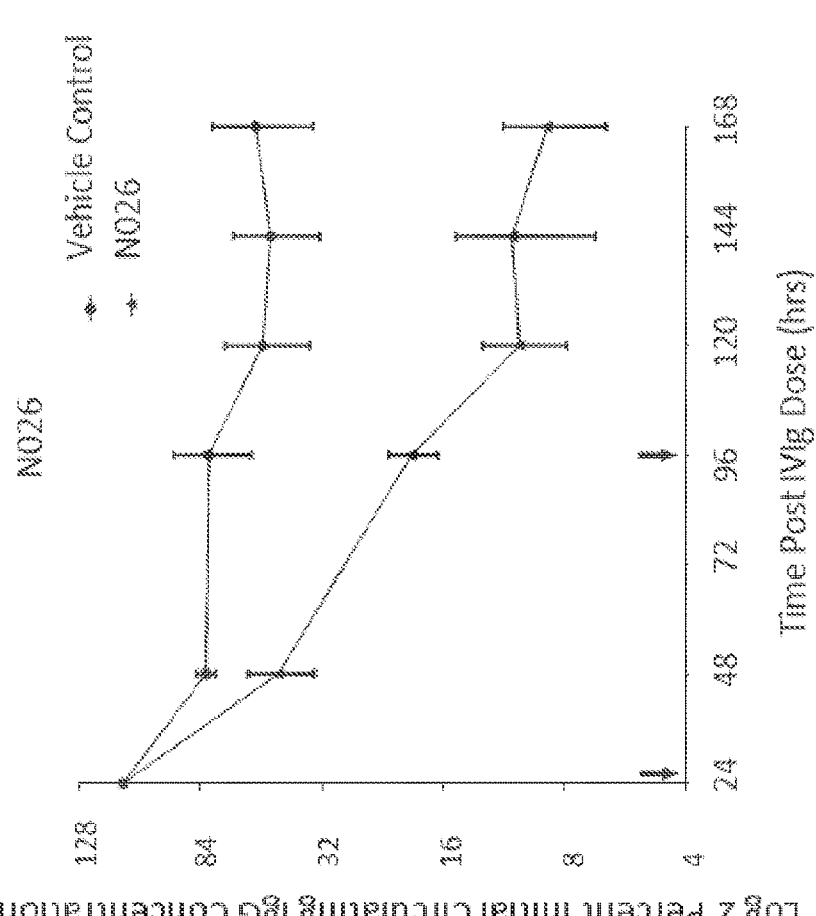
FIG. 2 cont.  Human IgG Catabolism

FIG. 2 cont. Human IgG Catabolism
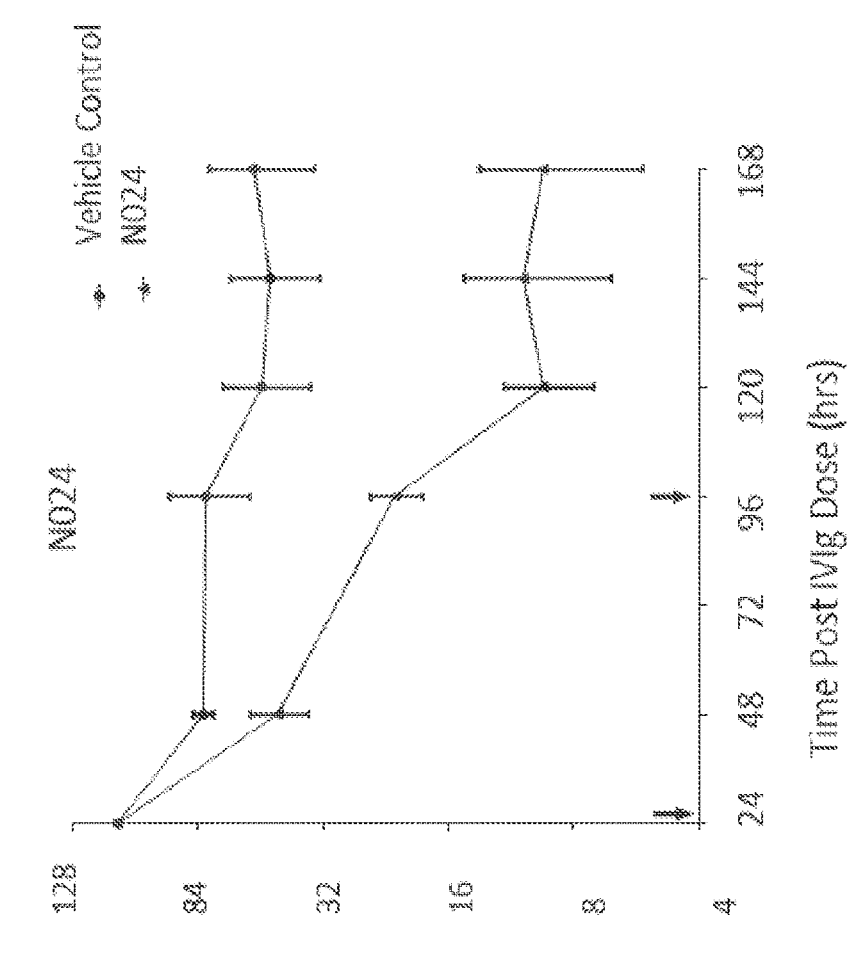

Endothelial cells

No treatment
NO27

$t_{1/2}$ of D2O-FcRn − NO27 = 7.513 hours
$t_{1/2}$ of D2O-FcRn + NO27 = 6.749 hours Labeled fraction from T=0 Remaining Time (hours)

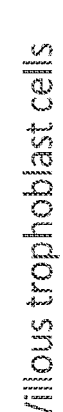
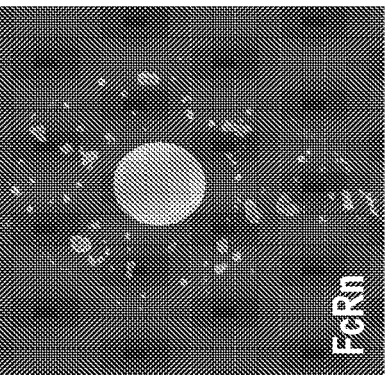
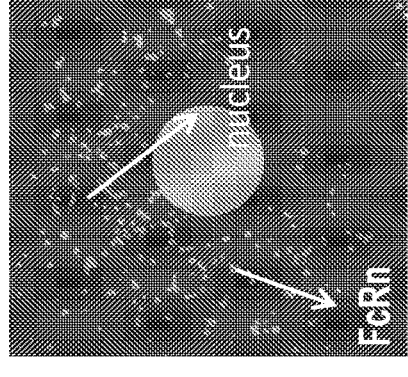
FIGS. 12A–12B

>FcRn-6xHis chain A (SEQ ID NO: 30)

AESHLSLLYHLTAVSSRAPRGTPAFWVSGWLGPQQYLSYNSLRGEAEPCGAWVWENQVSWY
WEKETWDIAKLIFIBASQRWQQDKAHKELTILLFSCPHRLREHLERGRGNLEWKEPP
SNRLKARpsspgs4VTCSHFSYTYPELQLRFLNWQLARGICGGDTGSWSDGSTHASSSL
TVPSSGHHHYCCTVQHACLAQPLRVELESPESHHHHHH

*Crystal structure-determined epitope is highlighted - FcRn*

>β2-microglobulin chain B (SEQ ID NO: 31)
RTPKIQVYSRHPAEMGKSMFLNCYVSGFHPSDIEVDLLKngeRIEKVEHSDLSFSKDW
SFYLLYYTFTPTEKDEYaCrVNiTLSgKIvkWDRDM

*Crystal structure-determined epitope is highlighted — β2-m*

>N027 Fab HC chain H (SEQ ID NO: 32)
IVQLLESGGGIVQPGGSLRLSCAASGFISMGWVRQAPGKGLEWVSiWt
ADSVKGRFTISRDNSKNTLYLQMNSLRAEDTAVYYCARiCDSIWGQGTMVTVSSASTK
GPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCD

*Crystal structure-determined paratope is highlighted - HC*

>N027 Fab LC chain L (SEQ ID NO: 33)
QSALTQPASVSGSPGQSITISCTGTSYSIWYQQHPGKAPKLMIYSERPSGV
SNRFSGSWTASLTISGLQAEDEADYYCSSTFTGTNVTVLGQPKAAPSVT
LFPPSSEELQANKATLVCLISDFYpgaVtVAWKADsspvkagVETTTPSKQSNNKYAASS
YLSLTPEQWKSHKSYSCQVthegstVEKTVAPTE

*Crystal structure-determined paratope is highlighted - LC*

Key
· Amino acids involved in "dimer" interface are lower case and underlined
· Bold amino acids have not been modeled in the crystal structure due to weak or absent electron density

FcRn ANTIBODIES AND METHODS OF USE THEREOF

BACKGROUND

Therapeutic proteins. e.g., therapeutic antibodies, have rapidly become a clinically important drug class for patients with immunological diseases. Numerous autoimmune and alloimmune diseases are mediated by pathogenic antibodies. For example, many fetal and neonatal immune diseases result from the transfer of maternal antibodies from a pregnant subject, especially a pregnant subject with an immunological disease, to the fetus through the human neonatal Fc receptor (FcRn) in the placenta. There exists a need for novel methods of treating immunological diseases.

SUMMARY

In a first aspect, the application features a method of treating a fetal and neonatal alloimmune and/or autoimmune disorder comprising administering an antibody to a pregnant subject, wherein the antibody includes, includes, comprises, consists of, or consists essentially of, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, includes, comprises, consists of, or consists essentially of, consists of, or consists essentially of a sequence $X_1$GTGSDVGSYNX$_2$VS (SEQ ID NO: 12), the CDR L2 includes, includes, comprises, consists of, or consists essentially of, consists of, or consists essentially of a sequence GDX$_3$X$_4$RPS (SEQ ID NO: 13), the CDR L3 includes, includes, comprises, consists of, or consists essentially of, consists of, or consists essentially of a sequence X$_5$SYX$_6$GSGIYV (SEQ ID NO: 14), the CDR H1 includes, includes, comprises, consists of, or consists essentially of, consists of, or consists essentially of a sequence Z$_1$YAMG (SEQ ID NO: 15), the CDR H2 includes, includes, comprises, consists of, or consists essentially of, consists of, or consists essentially of a sequence Z$_7$IGZ$_2$SGZ$_3$OTZ$_4$YADS (SEQ ID NO: 16), and the CDR H3 includes, includes, comprises, consists of, or consists essentially of, consists of, or consists essentially of a sequence LAZ$_5$Z$_6$DSY (SEQ ID NO: 17), wherein X$_1$ is a polar or hydrophobic amino acid, X$_2$ is a hydrophobic amino acid, X$_3$ is a polar amino acid, X$_4$ is a polar or acidic amino acid, X$_5$ is a polar or hydrophobic amino acid, X$_6$ is a hydrophobic amino acid, Z$_1$ is a polar or acidic amino acid, Z$_2$ is a polar or hydrophobic amino acid, Z$_3$ is G, S, or A, Z$_4$ is a basic amino acid, Z$_5$ is a hydrophobic or basic amino acid, Z$_6$ is G, S, D, Q, or H, and Z$_7$ is S or T.

In some embodiments, the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of the sequence $X_1$GTGSDVGSYNLVS or TGTGSDVGSYNX$_2$VS, the CDR L2 includes, comprises, consists of, or consists essentially of the sequence GDX$_3$ERPS or GDSX$_4$RPS, the CDR L3 includes, comprises, consists of, or consists essentially of the sequence X$_5$SYAGSGIYV or SSYX$_6$GSGIYV, the CDR H1 includes, comprises, consists of, or consists essentially of the sequence of TYAMG (SEQ ID NO: 4), DYAMG (SEQ ID NO: 5), or NYAMG (SEQ ID NO: 6), the CDR H2 includes, comprises, consists of, or consists essentially of the sequence of SIGASGSQTRYADS (SEQ ID NO: 8), SIGSSGAQTRYADS (SEQ ID NO: 7), SIGASGAQTRY-ADS (SEQ ID NO: 9), SIGASGGQTRYADS (SEQ ID NO: 10), TIGSSGAQTRYADS (SEQ ID NO: 41), SIGASGSQTRYADS (SEQ ID NO: 42), TIGASGAQTRY-ADS (SEQ ID NO: 43), or TIGASGGQTRYADS (SEQ ID NO: 32), and the CDR H3 includes, comprises, consists of, or consists essentially of the sequence LAZ$_5$GDSY or LAIZ$_6$DSY.

In some embodiments, the antibody includes, includes, comprises, consists of, or consists essentially of, consists of, or consists essentially of (1) a light chain variable region comprising a CDR L1, a CDR L2, and a CDR L3 and (2) a heavy chain variable region comprising a CDR H1, a CDR H2, and a CDR H3, wherein the CDR L1 includes, includes, comprises, consists of, or consists essentially of, consists of, or consists essentially of the sequence TGTGSDVGSYN-LVS (SEQ ID NO: 1), the CDR L2 includes, includes, comprises, consists of, or consists essentially of, consists of, or consists essentially of the sequence GDSERPS (SEQ ID NO: 2), the CDR L3 includes, includes, comprises, consists of, or consists essentially of, consists of, or consists essentially of the sequence SSYAGSGIYV (SEQ ID NO: 3), the CDR H1 includes, includes, comprises, consists of, or consists essentially of, consists of, or consists essentially of the sequence TYAMG (SEQ ID NO: 4), the CDR H2 includes, comprises, consists of, or consists essentially of the sequence SIGSSGAQTRYADS (SEQ ID NO: 7), or TIGSSGAQTRYADS (SEQ ID NO: 41), and the CDR H3 includes, comprises, consists of, or consists essentially of the sequence LAIGDSY (SEQ ID NO: 11).

In some embodiments, the subject has a history of having had a previous fetal and neonatal alloimmune and/or auto-immune disorder. In some embodiments, the subject is at risk of having a fetal and neonatal alloimmune and/or autoimmune disorder. In some embodiments, the fetal and neonatal alloimmune and/or autoimmune disorder is selected from the group consisting of fetal and neonatal alloimmune thrombocytoponia, hemolytic disease of the fetus and newborn, alloimmune pan-thrombocytopenia, congenital heart block, fetal arthrogryposis, neonatal myasthe-nia gravis, neonatal autoimmune hemolytic anemia, neona-tal anti-phospholipid syndrome, neonatal polymyositis, dermatomyositis, neonatal lupus, neonatal scleroderma, Behcet's disease, neonatal Graves' disease, neonatal Kawa-saki disease, neonatal autoimmune thyroid disease, and neonatal type I diabetes mellitus.

In some embodiments, the fetal and neonatal autoimmune and/or autoimmune disorder is hemolytic disease of the fetus and newborn. In some embodiments, the fetal and neonatal autoimmune and/or autoimmune disorder is fetal and neo-natal alloimmune thrombocytopenia. In some embodiments, the fetal and neonatal autoimmune and/or autoimmune dis-order is congenital heart block.

In some embodiments, treatment reduces the risk of a miscarriage.

In another aspect, the application features a method of treating fetal anemia associated with hemolytic disease of the fetus and newborn, comprising administering an anti-body to a pregnant subject, wherein the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence $X_1$GTGSDVGSYNX$_2$VS (SEQ ID NO: 12), the CDR L2 includes, comprises, consists of, or consists essentially of a sequence GDX$_3$X$_4$RPS (SEQ ID NO: 13), the CDR L3 includes, comprises, consists of, or consists essentially of a sequence X$_5$SYX$_6$GSGIYV (SEQ ID NO: 14), the CDR H1 includes, comprises, consists of, or consists essentially of a sequence Z$_1$YAMG (SEQ ID NO: 15), the CDR H2 includes, comprises, consists of, or consists essentially of a sequence Z$_7$IGZ$_2$SGZ$_3$QTZ$_4$YADS (SEQ ID NO: 16), and the CDR H3 includes, comprises, consists of, or consists essentially of a sequence LAZ$_5$Z$_6$DSY (SEQ ID NO: 17), wherein X$_1$ is a polar or hydrophobic amino acid, X$_2$ is a hydrophobic amino acid, X$_3$ is a polar amino acid, X$_4$ is a polar or acidic amino acid, X$_5$ is a polar or hydrophobic amino acid, X$_6$ is a hydrophobic amino acid, Z$_1$ is a polar or acidic amino acid, Z$_2$ is a polar or hydrophobic amino acid, Z$_3$ is G, S, or A, Z$_4$ is a basic amino acid, Z$_5$ is a hydrophobic or basic amino acid, Z$_6$ is G, S, D, Q, or H, and Z$_7$ is S or T.

In some embodiments, the method treats the pregnant subject, a fetus of the pregnant subject, and/or a combination thereof.

In another aspect, the application features a method of treating an autoimmune disorder, comprising administering an antibody to a pregnant subject. In some embodiments, the autoimmune disorder is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinomia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

In some embodiments, the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence X$_1$GTGSDVGSYNX$_2$VS (SEQ ID NO: 12), the CDR L2 includes, comprises, consists of, or consists essentially of a sequence GDX$_3$X$_4$RPS (SEQ ID NO: 13), the CDR L3 includes, comprises, consists of, or consists essentially of a sequence X$_5$SYX$_6$GSGIYV (SEQ ID NO: 14), the CDR H1 includes, comprises, consists of, or consists essentially of a sequence Z$_1$YAMG (SEQ ID NO: 15), the CDR H2 includes, comprises, consists of, or consists essentially of a sequence Z$_7$IGZ$_2$SGZ$_3$QTZ$_4$YADS (SEQ ID NO: 16), and the CDR H3 includes, comprises, consists of, or consists essentially of a sequence LAZ$_5$Z$_6$DSY (SEQ ID NO: 17), wherein X$_1$ is a polar or hydrophobic amino acid, X$_2$ is a hydrophobic amino acid, X$_3$ is a polar amino acid, X$_4$ is a polar or acidic amino acid, X$_5$ is a polar or hydrophobic amino acid, X$_6$ is a hydrophobic amino acid, Z$_1$ is a polar or acidic amino acid, Z$_2$ is a polar or hydrophobic amino acid, Z$_3$ is G, S, or A, Z$_4$ is a basic amino acid, Z$_5$ is a hydrophobic or basic amino acid, Z$_6$ is G, S, D, Q, or H, and Z$_7$ is S or T.

In some embodiments, the treatment reduces the risk of miscarriage/loss of fetus.

In another aspect, the application features a method of reducing the risk of or reducing the risk of developing an autoimmune or alloimmune disorder, comprising administering an FcRn antibody to a pregnant subject.

In some embodiments, the autoimmune disorder is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma. Sjögren's syndrome, stiff-man syndrome, Takayasu arteritis, temporal arteritis, ulcerative colitis, uveitis, vitiligo, or Wegener's granulomatosis.

In some embodiments, the treatment reduces the risk of miscarriage/loss of fetus.

In another aspect, the application features a method of increasing antibody catabolism in a subject, the method comprising administering an antibody to a pregnant subject, wherein the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence X$_1$GTGSDVGSYNX$_2$VS (SEQ ID NO: 12), the CDR L2 includes, comprises, consists of, or consists essentially of a sequence GDX$_3$X$_4$RPS (SEQ ID NO: 13), the CDR L3 includes, comprises, consists of, or consists essentially of a sequence X$_5$SYX$_6$GSGIYV (SEQ ID NO: 14), the CDR H1 includes, comprises, consists of, or consists essentially of a sequence Z$_1$YAMG (SEQ ID NO: 15), the CDR H2 includes, comprises, consists of, or consists essentially of a sequence Z$_7$IGZ$_2$SGZ$_3$QTZ$_4$YADS (SEQ ID NO: 16), and the CDR H3 includes, comprises, consists of, or consists essentially of a sequence LAZ$_5$Z$_6$DSY (SEQ ID NO: 17), wherein X$_1$ is a polar or hydrophobic amino acid, X$_2$ is a hydrophobic amino acid, X$_3$ is a polar amino acid, X$_4$ is a polar or acidic amino acid, X$_5$ is a polar or hydrophobic amino acid, X$_6$ is a hydrophobic amino acid, Z$_1$ is a polar or acidic amino acid, Z$_2$ is a polar or hydrophobic amino acid, Z$_3$ is G, S, or A, Z$_4$ is a basic amino acid, Z$_5$ is a hydrophobic or basic amino acid, Z$_6$ is G, S, D, Q, or H, and Z$_7$ is S or T.

In some embodiments, increasing antibody catabolism includes, comprises, consists of, or consists essentially of increasing pathogenic antibody catabolism.

In some embodiments, the pathogenic antibody is pathogenic to the mother, the fetus, or both the mother and the fetus.

In some embodiments, the antibody is an IgG antibody.

In another aspect, the application features a method of reducing autoantibodies in a subject, the method comprising administering an antibody to a pregnant subject, wherein the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence $X_1$GTGSDVGSYNX$_2$VS (SEQ ID NO: 12), the CDR L2 includes, comprises, consists of, or consists essentially of a sequence GDX$_3$X$_4$RPS (SEQ ID NO: 13), the CDR L3 includes, comprises, consists of, or consists essentially of a sequence $X_5$SYX$_6$GSGIYV (SEQ ID NO: 14), the CDR H1 includes, comprises, consists of, or consists essentially of a sequence $Z_1$YAMG (SEQ ID NO: 15), the CDR H2 includes, comprises, consists of, or consists essentially of a sequence $Z_7$IGZ$_2$SGZ$_3$QTZ$_4$YADS (SEQ ID NO: 16), and the CDR H3 includes, comprises, consists of, or consists essentially of a sequence LAZ$_5$Z$_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$, is a polar or acidic amino acid, $Z_2$ is a polar or hydrophobic amino acid, $Z_3$ is G, S, or A, $Z_4$ is a basic amino acid, $Z_5$ is a hydrophobic or basic amino acid, $Z_6$ is G, S, D, Q, or H, and $Z_7$ is S or T.

In another aspect, the application features a method of reducing an immune complex-based activation of an immune response in a subject, the method comprising administering an antibody to a pregnant subject, wherein the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence $X_1$GTGSDVGSYNX$_2$VS (SEQ ID NO: 12), the CDR L2 includes, comprises, consists of, or consists essentially of a sequence GDX$_3$X$_4$RPS (SEQ ID NO: 13), the CDR L3 includes, comprises, consists of, or consists essentially of a sequence $X_5$SYX$_6$GSGIYV (SEQ ID NO: 14), the CDR H1 includes, comprises, consists of, or consists essentially of a sequence $Z_1$YAMG (SEQ ID NO: 15), the CDR H2 includes, comprises, consists of, or consists essentially of a sequence $Z_7$IGZ$_2$SGZ$_3$QTZ$_4$YADS (SEQ ID NO: 16), and the CDR H3 includes, comprises, consists of, or consists essentially of a sequence LAZ$_5$Z$_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$ is a polar or acidic amino acid, $Z_2$ is a polar or hydrophobic amino acid, $Z_3$ is G, S, or A, $Z_4$ is a basic amino acid, $Z_5$ is a hydrophobic or basic amino acid, $Z_6$ is G, S, D, Q, or H, and $Z_7$ is S or T.

In some embodiments, the immune response is an acute or chronic immune response in the subject.

In some embodiments, the acute immune response is activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dilated cardiomyopathy, and serum sickness.

In some embodiments, the chronic immune response is activated by a medical condition selected from the group consisting of chronic inflammatory demyelinating polyneuropathy (CIDP), systemic lupus, reactive arthropathies, primary biliary cirrhosis, ulcerative colitis, and antineutrophil cytoplasmic antibody-associated vasculitis. In some embodiments, the chronic immune response is activated by chronic inflammatory demyelinating polyneuropathy.

In some embodiments, the subject has an autoimmune disease. In some embodiments, the autoimmune disease is selected from the group consisting of alopecia areata, ankylosing spondylitis, antiphospholipid syndrome, Addison's disease, hemolytic anemia, warm autoimmune hemolytic anemia, anti-factor antibodies, heparin induced thrombocytopenia, sensitized transplant, autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

In another aspect, the application features a method of decreasing antibody transport across the placenta of a pregnant subject, the method comprising administering an antibody to a pregnant subject, wherein the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence $X_1$GTGSDVGSYNX$_2$VS (SEQ ID NO: 12), the CDR L2 includes, comprises, consists of, or consists essentially of a sequence GDX$_3$X$_4$RPS (SEQ ID NO: 13), the CDR L3 includes, comprises, consists of, or consists essentially of a sequence $X_5$SYX$_6$GSGIYV (SEQ ID NO: 14), the CDR H1 includes, comprises, consists of, or consists essentially of a sequence $Z_1$YAMG (SEQ ID NO: 15), the CDR H2 includes, comprises, consists of, or consists essentially of a sequence $Z_7$IGZ$_2$SGZ$_3$QTZ$_4$YADS (SEQ ID NO: 16), and the CDR H3 includes, comprises, consists of, or consists essentially of a sequence LAZ$_5$Z$_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$ is a polar or acidic amino acid, $Z_2$ is a polar or hydrophobic amino acid, $Z_3$ is G, S, or A, $Z_4$ is a basic amino acid, $Z_5$ is a hydrophobic or basic amino acid, $Z_6$ is G, S, D, Q, or H, and $Z_7$ is S or T.

In another aspect, the application features a method of increasing antibody catabolism in a pregnant subject, the method comprising administering an antibody to a pregnant subject, wherein the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence $X_1$GTGSDVGSYNX$_2$VS (SEQ ID NO: 12), the CDR L2 includes, comprises, consists of, or consists essentially of a sequence GDX$_3$X$_4$RPS (SEQ ID NO: 13), the CDR L3 includes, comprises, consists of, or consists essentially of a sequence X$_5$SYX$_6$GSGIYV (SEQ ID NO: 14), the CDR H1 includes, comprises, consists of, or consists essentially of a sequence $Z_1$YAMG (SEQ ID NO: 15), the CDR H2 includes, comprises, consists of, or consists essentially of a sequence $Z_7$IGZ$_2$SGZ$_3$QTZ$_4$YADS (SEQ ID NO: 16), and the CDR H3 includes, comprises, consists of, or consists essentially of a sequence LAZ$_5$Z$_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$ is a polar or acidic amino acid, $Z_2$ is a polar or hydrophobic amino acid, $Z_3$ is G, S, or A, $Z_4$ is a basic amino acid, $Z_5$ is a hydrophobic or basic amino acid, $Z_6$ is G, S, D, Q, or H, and $Z_7$ is S or T.

In some embodiments, the antibody causes a fetal and neonatal alloimmune and/or autoimmune disorder in a fetus in the pregnant subject.

In some embodiments, the fetal and neonatal alloimmune and/or autoimmune disorder is selected from the group consisting of fetal and neonatal alloimmune thrombocytopenia hemolytic disease of the fetus and newborn, alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma, Behcet's disease, neonatal Graves' disease, neonatal Kawasaki disease, neonatal autoimmune thyroid disease, and neonatal type I diabetes mellitus.

In some embodiments, the antibody is an IgG antibody.

In another aspect, the application features a method of treating an antibody-mediated enhancement of viral disease in a fetus or a neonate, the method comprising administering an antibody to a pregnant subject, wherein the antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence $X_1$GTGSDVGSYNX$_2$VS (SEQ ID NO: 12), the CDR L2 includes, comprises, consists of, or consists essentially of a sequence GDX$_3$X$_4$RPS (SEQ ID NO: 13), the CDR L3 includes, comprises, consists of, or consists essentially of a sequence X$_5$SYX$_6$GSGIYV (SEQ ID NO: 14), the CDR H1 includes, comprises, consists of, or consists essentially of a sequence $Z_1$YAMG (SEQ ID NO: 15), the CDR H2 includes, comprises, consists of, or consists essentially of a sequence $Z_7$IGZ$_2$SGZ$_3$QTZ$_4$YADS (SEQ ID NO: 16), the CDR H3 includes, comprises, consists of, or consists essentially of a sequence LAZ$_5$Z$_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$ is a polar or acidic amino acid, $Z_2$ is a polar or hydrophobic amino acid, $Z_3$ is G, S, or A, $Z_4$ is a basic amino acid, $Z_5$ is a hydrophobic or basic amino acid, $Z_6$ is G, S, D, Q, or H, and $Z_7$ is S or T.

In some embodiments, the viral disease is caused by a virus selected from the group consisting of an alpha virus infection, flavivirus infection, Zika virus infection, Chikungunya virus infection, Ross River virus infection, severe acute respiratory syndrome coronavirus infection, Middle East respiratory syndrome, avian influenza infection, influenza virus infection, human respiratory syncytial virus infection, Ebola virus infection, yellow fever virus infection, dengue virus infection, human immunodeficiency virus infection, respiratory syncytial virus infection, Hantavirus infection, Getah virus infection, Sindbis virus infection, Bunyamwera virus infection, West Nile virus infection, Japanese encephalitis virus B infection, rabbitpox virus infection, lactate dehydrogenase elevating virus infection, reovirus infection, rabies virus infection, foot-and-mouth disease virus infection, porcine reproductive and respiratory syndrome virus infection, simian hemorrhagic fever virus infection, equine infectious anemia virus infection, caprine arthritis virus infection, African swine fever virus infection, lentivirus infection, BK papovavirus infection, Murray Valley encephalitis virus infection, onterovirus infection, cytomegalovirus infection, pneumovirus infection, morbillivirus infection, and measles virus infection.

In some embodiments, the pregnant subject has or is at risk of having a medical condition that activates an immune response in the pregnant subject.

In some embodiments, the medical condition is pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dialated cardiomyopathy, serum sickness, chronic inflammatory demyelinating polyneuropathy, systemic lupus, reactive arthropathies, primary biliary cirrhosis, ulcerative colitis, antineutrophil cytoplasmic antibody (ANCA)-associated vasculitis, alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scieroderma, Sjögren's syndrome, stiff-man syndrome, Takayasu arteritis, temporal arteritis, ulcerative colitis, uveitis, vitiligo, and Wegener's granulomatosis.

In some embodiments, the pregnant subject has a history of having had a previous fetus or neonate that had a fetal and neonatal alloimmune and/or autoimmune disorder.

In some embodiments, an antibody associated with an immune disease is detected in a biological sample obtained from the pregnant subject.

In some embodiments, the biological sample is a blood or urine sample.

In some embodiments, the isolated antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 has a sequence having no more than two amino acid substitutions relative to the sequence of TGTGSDVGSYNLVS (SEQ ID NO: 1), the CDR L2 has a sequence having no more than one amino acid substitution relative to the sequence of GDSERPS (SEQ ID NO: 2), the CDR L3 has a sequence having no more than one amino acid substitution relative to the sequence of SSYAGSGIYV (SEQ ID NO: 3), the CDR H1 has a sequence having no more than one amino acid substitution relative to the sequence of TYAMG (SEQ ID NO: 4), DYAMG (SEQ ID NO: 5), or NYAMG (SEQ ID NO: 6), the CDR H2 has a sequence having no more than two amino acid substitutions relative to the sequence of SIGASGSQTRYADS (SEQ ID NO: 8), SIGSSGAQTRYADS (SEQ ID NO: 7), SIGASGAQTRYADS (SEQ ID NO: 9), SIGASGGQTRYADS (SEQ ID NO: 10), TIGSSGAQTRYADS (SEQ ID NO: 41), SIGASGSQTRYADS (SEQ ID NO: 42), TIGASGAQTRYADS (SEQ ID NO: 43), or TIGASGGQTRYADS (SEQ ID NO: 32), and the CDR H3 has a sequence having no more than one amino acid substitution relative to the sequence of LAIGDSY (SEQ ID NO: 11).

In some embodiments, the isolated antibody includes, comprises, consists of, or consists essentially of: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of the sequence $X_1$GTGSDVGSYNLVS or TGTGSDVGSYNX$_2$VS, the CDR L2 includes, comprises, consists of, or consists essentially of the sequence GDX$_3$ERPS or GDSX$_4$RPS, the CDR L3 includes, comprises, consists of, or consists essentially of the sequence X$_5$SYAGSGIYV or SSYX$_6$GSGIYV, the CDR H1 includes, comprises, consists of, or consists essentially of the sequence of TYAMG (SEQ ID NO: 4), DYAMG (SEQ ID NO: 5), or NYAMG (SEQ ID NO: 6), the CDR H2 includes, comprises, consists of, or consists essentially of the sequence of SIGASGSQTRYADS (SEQ ID NO: 8), SIGSSGAQTRYADS (SEQ ID NO: 7), SIGASGAQTRYADS (SEQ ID NO: 9), SIGASGGQTRYADS (SEQ ID NO: 10), TIGSSGAQTRYADS (SEQ ID NO: 41), SIGASGSQTRYADS (SEQ ID NO: 42), TIGASGAQTRYADS (SEQ ID NO: 43), or TIGASGGOTRYADS (SEQ ID NO: 32), and the CDR H3 includes, comprises, consists of, or consists essentially of the sequence LAZ$_5$GDSY or LAIZ$_6$DSY.

In some embodiments, the antibody includes, comprises, consists of, or consists essentially of the following six CDRs the CDR L1 of sequence TGTGSDVGSYNLVS (SEQ ID NO: 1), the CDR L2 of sequence GDSERPS (SEQ ID NO: 2), the CDR L3 of sequence SSYAGSGIYV (SEQ ID NO: 3), the CDR H1 of sequence TYAMG (SEQ ID NO: 4), the CDR H2 of sequence SIGSSGAQTRYADS (SEQ ID NO: 7), or TIGSSGAQTRYADS (SEQ ID NO: 41), and the CDR H3 of sequence LAIGDSY (SEQ ID NO: 11).

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of the sequence DYAMG (SEQ ID NO: 5), the CDR H2 of the isolated antibody includes, comprises, consists of, or consists essentially of the sequence SIGASGSQTRYADS (SEQ ID NO: 8), and the CDR H3 of the isolated antibody includes, comprises, consists of, or consists essentially of the sequence LAIGDSY (SEQ ID NO: 11).

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of the sequence NYAMG (SEQ ID NO: 6), the CDR H2 of the isolated antibody includes, comprises, consists of, or consists essentially of the sequence SIGASGAQTRYADS (SEQ ID NO: 9) or TIGASGAQTRYADS (SEQ ID NO: 43), and the CDR H3 of the isolated antibody includes, comprises, consists of, or consists essentially of the sequence LAIGDSY (SEQ ID NO: 11).

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of the sequence TYAMG (SEQ ID NO: 4), the CDR H2 of the isolated antibody includes, comprises, consists of, or consists essentially of the sequence SIGASGGQTRYADS (SEQ ID NO: 10) or TIGASGGQTRYADS (SEQ ID NO: 32), and the CDR H3 of the isolated antibody includes, comprises, consists of, or consists essentially of the sequence LAIGDSY (SEQ ID NO: 11).

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of the sequence TYAMG (SEQ ID NO: 4), the CDR H2 of the isolated antibody includes, comprises, consists of, or consists essentially of the sequence SIGASGSQTRYADS (SEQ ID NO: 8), and the CDR H3 of the isolated antibody includes, comprises, consists of, or consists essentially of the sequence LAIGDSY (SEQ ID NO: 11).

In some embodiments, the CDR L1 of the isolated antibody includes, comprises, consists of, or consists essentially of a sequence $X_1$GTGSDVGSYNX$_2$VS (SEQ ID NO: 12), the CDR L2 of the isolated antibody includes, comprises, consists of, or consists essentially of a sequence GDX$_3$X$_4$RPS (SEQ ID NO: 13), the CDR L3 of the isolated antibody includes, comprises, consists of, or consists essentially of a sequence X$_5$SYX$_6$GSGIYV (SEQ ID NO: 14), the CDR H1 of the isolated antibody includes, comprises, consists of, or consists essentially of a sequence $Z_1$YAMG (SEQ ID NO: 15), the CDR H2 of the isolated antibody includes, comprises, consists of, or consists essentially of a sequence $Z_7$IGZ$_2$SGZ$_3$QTZ$_4$YADS (SEQ ID NO: 16), and the CDR H3 of the isolated antibody includes, comprises, consists of, or consists essentially of a sequence LAZ$_5$Z$_6$DSY (SEQ ID NO: 17), wherein $X_1$ is T, A, S, or I, $X_2$ is L or I, $X_3$ is S, N, or T, $X_4$ is Q, E, or N, $X_5$ is C, S, I, or Y, $X_5$ is A or V, $Z_1$ is E, T, D, or N, $Z_2$ is S or A, $Z_3$ is G, S, or A, $Z_4$ is K or R, $Z_5$ is I, L, or H, $Z_6$ is G, S, D, Q, or H, and $Z_7$ is S or T.

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of a sequence $Z_1$YAMG (SEQ ID NO: 15), the CDR H2 of the isolated antibody includes, comprises, consists of, or consists essentially of a sequence $Z_7$IGZ$_2$SGZ$_3$QTRYADS (SEQ ID NO: 18), and the CDR H3 of the isolated antibody includes, comprises, consists of, or consists essentially of the sequence LAIGDSY (SEQ ID NO: 11), and wherein $Z_1$ is T, D, or N, $Z_2$ is S or A, $Z_3$ is G, S or A, and $Z_7$ is S or T.

In some embodiments, the light chain variable region of the isolated antibody includes, comprises, consists of, or consists essentially of a sequence having at least 90% identity to the sequence of

```
                                  (SEQ ID NO: 19)
QSALTQPASVSGSPGQSITISCTGTGSDVGSYNLV

SWYQQHPGKAPKLMIYGDSERPSGVSNRFSGSKSG

NTASLTISGLQAEDEADYYCSSYAGSGIYVFGTGT

KVTVLGQPKAAPSVTLFPPSSEELQANKATLVCLI

SDFYPGAVTVAWKADSSPVKAGVETTTPSKQSNNK

YAASSYLSLTPEQWKSHKSYSCQVTHEGSTVEKTV

APTECS.
```

In some embodiments, the heavy chain variable region of the isolated antibody includes, comprises, consists of, or consists essentially of a sequence having at least 90% identity to the sequence of

```
                                  (SEQ ID NO: 20)
EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the heavy chain variable region of the isolated antibody includes, comprises, consists of, or consists essentially of a sequence having at least 90% identity to the sequence of

```
                                  (SEQ ID NO: 21)
EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the heavy chain variable region of the isolated antibody includes, comprises, consists of, or consists essentially of a sequence having at least 90% identity to the sequence of

```
                                  (SEQ ID NO: 22)
EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV
```

-continued
```
DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the heavy chain variable region of the isolated antibody includes, comprises, consists of, or consists essentially of a sequence having at least 90% identity to the sequence of

```
                                        (SEQ ID NO: 23)
EVQLLESGGGLVQPGGSLRLSCAASGFTFSTYAMG

WVRQAPGKGLEWVSSIGASGGQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the heavy chain variable region of the isolated antibody includes, comprises, consists of, or consists essentially of a sequence having at least 90% identity to the sequence of

```
                                        (SEQ ID NO: 24)
EVQLLESGGGLVQPGGSLRLSCAASGFTFSTYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the light chain variable region of the isolated antibody includes, comprises, consists of, or consists essentially of a sequence having at least 90% identity to the sequence of QSALTQPASVSGSP-GOSITISCTGTGSDVGSYNLVSWYQOHPGKAPKL-MIYGDSERPSGVSNRFSGSKS GNTASLTISOLQAE-DEADYYCSSYAGSGIYVFGTGTKVTVLGQP-KAAPSVTLFPPSSEELQANKATLVCLI SDFYP-GAVTVAWKADSSPVKAGVETTTPSKQSNNKYAASS-YLSLTPEQWKSHKSYSCQVTHEGSTVEK TVAPTECS (SEQ ID NO: 19); and the heavy chain variable region of the isolated antibody has a sequence having at least 90% identity to the sequence of

```
                                        (SEQ ID NO: 20)
EVQLLESGGGLVQPGGSLRLSCAASGFTFSTYAMG

WVRQAPGKGLEWVSSIGSSGAQTRYADSVKGRFTI

SRQNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the light chain variable region of the isolated antibody includes, comprises, consists of, or consists essentially of a sequence having at least 90% identity to the sequence of QSALTE-PASVSGSPGQSITISCTGTGSDVGSYNLVSWYRQ-HPGKAPKLMIYGDSERPSGVSNRFSGSKS GNTAS-LTISGLQAEDEADYYCSSYAGSGIYVFGTGTKVTV-LGQPKAAPSVTLFPPSSEELQANKATLVCLI SDFYP-GAVTVAWKADSSPVKAGVETLTPSKQSNNKYAAS-SYLSLTPEVWKSHKSYSCQVTHEGSTVEK TVAPT-ECS (SEQ ID NO: 19); and the heavy chain variable region of the isolated antibody includes, comprises, consists of, or consists essentially of a sequence having at least 90% identity to the sequence of

```
                                        (SEQ ID NO: 21)
EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG
```

-continued

VEVHNAKTKPREEQYASTYRVSVLTVLHQDWLNGK

EYKCKVSNKALPAPIEKTISKAKGQPREPQVYTLP

PSRDELTKNQVSLTCLVKGFYPSDIAVEWESNGQP

ENNYKTTPPVLDSDGSFFLYSKLTVDKSRWQQGNV

FSCSVMHEALHNHYTQKSLSLSPG.

In some embodiments, the light chain variable region of the isolated antibody includes, comprises, consists of, or consists essentially of a sequence having at least 90% identity to the sequence of QSALTQPASVSGSP-GOSITISCTGTGSDVGSYNLVSWYQOHPGKAPKLMI-YGDSERPSGVSNRFSGSKS GNTASLTISGLQAE-DEADYYCSSYAGSGIYVFGTGTKVTVLGQPKAA-PSVTLFPPSSEELQANKATLVCLI SDFYPGAVTVA-WKADSSPVKAGVETTTPSKQSNNKYAASSYLSLT-PEQWKSHKSYSCQVTHEGSTVEK TVAPTECS (SEQ ID NO: 19); and the heavy chain variable region of the isolated antibody includes, comprises, consists of, or consists essentially of a sequence having at least 90% identity to the sequence of (SEQ ID NO: 22)
EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In some embodiments, the light chain variable region of the isolated antibody includes, comprises, consists of, or consists essentially of a sequence having at least 90% identity to the sequence of QSALTQP-ASVSGSPGQSITISCTGTGSDVGSYNLVSWYQQ-HPGKAPKLMIYGDSERPSGVSNRFSGSKS GNT-ASLTISGLQAEDEADYYCSSYAGSGIYVFGT-GTKVTVLGQPKAAPSVTLFPPSSEELQANKATLVCLI SDFYPGAVTVAWKADSSPVKAGVETTTPSKQSN-NKYAASSYLSLTPEQWKSHKSYSCQVTHEGSTVEK TVAPTECS (SEQ ID NO: 19); and the heavy chain variable region of the isolated antibody includes, comprises, consists of, or consists essentially of a sequence having at least 90% identity to the sequence of (SEQ ID NO: 23)
EVQLLESGGGLVQPGGSLRLSCAASGFTFSTYAMG

WVRQAPGKGLEWVSSIGASGGQTRYADSVKGRFTI

-continued

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In some embodiments, the light chain variable region of the isolated antibody includes, comprises, consists of, or consists essentially of a sequence having at least 90% identity to the sequence of QSALTQPAS-VSGSPGQSITISCTGTGSDVGSYNLVSWYQQHP-GKAPKLMIYGDSERPSGVSNRFSGSKS GNTASLT-ISGLQAEDEADYYCSSYAGSGIYVFGTGTKVTVLG-QPKAAPSVTLFPPSSEELQANKATLVCLI SDFYP-GAVTVAWKADSSPVKAGVETTTPSKOSNNKYAAS-SYLSLTPEQWKSHKSYSCOVTHEGSTVEK TVAPT-ECS (SEQ ID NO: 19); and the heavy chain variable region of the isolated antibody includes, comprises, consists of, or consists essentially of a sequence having at least 90% Identity to the sequence of (SEQ ID NO: 24)
EVQLLESGGGLVQPGGSLRLSCAASGFTFSTYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTQLVKGFYPSDIAVEWESNGQ

PENNYKTTPPVLDSDGSFFLYSKLTVDKSRWQQGN

VFSCSVMHEALHNHYTQKSLSLSPG.

In some embodiments, the heavy chain variable region of the isolated antibody includes, comprises, consists of, or consists essentially of a sequence having at least 95%, 97%, 99%, or 100% identity to the sequence of any one of SEQ ID NOs: 20-24.

In some embodiments, the light chain variable region of the isolated antibody includes, comprises, consists of, or consists essentially of a sequence having at least 95%, 97%, 99%, or 100% identity to the sequence of SEQ ID NO: 19.

In some embodiments, the light chain variable region of the isolated antibody includes, comprises, consists of, or consists essentially of the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVFGT-GTKVTVLGOPKAAPSVTLFPPSSEELQANKATLVCLI SDFYPGAVTVAWKADSSPVKAGVETTTPSKQS-NNKYAASSYLSLTPEQWKSHKSYSCQVTHEGSTVEK TVAPTECS (SEQ ID NO: 19); and the heavy chain variable region of the isolated antibody includes, comprises, consists of, or consists essentially of the sequence of

```
                                 (SEQ ID NO: 20)
EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the light chain variable region of the isolated antibody includes, comprises, consists of, or consists essentially of the sequence of QSALTQPASVSGSPGOSITISCTGTGSDVGSYN-LVSWYQOHPGKAPKLMIYGDSERPSGVSNRFSGSKS GNTASLTISGLQAEDEADYYCSSYAGSGIYVFG-TGTKVTVLGQPKAAPSVTLFPPSSEELQANKAT-LVCLI SDFYPGAVTVAWKADSSPVKAGVETTTPS-KQSNNKYAASSYLSLTPEOWKSHKSYSCQVTHEG-STVEK TVAPTECS (SEQ ID NO: 19); and the heavy chain variable region of the isolated antibody includes, comprises, consists of, or consists essentially of the sequence of

```
                                 (SEQ ID NO: 21)
EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVSVLTVLHQDWLNGK

EYKCKVSNKALPAPIEKTISKAKGQPREPQVYTLP

PSRDELTKNQVSLTCLVKGFYPSDIAVEWESNGQP
```

```
                    -continued
ENNYKTTPPVLDSDGSFFLYSKLTVDKSRWQQGNV

FSCSVMHEALHNHYTQKSLSLSPG.
```

In some embodiments, the light chain variable region of the isolated antibody includes, comprises, consists of, or consists essentially of the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVFG-TGTKVTVLGQPKAAPSVTLFPPSSEELQANKATL-VCLI SDFYPGAVTVAWKADSSPVKAGVETTTPSK-QSNNKYAASSYLSLTPEQWKSHKSYSCQVTHEG-STVEK TVAPTECS (SEQ ID NO: 19); and the heavy chain variable region of the isolated antibody includes, comprises, consists of, or consists essentially of the sequence of

```
                                 (SEQ ID NO: 22)
EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the light chain variable region of the isolated antibody includes, comprises, consists of, or consists essentially of the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVF-GTGTKVTVLGQPKAAPSVTLFPPSSEELQANKA-TLVCLI SDFYPGAVTVAWKADSSPVKAGVETTT-PSKQSNNKYAASSYLSLTPEQWKSHKSYSCQVTHEG-STVEK TVAPTECS (SEQ ID NO: 19); and the heavy chain variable region of the isolated antibody has the sequence of

```
                                 (SEQ ID NO: 23)
EVQLLESGGGLVQPGGSLRLSCAASGFTFSTYAMG

WVRQAPGKGLEWVSSIGASGGQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTQVVVDVSHEDPEVKFNWYVDG
```

-continued

```
VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the light chain variable region of the isolated antibody includes, comprises, consists of, or consists essentially of the sequence of QSAL-TOPASVSGSPGQSITISCTGTGSDVGSYNLVSWYQ-QHPGKAPKLMIYGDSERPSGVSNRFSGSKS GNTASLTISGLQAEDEADYYCSSYAGSGIYVF-GTGTKVTVLGQPKAAPSVTLFPPSSEELQANKAT-LVCLI SDFYPGAVTVAWKADSSPVKAGVETTTPS-KQSNNKYAASSYLSLTPEQWKSHKSYSCQVTHEG-STVEK TVAPTECS (SEQ ID NO: 19); and the heavy chain variable region of the isolated antibody includes, comprises, consists of, or consists essentially of the sequence of (SEQ ID NO: 24)
```
EVQLLESGGGLVQPGGSLRLSCAASGFTFSTYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the antibody binds human FcRn with a $K_D$ of between 1 pM and 100 nM.

In some embodiments, the isolated antibody binds human FcRn with a $K_D$ of less than or equal to that of antibody N026.

In some embodiments, the isolated antibody is a monoclonal antibody.

In some embodiments, the isolated antibody is IgG1 or variant thereof.

In some embodiments, the isolated antibody includes, comprises, consists of, or consists essentially of a λ light chain.

In some embodiments, the isolated antibody is a sialylated antibody.

In another aspect, the application features an isolated antibody that binds to human FcRn, the isolated antibody comprising: (1) a light chain variable region comprising a CDR L1, a CDR L2, and a CDR L3 and (2) a heavy chain variable region comprising a CDR H1, a CDR H2, and a CDR H3, wherein (a) the CDR L1 includes, comprises, consists of, or consists essentially of the sequence SDVGSYNL (SEQ ID NO: 33) or VG_YNL (SEQ ID NO: 34), wherein the "_" can be any amino acid, (b) the CDR L2 includes, comprises, consists of, or consists essentially of the sequence GDSE (SEQ ID NO: 35), (c) the CDR L3 includes, comprises, consists of, or consists essentially of the sequence YAGSGIY (SEQ ID NO: 36), (d) the CDR H1 includes, comprises, consists of, or consists essentially of the sequence TYA (SEQ ID NO: 37), (e) the CDR H2 includes, comprises, consists of, or consists essentially of the sequence SIGASGSQTR (SEQ ID NO: 38) or SI_AS_SQ_R (SEQ ID NO: 39), wherein the "_" can be any amino acid, and (f) the CDR H3 includes, comprises, consists of, or consists essentially of the sequence LAI (SEQ ID NO: 40).

In some embodiments, the antibody recognizes the amino acid sequences a) SEQ ID NO: 25_and b) SEQ ID NO: 26 in the human FcRn.

In some embodiments, the antibody binds to an epitope on FcRn comprising at least one, two, three, four, five, six, seven, eight, nine, ten, eleven, twelve, thirteen, fourteen, fifteen, sixteen, seventeen, eighteen, nineteen, or twenty amino acids selected from the group consisting of K80, A81, L82, G83, G84, K85, G86, P87, Y88, L112, N113, E115, G129, D130, W131, P132, E133, L135, A136, and 0139 of SEQ ID NO: 30.

In some embodiments, the antibody binds to an epitope on FcRn comprising at least one, two, three, four, five, six, seven, eight, nine, ten, eleven, twelve, thirteen, fourteen, fifteen, sixteen, seventeen, eighteen, nineteen, or twenty amino acids selected from the group consisting of K80, A81, L82, G83, G84, K85, G86, P87, Y88, L112, N113, G129, D130, W131, P132, E133, L135, A136, and Q139 of SEQ ID NO: 30.

In some embodiments, the epitope on FcRn includes, comprises, consists of, or consists essentially of W131 and/or Y88 of SEQ ID NO: 30.

In some embodiments, the epitope on FcRn includes, comprises, consists of, or consists essentially of D130W131, W131P132, P87Y88, and/or Y88T89 of SEQ ID NO: 30.

In some embodiments, the epitope on FcRn includes, comprises, consists of, or consists essentially of G129D130W131, W131P132E133, D130W131P132. P87Y88T89, G86P87Y88, and/or Y88T89L90 of SEQ ID NO: 30.

In some embodiments, the epitope on FcRn includes, comprises, consists of, or consists essentially of G129D130W131P132, D130W131P132E133, W131P132E133A134, G128G129D130W131, K85G86P87Y88, G86P87Y88T89, P87Y88T89L90, and/or Y88T89L90Q91 of SEQ ID NO: 30.

In some embodiments, the epitope on FcRn includes, comprises, consists of, or consists essentially of G129D130W131P132E133, D130W131P132E133A134, W131P132E133A134L315, G128G129D130W131P132, W127G128G129D130W131, G84K85G86P87Y88, K85G86P87Y88T89, G86P87Y88T89L90, P87Y88T89L90Q91, and/or Y88T89L90T91Q92 of SEQ ID NO: 30.

In some embodiments, the epitope on FcRn includes, comprises, consists of, or consists essentially of T126W127G128G129D130W131. W127G128G-129D130W131P132, G128G129D130W131P132E133, G129D130W131P132E133A134, D130W131P-132E133A134L135, W131P132E133A134L135A136, G83G84K85G86P87Y88, G84K85G86P87Y88T89, K85G86P87Y88T89L90, G86P87Y88T89L90Q91, P87Y88T89L90T91Q92, and/or Y88T89L90Q91G92L93 of SEQ ID NO: 30.

In some embodiments, the epitope on FcRn includes, comprises, consists of, or consists essentially of one or more amino acids within about 3 amino acids or 10 Angstroms of W131, one or more amino acids within about 5 amino acids or 8 Angstroms Y88, or any two sets of amino amino acids, wherein the first set is or includes W131 and the second set is or includes Y88 of SEQ ID NO: 30.

In some embodiments, the epitope on FcRn includes, comprises, consists of, or consists essentially of K80, A81, L82, G83, G84, K85, G86, P87, Y88, L112, N113, E115, G129, D130, W131, P132, E133, L135, A136, and Q139.

In some embodiments, the isolated antibody binds to an epitope on β2-microglobulin comprising at least one amino acid selected from the group consisting of I1, Q2, P32, and V85 of SEQ ID NO: 31.

In some embodiments, the isolated antibody includes, comprises, consists of, or consists essentially of the amino acid sequence KSG at positions 66-68 Kabat.

In another aspect, the application features an isolated antibody, comprising: (1) a light chain variable region comprising a CDR L1, a CDR L2, and a CDR L3 and (2) a heavy chain variable region comprising a CDR H1, a CDR H2, and a CDR H3, wherein (a) the CDR L1 includes, comprises, consists of, or consists essentially of SDVGSYNL, provided it does not comprise TGTGSDVGSYNLVS (SEQ ID NO: 1), (b) the CDR L2 includes, comprises, consists of, or consists essentially of GDSE, provided it does not comprise GDSERPS (SEQ ID NO: 2), (c) the CDR L3 includes, comprises, consists of, or consists essentially of YAGSGIY, provided it does not comprise SSYAGSGIYV (SEQ ID NO: 3), (d) the CDR H1 includes, comprises, consists of, or consists essentially of TYA, provided it does not comprise TYAMG (SEQ ID NO: 4), (e) the CDR H2 includes, comprises, consists of, or consists essentially of SIGASGSQTR, provided it does not comprise SIGASGSQTRYADS (SEQ ID NO: 8), or (f) the CDR H3 includes, comprises, consists of, or consists essentially of LAI, provided it does not comprise LAIGDSY (SEQ ID NO: 11).

In another aspect, the application features an isolated antibody, comprising: (1) a light chain variable region comprising a CDR L1, a CDR L2, and a CDR L3 and (2) a heavy chain variable region comprising a CDR H1, a CDR H2, and a CDR H3, wherein (a) the CDR L1 includes, comprises, consists of, or consists essentially of TGTGSDVGSYNLVS (SEQ ID NO: 1), wherein no more than six single amino acids are deleted or substituted, provided that no amino acids within the subsequence SDVGSYNL are deleted or substituted, (b) the CDR L2 includes, comprises, consists of, or consists essentially of GDSERPS (SEQ ID NO: 2), wherein no more than three single amino acids are deleted or substituted, provided that no amino acids within the subsequence GDSE are deleted or substituted, (c) the CDR L3 includes, comprises, consists of, or consists essentially of SSYAGSGIYV (SEQ ID NO: 3) wherein no more than three single amino acids are deleted or substituted, provided that no amino acids within the subsequence YAGSGIY are deleted or substituted, (d) the CDR H1 includes, comprises, consists of, or consists essentially of a sequence selected from the group consisting of TYAMG (SEQ ID NO: 4), DYAMG (SEQ ID NO: 5), and NYAMG (SEQ ID NO: 6), wherein no more than three single amino acids are deleted or substituted, provided that no amino acids within the subsequence YA are substituted, (e) the CDR H2 includes, comprises, consists of, or consists essentially of a sequence selected from the group consisting of SIGASGSOTRYADS (SEQ ID NO: 8), SIGSSGAQTRY-ADS (SEQ ID NO: 7), SIGASGAQTRYADS (SEQ ID NO: 9), SIGASGGQTRYADS (SEQ ID NO: 10), TIGSSGAQTRYADS (SEQ ID NO: 41), SIGASGSQTRY-ADS (SEQ ID NO: 42), TIGASGAQTRYADS (SEQ ID NO: 43), and TIGASGGQTRYADS (SEQ ID NO: 32), wherein no more than three single amino acids are deleted or substituted, and (f) the CDR H3 includes, comprises, consists of, or consists essentially of LAIGDSY (SEQ ID NO: 11), wherein no more than four single amino acids are deleted or substituted, provided that no amino acids within the subsequence LAI are deleted or substituted.

In some embodiments, the CDR L1 includes no more than five (e.g., 4, 3, 2, or 1) single amino acid substitutions or deletions. In some embodiments, the CDR L2 includes no more than two (e.g., 1) single amino acid substitutions or deletions. In some embodiments, the CDR L3 includes no more than two (e.g., 1) single amino acid substitutions or deletions. In some embodiments, the CDR H1 includes no more than two (e.g., 1) single amino acid substitutions or deletions. In some embodiments, the CDR H2 includes no more than two (e.g., 1) single amino acid substitutions or deletions. In some embodiments, the CDR H3 includes no more than three (e.g., 2 or 1) single amino acid substitutions or deletions.

In another aspect, the application features an isolated antibody, comprising: (1) a light chain variable region comprising a CDR L1, a CDR L2, and a CDR L3 and (2) a heavy chain variable region comprising a CDR H1, a CDR H2, and a CDR H3, wherein (a) the CDR L1 includes, comprises, consists of, or consists essentially of TGTGSDVGSYNLVS (SEQ ID NO: 1), wherein no more than nine single amino acids are deleted or substituted in SEQ ID NO: 1, provided that no amino acids within the subsequences of VG and YNL of SEQ ID NO: 1 are deleted or substituted, (b) the CDR L2 includes, comprises, consists of, or consists essentially of GDSERPS (SEQ ID NO: 2), wherein no more than three single amino acids are deleted or substituted, provided that no amino acids within the subsequence GDSE are deleted or substituted, (c) the CDR L3 includes, comprises, consists of, or consists essentially of SSYAGSGIYV (SEQ ID NO: 3) wherein no more than three single amino acids are deleted or substituted, provided that no amino acids within the subsequence YAGSGIY are deleted or substituted, (d) the CDR H1 includes, comprises, consists of, or consists essentially of a sequence selected from the group consisting of TYAMG (SEQ ID NO: 4), DYAMG (SEQ ID NO: 5), and NYAMG (SEQ ID NO: 6), wherein no more than three single amino acids are deleted or substituted, provided that no amino acids within the subsequence YA are substituted, (e) the CDR H2 includes, comprises, consists of, or consists essentially of a sequence selected from the group consisting of SIGASGSQTRYADS (SEQ ID NO: 8), SIGSSGAQTRYADS (SEQ ID NO: 7), SIGASGAQTRYADS (SEQ ID NO: 9), SIGASGGQTRY-ADS (SEQ ID NO: 10), TIGSSGAQTRYADS (SEQ ID NO: 41), SIGASGSQTRYADS (SEQ ID NO: 42), TIGASGAQTRYADS (SEQ ID NO: 43), and TIGASGGQTRYADS (SEQ ID NO: 32), wherein no more than seven single amino acids are deleted or substituted, provided that no amino acids within the subsequences SI, AS, SQ, or R are deleted or substituted or (f) the CDR H3 includes, comprises, consists of, or consists essentially of LAIGDSY (SEQ ID NO: 11), wherein no more than four single amino acids are deleted or substituted, provided that no amino acids within the subsequence LAI are deleted or substituted.

In some embodiments, the CDR L1 includes no more than eight (e.g., 7, 6, 5, 4, 3, 2, or 1) single amino acid substitutions or deletions. In some embodiments, the CDR L2 includes no more than two (e.g., 1) single amino acid substitutions or deletions. In some embodiments, the CDR L3 includes no more than two (e.g., 1) single amino acid substitutions or deletions. In some embodiments, the CDR H1 includes no more than two (e.g., 1) single amino acid substitutions or deletions. In some embodiments, the CDR H2 includes no more than six (e.g., 5, 4, 3, 2, or 1) single amino acid substitutions or deletions. In some embodiments, the CDR H3 includes no more than three (e.g., 2 or 1) single amino acid substitutions or deletions.

In some embodiments, the antibody recognizes the amino acid sequences a) SEQ ID NO: 25 and b) SEQ ID NO: 26 in the human FcRn.

In some embodiments, the antibody recognizes an amino acid sequence on FcRn comprising W131 and/or Y88 in SEQ ID NO: 30. In some embodiments, the antibody recognizes an amino acid sequence on FcRn comprising DW, WP, PY, and/or YT in SEQ ID NO: 30. In some embodiments, the antibody recognizes an amino acid sequence on FcRn comprising GDW, WPE, DWP, PYT, GPY, and/or YTL in SEQ ID NO: 30. In some embodiments, the antibody recognizes an amino acid sequence on FcRn comprising GDWP, DWPE, WPEA, GGDW, KGPY, GPYT, PYTL, and/or YTLQ in SEQ ID NO: 30. In some embodiments, the antibody recognizes an amino acid sequence on FcRn comprising GDWPE, DWPEA, WPEAL, GGDWP, WGGDW, GKGPY, KGPYT, GPYTL, PYTLQ, and/or YTLTQ in SEQ ID NO: 30. In some embodiments, the antibody recognizes an amino acid sequence on FcRn comprising TWGGDW, WGGDWP, GGDWPE, GDWPEA, DWPEAL, WPEALA, GGKGPY, GKGPYT, KGPYTL. GPYTLQ, PYTLTQ, and/or YTLQGL in SEQ ID NO: 30. In some embodiments, the antibody recognizes an amino acid sequence on FcRn comprising one or more amino acids within about 3 amino acids or 10 Angstroms of W131, one or more amino acids within about 5 amino acids or 8 Angstroms of Y88, or any two sets of amino acids, wherein the first set is or includes W131 and the second set is or includes Y88 (e.g., Y88 and amino acids around Y88) in SEQ ID NO: 30.

In another aspect, the application features an isolated antibody that binds to human FcRn, wherein the antibody binds to an epitope comprising: (a) a first amino acid sequence comprising at least one amino acid of the sequence of KQGTWGGDWPEAL (SEQ ID NO: 25); and (b) a second amino acid sequence comprising at least one amino acid of the sequence of FKALGGKGPYTL (SEQ ID NO: 26), wherein the antibody inhibits the binding of IgG to human FcRn.

In another aspect, the application features an isolated antibody that binds to human FcRn, wherein the antibody binds to an epitope comprising at least one amino acid in the sequence of KQGTWGGDWPEAL (SEQ ID NO: 25), wherein the antibody binds to at least one of amino acid residues 9, 12, or 13 of SEQ ID NO: 25, and wherein the antibody inhibits the binding of IgG to human FcRn.

In another aspect, the application features an isolated antibody that binds to human FcRn, wherein the antibody binds to an epitope comprising at least one amino acid in the sequence of KQGTWGGDWPEAL (SEQ ID NO: 25) in FcRn, wherein the antibody does not bind to a peptide consisting of the sequence GEEFMNFDLKQGT (SEQ ID NO: 27) or to the sequence of EEFMNFDL (SEQ ID NO: 28), and wherein the antibody inhibits the binding of IgG to human FcRn.

In some embodiments, the epitope includes, comprises, consists of, or consists essentially of at least one amino acid in the sequence of WGGDWPEAL (SEQ ID NO: 29) in FcRn.

In some embodiments, the epitope includes, comprises, consists of, or consists essentially of at least amino acid residue 9 of SEQ ID NO: 25 in FcRn. In some embodiments, the epitope includes, comprises, consists of, or consists essentially of at least amino acid residue 12 of SEQ ID NO: 25 in FcRn. In some embodiments, the epitope includes, comprises, consists of, or consists essentially of at least amino acid residue 13 of SEQ ID NO: 25 in FcRn. In some embodiments, the epitope includes, comprises, consists of, or consists essentially of at least one amino acid of the sequence of FKALGGKGPYTL (SEQ ID NO: 26) in FcRn. In some embodiments, the epitope includes, comprises, consists of, or consists essentially of at least two amino acids of the sequence of FKALGGKGPYTL (SEQ ID NO: 26) in FcRn.

In some embodiments, the antibody binds to an epitope comprising at least one amino acid of the sequence of FKALGGKGPYTL (SEQ ID NO: 26) in FcRn, and wherein the antibody inhibits the binding of IgG to human FcRn. In some embodiments, the epitope includes, comprises, consists of, or consists essentially of at least two amino acids of the sequence of FKALGGKGPYTL (SEQ ID NO: 26) in FcRn.

In some embodiments, the epitope further includes, comprises, consists of, or consists essentially of at least one amino acid of the sequence of KQGTWGGDWPEAL (SEQ ID NO: 25) in FcRn.

In some embodiments, the antibody binds to at least two amino acids of the sequence of KQGTWGGDWPEAL (SEQ ID NO: 25) in FcRn.

In some embodiments, the antibody binds to at least one of amino acid residues 9, 12, or 13 of SEQ ID NO: 25 in FcRn.

In some embodiments, the antibody binds to at least amino acid residue 9 of SEQ ID NO: 25 in FcRn. In some embodiments, the antibody binds to at least amino acid residue 12 of SEQ ID NO: 25 in FcRn. In some embodiments, the antibody binds to at least amino acid residue 13 of SEQ ID NO: 25 in FcRn.

In some embodiments, the antibody binds human FcRn with a $K_D$ of between 1 pM and 100 nM.

In some embodiments, the antibody binds human FcRn with a $K_D$ of no more than that of antibody N026.

In some embodiments, the antibody is a monoclonal antibody.

In some embodiments, the antibody is IgG1.

In some embodiments, the antibody includes, comprises, consists of, or consists essentially of a λ light chain.

In some embodiments, the antibody is a sialylated antibody.

In some embodiments, the antibody is for use in treating a fetal and neonatal alloimmune and/or autoimmune disorder.

In some embodiments, the antibody is for use in reducing the risk of developing a fetal and neonatal alloimmune and/or autoimmune disorder.

In some embodiments, the antibody is for use in reducing the risk of developing an autoimmune or alloimmune disorder.

In some embodiments, the antibody is for use in the treatment of a fetal and neonatal alloimmune and/or autoimmune disorder.

In another aspect, the application features a nucleic acid molecule encoding an isolated antibody of any of the above aspects. In another aspect, the application features a vector comprising the nucleic acid molecule. A host cell may express the isolated antibody, wherein the host cell includes, comprises, consists of, or consists essentially of a nucleic acid molecule or a vector, wherein the nucleic acid molecule or vector is expressed in the host cell. The host cell may be a Chinese hamster ovary (CHO) cell.

In another aspect, the application features a pharmaceutical composition comprising an isolated antibody of any of the above aspects and one or more pharmaceutically acceptable carriers or excipients.

The antibody may be formulated in a therapeutically effective amount.

In another aspect, the application features a method of preparing an isolated antibody of any of the above aspects, the method comprising:

a) providing a host cell comprising a nucleic acid molecule or a vector, and b) expressing the nucleic acid molecule or vector in the host cell under conditions that allow for the formation of the antibody.

In some embodiments, the method may further comprise the step of recovering the antibody at a concentration of about 1-100, 1-50, 1-25, 2-50, 5-50, or 2-20 mg/ml.

In some embodiments, the host cell is a CHO cell.

In another aspect, the application features a method of treating a fetal and neonatal alloimmune and/or autoimmune disorder comprising administering an antibody to a pregnant subject, wherein the antibody is the antibody of any of the above aspects.

In some embodiments, the subject has a history of having had a previous fetal and neonatal alloimmune and/or autoimmune disorder.

In some embodiments, the subject is at risk of having a fetal and neonatal alloimmune and/or autoimmune disorder.

In some embodiments, the fetal and neonatal alloimmune and/or autoimmune disorder is selected from the group consisting of fetal and neonatal alloimmune thrombocytopenia, hemolytic disease of the fetus and newborn, alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma, Behcet's disease, neonatal Graves' disease, neonatal Kawasaki disease, neonatal autoimmune thyroid disease, and neonatal type I diabetes mellitus.

In some embodiments, treatment reduces the risk of a miscarriage.

In another aspect, the application features a method of treating fetal anemia associated with hemolytic disease of the fetus and newborn, comprising administering the antibody of any of the above aspects to a pregnant subject.

In some embodiments, the method treats the pregnant subject, a fetus of the pregnant subject, and/or a combination thereof.

In another aspect, the application features a method of treating an autoimmune disorder, comprising administering the antibody of any of the above aspects to a pregnant subject.

In some embodiments, the autoimmune disorder is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

In some embodiments, the treatment reduces the risk of miscarriage/loss of fetus.

In another aspect, the application features a method of reducing the risk of or reducing the risk of developing an autoimmune or alloimmune disorder, comprising administering the antibody of any of the above aspects to a pregnant subject.

In some embodiments, the autoimmune disorder is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

In some embodiments, the treatment reduces the risk of miscarriage/loss of fetus.

In another aspect, the application features a method of increasing antibody catabolism in a subject, the method comprising administering to the subject an isolated antibody or a pharmaceutical composition of any of the above aspects.

In some embodiments, increasing antibody catabolism includes, comprises, consists of, or consists essentially of increasing pathogenic antibody catabolism.

In some embodiments, the pathogenic antibody is pathogenic to the mother, the fetus, or both the mother and the fetus.

In some embodiments, the antibody is an IgG antibody.

In another aspect, the application features a method of reducing autoantibodies in a subject, the method comprising administering to the subject an isolated antibody or a pharmaceutical composition of any of the above aspects.

In another aspect, the application features a method of reducing an immune complex-based activation of an immune response in a subject, the method comprising administering to the subject an isolated antibody or a pharmaceutical composition of any of the above aspects.

In some embodiments, the immune response is an acute or chronic immune response in the subject.

In some embodiments, the acute immune response is activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dilated cardiomyopathy, and serum sickness.

In some embodiments, the fetal and neonatal autoimmune and/or autoimmune disorder is hemolytic disease of the fetus and newborn.

In some embodiments, the fetal and neonatal autoimmune and/or autoimmune disorder is fetal and neonatal alloimmune thrombocytopenia.

In some embodiments, the fetal and neonatal autoimmune and/or autoimmune disorder is congenital heart block.

In some embodiments, the chronic immune response is activated by a medical condition selected from the group consisting of chronic inflammatory demyelinating polyneuropathy (CIDP), systemic lupus, reactive arthropathies, primary biliary cirrhosis, ulcerative colitis, and antineutrophil cytoplasmic antibody (ANCA)-associated vasculitis.

In some embodiments, the subject has an autoimmune disease.

In some embodiments, the autoimmune disease is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

In another aspect, the application features a method of decreasing antibody transport across the placenta of a pregnant subject, the method comprising administering to the pregnant subject an isolated antibody or a pharmaceutical composition of any of the above aspects.

In some embodiments, decreasing antibody transport includes, comprises, consists of, or consists essentially of decreasing pathogenic antibody transport.

In another aspect, the application features a method of increasing antibody catabolism in a pregnant subject, the method comprising administering to the pregnant subject an isolated antibody or a pharmaceutical composition of any of the above aspects.

In some embodiments, increasing antibody catabolism includes, comprises, consists of, or consists essentially of increasing pathogenic antibody catabolism.

In another aspect, the application features a method of treating an antibody-mediated enhancement of viral disease in a fetus or a neonate, the method comprising administering to a pregnant subject an isolated antibody or a pharmaceutical composition of any of the above aspects.

In some embodiments, the pathogenic antibody causes a fetal and neonatal alloimmune and/or autoimmune disorder in a fetus in the pregnant subject.

In some embodiments, the fetal and neonatal alloimmune and/or autoimmune disorder is selected from the group consisting of fetal and neonatal alloimmune thrombocytopenia, hemolytic disease of the fetus and newborn, alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma, Behcet's disease, neonatal Graves' disease, neonatal Kawasaki disease, neonatal autoimmune thyroid disease, and neonatal type I diabetes mellitus.

In some embodiments, the antibody is an IgG antibody.

In some embodiments, the viral disease is caused by a virus selected from the group consisting of an alpha virus infection, flavivirus infection, Zika virus infection, Chikungunya virus infection, Ross River virus infection, severe acute respiratory syndrome coronavirus infection, Middle East respiratory syndrome, avian influenza infection, influenza virus infection, human respiratory syncytial virus infection, Ebola virus infection, yellow fever virus infection, dengue virus infection, human immunodeficiency virus infection, respiratory syncytial virus infection, Hantavirus infection, Getah virus infection, Sindbis virus infection, Bunyamwera virus infection, West Nile virus infection, Japanese encephalitis virus B infection, rabbitpox virus infection, lactate dehydrogenase elevating virus infection, reovirus infection, rabies virus infection, foot-and-mouth disease virus infection, porcine reproductive and respiratory syndrome virus infection, simian hemorrhagic fever virus infection, equine infectious anemia virus infection, caprine arthritis virus infection, African swine fever virus infection, lentivirus infection, BK papovavirus infection, Murray Valley encephalitis virus infection, enterovirus infection, cytomegalovirus infection, pneumovirus infection, morbillivirus infection, and measles virus infection.

In some embodiments, the pregnant subject has or is at risk of having a medical condition that activates an immune response in the pregnant subject.

In some embodiments, the medical condition is pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dialated cardiomyopathy, serum sickness, chronic inflammatory demyelinating polyneuropathy, systemic lupus, reactive arthropathies, primary biliary cirrhosis, ulcerative colitis, antineutrophil cytoplasmic anti-
body (ANCA)-associated vasculitis, alopecia areata, anky-
losing spondylitis, antiphospholipid syndrome, Addison's
disease, hemolytic anemia, autoimmune hepatitis, hepatitis,
Behcet's disease, bullous pemphigoid, cardiomyopathy,
celiac sprue-dermatitis, chronic fatigue immune dysfunction
syndrome, chronic inflammatory demyelinating polyneu-
ropathy, Churg-Strauss syndrome, cicatricial pemphigoid,
limited scleroderma (CREST syndrome), cold agglutinin
disease, Crohn's disease, dermatomyositis, discoid lupus,
essential mixed cryoglobulinemia, fibromyalgia, fibromyo-
sitis, Graves' disease, Hashimoto's thyroiditis, hypothyroid-
ism, inflammatory bowel disease, autoimmune lymphopro-
liferative syndrome, idiopathic pulmonary fibrosis, IgA
nephropathy, insulin dependent diabetes, juvenile arthritis,
lichen planus, lupus, Ménière's Disease, mixed connective
tissue disease, multiple sclerosis, pernicious anemia, pol-
yarteritis nodosa, polychondritis, polyglandular syndromes,
polymyalgia rheumatica, polymyositis, primary agamma-
globulinomia, primary biliary cirrhosis, psoriasis, Ray-
naud's phenomenon, Reiter's syndrome, rheumatic fever,
rheumatoid arthritis, sarcoidosis, scleroderma, Sjögren's
syndrome, stiff-man syndrome, Takayasu arteritis, temporal
arteritis, ulcerative colitis, uveitis, vitiligo, and Wegener's
granulomatosis.

In some embodiments, the pregnant subject has a history
of having had a previous fetus or neonate that had a fetal and
neonatal alloimmune and/or autoimmune disorder.

In some embodiments, an antibody associated with an
immune disease is detected in a biological sample obtained
from the pregnant subject.

In some embodiments, the biological sample is a blood or
urine sample.

In some embodiments, the antibody binds human FcRn
with a $K_D$ of between 1 pM and 100 nM.

In some embodiments, the isolated antibody binds human
FcRn with a $K_D$ of less than or equal to that of antibody
N026.

In some embodiments, the isolated antibody is a mono-
clonal antibody.

In some embodiments, the isolated antibody is IgG1 or
variant thereof.

In some embodiments, the isolated antibody includes,
comprises, consists of, or consists essentially of a λ light
chain.

In some embodiments, the isolated antibody is a sialylated
antibody.

In another aspect, the application features an isolated
antibody comprising: (1) a light chain variable region com-
prising a CDR L1, a CDR L2, and a CDR L3 and (2) a heavy
chain variable region comprising a CDR H1, a CDR H2, and
a CDR H3, wherein the CDR L1 includes, comprises,
consists of, or consists essentially of a sequence
$X_1$GTGSDVGSYNX$_2$VS (SEQ ID NO: 12), the CDR L2
includes, comprises, consists of, or consists essentially of a
sequence GDX$_3$X$_4$RPS (SEQ ID NO: 13), the CDR L3
includes, comprises, consists of, or consists essentially of a
sequence X$_5$SYX$_6$GSGIYV (SEQ ID NO: 14), the CDR H1
includes, comprises, consists of, or consists essentially of a
sequence Z$_1$YAMG (SEQ ID NO: 15), the CDR H2
includes, comprises, consists of, or consists essentially of a
sequence Z$_7$IGZ$_2$SGZ$_3$QTZ$_4$YADS (SEQ ID NO: 16), the
CDR H3 includes, comprises, consists of, or consists essen-
tially of a sequence LAZ$_5$Z$_6$DSY (SEQ ID NO: 17), wherein
$X_1$ is a polar or hydrophobic amino acid, $X_2$ is a hydrophobic
amino acid, $X_3$ is a polar amino acid, $X_4$ is a polar or acidic
amino acid, $X_5$ is a polar or hydrophobic amino acid, $X_6$ is a hydrophobic amino acid, $Z_1$ is a polar or acidic amino acid,
$Z_2$ is a polar or hydrophobic amino acid, $Z_3$ is G, S, or A, $Z_4$
is a basic amino acid. $Z_5$ is a hydrophobic or basic amino
acid, $Z_6$ is G, S, D, Q, or H, and $Z_7$ is S or T, for use in the
treatment of a fetal and neonatal alloimmune and/or auto-
immune disorder.

In some embodiments, the isolated antibody includes,
comprises, consists of, or consists essentially of: (1) a light
chain variable region comprising a CDR L1, a CDR L2, and
a CDR L3 and (2) a heavy chain variable region comprising
a CDR H1, a CDR H2, and a CDR H3, wherein the CDR L1
includes, comprises, consists of, or consists essentially of a
sequence having no more than two amino acid substitutions
relative to the sequence of TGTGSDVGSYNLVS (SEQ ID
NO: 1), the CDR L2 includes, comprises, consists of, or
consists essentially of a sequence having no more than one
amino acid substitution relative to the sequence of
GDSERPS (SEQ ID NO: 2), the CDR L3 includes, com-
prises, consists of, or consists essentially of a sequence
having no more than one amino acid substitution relative to
the sequence of SSYAGSGIYV (SEQ ID NO: 3), the CDR
H1 includes, comprises, consists of, or consists essentially
of a sequence having no more than one amino acid substi-
tution relative to the sequence of TYAMG (SEQ ID NO: 4),
DYAMG (SEQ ID NO: 5), or NYAMG (SEQ ID NO: 6), the
CDR H2 includes, comprises, consists of, or consists essen-
tially of a sequence having no more than two amino acid
substitutions relative to the sequence of SIGASGSQTRY-
ADS (SEQ ID NO: 8), SIGSSGAQTRYADS (SEQ ID NO:
7), SIGASGAQTRYADS (SEQ ID NO: 9),
SIGASGGQTRYADS (SEQ ID NO: 10), TIGSSGAQTRY-
ADS (SEQ ID NO: 41), SIGASGSQTRYADS (SEQ ID NO:
42), TIGASGAQTRYADS (SEQ ID NO: 43), or TIGASG-
GQTRYADS (SEQ ID NO: 32), and the CDR H3 includes,
comprises, consists of, or consists essentially of a sequence
having no more than one amino acid substitution relative to
the sequence of LAIGDSY (SEQ ID NO: 11), for use in the
treatment of a fetal and neonatal alloimmune and/or auto-
immune disorder.

In some embodiments, the CDR L1 of the isolated anti-
body includes, comprises, consists of, or consists essentially
of the sequence TGTGSDVGSYNLVS (SEQ ID NO: 1), the
CDR L2 of the isolated antibody comprises the sequence
GDSERPS (SEQ ID NO: 2), the CDR L3 of the isolated
antibody includes, comprises, consists of, or consists essen-
tially of the sequence SSYAGSGIYV (SEQ ID NO: 3), the
CDR H1 of the isolated antibody includes, comprises,
consists of, or consists essentially of the sequence TYAMG
(SEQ ID NO: 4), the CDR H2 of the isolated antibody
includes, comprises, consists of, or consists essentially of
the sequence SIGSSGAQTRYADS (SEQ ID NO: 7) or
TIGSSGAQTRYADS (SEQ ID NO: 41), and the CDR H3 of
the isolated antibody includes, comprises, consists of, or
consists essentially of the sequence LAIGDSY (SEQ ID
NO: 11), for use in the treatment of a fetal and neonatal
alloimmune and/or autoimmune disorder.

In some embodiments, the CDR L1 of the isolated anti-
body includes, comprises, consists of, or consists essentially
of the sequence TGTGSDVGSYNLVS (SEQ ID NO: 1), the
CDR L2 of the isolated antibody includes, comprises, con-
sists of, or consists essentially of the sequence GDSERPS
(SEQ ID NO: 2), the CDR L3 of the isolated antibody
includes, comprises, consists of, or consists essentially of
the sequence SSYAGSGIYV (SEQ ID NO: 3), the CDR H1
of the isolated antibody includes, comprises, consists of, or
consists essentially of the sequence DYAMG (SEQ ID NO:
5), the CDR H2 of the isolated antibody includes, comprises, consists of, or consists essentially of the sequence SIGASGSOTRYADS (SEQ ID NO: 8) or SIGASGSQTRY-ADS (SEQ ID NO: 42), and the CDR H3 of the isolated antibody includes, comprises, consists of, or consists essentially of the sequence LAIGDSY (SEQ ID NO: 11), for use in the treatment of a fetal and neonatal alloimmune and/or autoimmune disorder.

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of the sequence NYAMG (SEQ ID NO: 6), the CDR H2 of the isolated antibody includes, comprises, consists of, or consists essentially of the sequence SIGASGAQTRYADS (SEQ ID NO: 9) or TIGASGAQTRYADS (SEQ ID NO: 43), and the CDR H3 of the isolated antibody includes, comprises, consists of, or consists essentially of the sequence LAIGDSY (SEQ ID NO: 11), for use in the treatment of a fetal and neonatal alloimmune and/or autoimmune disorder.

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of the sequence TYAMG (SEQ ID NO: 4), the CDR H2 of the isolated antibody includes, comprises, consists of, or consists essentially of the sequence SIGASGGQTRYADS (SEQ ID NO: 10) or TIGASGGOT-RYADS (SEQ ID NO: 32), and the CDR H3 of the isolated antibody includes, comprises, consists of, or consists essentially of the sequence LAIGDSY (SEQ ID NO: 11), for use in the treatment of a fetal and neonatal alloimmune and/or autoimmune disorder.

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of the sequence TYAMG (SEQ ID NO: 4), the CDR H2 of the isolated antibody includes, comprises, consists of, or consists essentially of the sequence SIGASGSQTRYADS (SEQ ID NO: 8) or SIGASGSQTRY-ADS (SEQ ID NO: 42), and the CDR H3 of the isolated antibody includes, comprises, consists of, or consists essentially of the sequence LAIGDSY (SEQ ID NO: 11), for use in the treatment of a fetal and neonatal alloimmune and/or autoimmune disorder.

In some embodiments, the CDR L1 of the isolated antibody includes, comprises, consists of, or consists essentially of a sequence $X_1$GTGSDVGSYNX$_2$VS (SEQ ID NO: 12), the CDR L2 of the isolated antibody includes, comprises, consists of, or consists essentially of a sequence GDX$_3$X$_4$RPS (SEQ ID NO: 13), the CDR L3 of the isolated antibody includes, comprises, consists of, or consists essentially of a sequence $X_5$SYX$_6$GSGIYV (SEQ ID NO: 14), the CDR H1 of the isolated antibody includes, comprises, consists of, or consists essentially of a sequence $Z_1$YAMG (SEQ ID NO: 15), the CDR H2 of the isolated antibody includes, comprises, consists of, or consists essentially of a sequence $Z_7$IGZ$_2$SGZ$_3$QTZ$_4$YADS (SEQ ID NO: 16), the CDR H3 of the isolated antibody includes, comprises, consists of, or consists essentially of a sequence LAZ$_5$Z$_6$DSY (SEQ ID NO: 17), wherein $X_1$ is T, A, S, or I, $X_2$ is L or I, $X_3$ is S, N, or T, $X_4$ is Q, E, or N, $X_5$ is C, S, I, or Y, $X_6$ is A or V, $Z_1$ is E, T, D, or N, $Z_2$ is S or A, $Z_3$ is G, S, or A, $Z_4$ is K or R, $Z_5$ is I, L, or H, $Z_6$ is G, S, D, Q, or H, and $Z_7$ is S or T, for use in the treatment of a fetal and neonatal alloimmune and/or autoimmune disorder.

In some embodiments, the CDR L1 of the isolated antibody includes, comprises, consists of, or consists essentially of the sequence TGTGSDVGSYNLVS (SEQ ID NO: 1), the CDR L2 of the isolated antibody includes, comprises, consists of, or consists essentially of the sequence GDSERPS (SEQ ID NO: 2), the CDR L3 of the isolated antibody includes, comprises, consists of, or consists essentially of the sequence SSYAGSGIYV (SEQ ID NO: 3), the CDR H1 of the isolated antibody includes, comprises, consists of, or consists essentially of a sequence $Z_1$YAMG (SEQ ID NO: 15), the CDR H2 of the isolated antibody includes, comprises, consists of, or consists essentially of a sequence $Z_7$IGZ$_2$SGZ$_3$QTRYADS (SEQ ID NO: 18), and the CDR H3 of the isolated antibody includes, comprises, consists of, or consists essentially of the sequence LAIGDSY (SEQ ID NO: 11), and wherein $Z_1$ is T, D, or N, $Z_2$ is S or A, $Z_3$ is G, S or A, and $Z_7$ is S or T, for use in the treatment of a fetal and neonatal alloimmune and/or autoimmune disorder.

In some embodiments, the light chain variable region of the isolated antibody includes, comprises, consists of, or consists essentially of a sequence having at least 90% identity to the sequence of QSALTQPASVSGSP-GOSITISCTGTGSDVGSYNLVSWYQQHPGKAPKL-MIYGDSERPSGVSNRFSGSKS GNTASLTISGLQAE-DEADYYCSSYAGSGIYVFGTGTKVTVLGOPKAA-PSVTLFPPSSEELQANKATLVCLI SDFYPGAVTV-AWKADSSPVKAGVETTTPSKQSNNKYAASSYLSLT-PEQWKSHKSYSCQVTHEGSTVEK TVAPTECS (SEQ ID NO: 19), for use in the treatment of a fetal and neonatal alloimmune and/or autoimmune disorder.

In some embodiments, the heavy chain variable region of the isolated antibody includes, comprises, consists of, or consists essentially of a sequence having at least 90% identity to the sequence of EVQLLESGG-GLVQPGGSLRLSCAASGFTFSTYAMGWVRQAPGK-GLEWVSSIGSSGAQTRYADSVKGRF TISRDNSKNT-LYLQMNSLRAEDTAVYYCARLAIGDSYWGQGTMV-TVSSASTKGPSVFPLAPSSKSTSGG TAALGCLVK-DYFPEPVTVSWNSGALTSGVHTFPAVLQSSGLYS-LSSVVTVPSSSLGTQTYICNVNHKPSN TKVDKKVE-PKSCDKTHTCPPCPAPELLGGPSVFLFPPKPKDTLM-ISRTPEVTCVVVDVSHEDPEVKFNWY VDGVEVHN-AKTKPREEQYASTYRVVSVLTVLHQDWLNGKEY-KCKVSNKALPAPIEKTISKAKGQPREPQ VYTLPPS-RDELTKNQVSLTCLVKGFYPSDIAVEWESNGQPEN-NYKTTPPVLDSDGSFFLYSKLTVDKSRW QQGNVF-SCSVMHEALHNHYTQKSLSLSPG (SEQ ID NO: 20), for use in the treatment of a fetal and neonatal alloimmune and/or autoimmune disorder.

In some embodiments, the heavy chain variable region of the isolated antibody includes, comprises, consists of, or consists essentially of a sequence having at least 90% identity to the sequence of EVQLLESGG-GLVQPGGSLRLSCAASGFTFSDYAMGWVRQAPGK-GLEWVSSIGASGSQTRYADSVKGR FTISRDNSKNT-LYLQMNSLRAEDTAVYYCARLAIGDSYWGOGTM-VTVSSASTKGPSVFPLAPSSKSTSG GTAAL-GCLVKDYFPEPVTVSWNSGALTSGVHTFPAVLQSSG-LYSLSSVVTVPSSSLGTQTYICNVNHKPS NTKVDK-KVEPKSCDKTHTCPPCPAPELLGGPSVFLFPPKPK-DTLMISRTPEVTCVVVDVSHEDPEVKFNW YVDGV-EVHNAKTKPREEQYASTYRVVSVLTVLHQDWLNG-KEYKCKVSNKALPAPIEKTISKAKGQPREP QVY-TLPPSRDELTKNQVSLTCLVKGFYPSDIAVEWESNGQ-PENNYKTTPPVLDSDGSFFLYSKLTVDKSR WQQ-GNVFSCSVMHEALHNHYTQKSLSLSPG (SEQ ID NO: 21), for use in the treatment of a fetal and neonatal alloimmune and/or autoimmune disorder.

In some embodiments, the heavy chain variable region of the isolated antibody includes, comprises, consists of, or consists essentially of a sequence having at least 90% identity to the sequence of EVOLLESGGGL-VOPGGSLRLSCAASGFTFSNYAMGWVRQAPGK-GLEWVSSIGASGAQTRYADSVKGR FTISRDNSKNT-LYLQMNSLRAEDTAVYYCARLAIGDSYWGOGTM-VTVSSASTKGPSVFPLAPSSKSTSG GTAAL-GCLVKDYFPEPVTVSWNSGALTSGVHTFPAVLQSSG-LYSLSSVVTVPSSSLGTQTYICNVNHKPS NTKVD-KKVEPKSCDKTHTCPPCPAPELLGGPSVFLFP-PKPKDTLMISRTPEVTCVVVDVSHEDPEVKFNW YVDGVEVHNAKTKPREEQYASTYRVVSVLTVLHQ-DWLNGKEYKC- KVSNKALPAPIEKTISKAKGQPREP OVYTLPPSREEMTKNOVSLTCLVKGFYPSDIA-VEWESNGQPENNYKTTPPVLDSDGSFFLYSK-LTVDKS RWQQGNVFSCSVMHEALHNHYTOKSLSL-SPG (SEQ ID NO: 22), for use in the treatment of a fetal and neonatal alloimmune and/or autoimmune disorder.

In some embodiments, the heavy chain variable region of the isolated antibody includes, comprises, consists of, or consists essentially of a sequence having at least 90% identity to the sequence of EVOLLESGGGL-VOPGGSLRLSCAASGFTFSTYAMGWVROAPGK-GLEWVSSIGASGGQTRYADSVKGR FTISRDNSKNT-LYLQMNSLRAEDTAVYYCARLAIGDSYWGOGTM-VTVSSASTKGPSVFPLAPSSKSTSG GTAALGCLV-KDYFPEPVTVSWNSGALTSGVHTFPAVLQSSGLYS-LSSVVTVPSSSLGTQTYICNVNHKPS NTKVDKKVE-PKSCDKTHTCPPCPAPELLGGPSVFLFPPKPKDTL-MISRTPEVTCVVVDVSHEDPEVKFNW YVDGVEV-HNAKTKPREEOYASTYRVVSVLTVLHQDWLNGKE-YKCKVS- NKALPAPIEKTISKAKGQPREP QVYTLPPS-REEMTKNOVSLTCLVKGFYPSDIAVEWESNGQPEN-NYKTTPPVLDSDGSFFLYSKLTVDKS RWQQGN-VFSCSVMHEALHNHYTQKSLSLSPG (SEQ ID NO: 23), for use in the treatment of a fetal and neonatal alloimmune and/or autoimmune disorder.

In some embodiments, the heavy chain variable region of the isolated antibody includes, comprises, consists of, or consists essentially of a sequence having at least 90% identity to the sequence of EVQLLESGG-GLVQPGGSLRLSCAASGFTFSTYAMGWVRQAPGK-GLEWVSSIGASGSQTRYADSVKGRF TISRDNSKNT-LYLQMNSLRAEDTAVYYCARLAIGDSYWGQGTMVTVS-SASTKGPSVFPLAPSSKSTSGG TAALGCLVKDYFP -EPVTVSWNSGALTSGVHTFPAVLQSSGLYSLSSVVT-VPSSSLGTQTYICNVNHKPSN TKVDKKVEPKSC-DKTHTCPPCPAPELLGGPSVFLFPPKPKDTLMISRTPE-VTCVVVDVSHEDPEVKFNWY VDGVEVHNAK-TKPREEQYASTYRVVSVLTVLHQDWLNGKEYK- CKVSNKALPAPIEKTISKAKGQPREPQ VYTLPPS-REEMTKNQVSLTCLVKGFYPSDIAVEWESNGQPEN-NYKTTPPVLDSDGSFFLYSKLTVDKSR WQQGNV-FSCSVMHEALHNHYTQKSLSLSPG (SEQ ID NO: 24), for use in the treatment of a fetal and neonatal alloimmune and/or autoimmune disorder.

In some embodiments, the light chain variable region of the isolated antibody includes, comprises, consists of, or consists essentially of a sequence having at least 90% identity to the sequence of QSALTQPASVSG-SPGQSITISCTGTGSDVGSYNLVSWYQQHPGK-APKLMIYGDSERPSGVSNRFSGSKS GNTASLT-ISGLQAEDEADYYCSSYAGSGIYVFGTGTK-VTVLGQPKAAPSVTLFPPSSEELQANKATLVCLI SDFYPGAVTVAWKADSSPVKAGVETTTPSKQS-NNKYAASSYLSLTPEQWKSHKSYSCQVTHEGSTVEK TVAPTECS (SEQ ID NO: 19); and the heavy chain variable region of the isolated antibody includes, comprises, consists of, or consists essentially of a sequence having at least 90% identity to the sequence of EVQLLESGGGLVQPGGSL-RLSCAASGFTFSTYAMGWVRQAPGKGLEWVS-SIGSSGAQTRYADSVKGRF TISRDNSKNTLYLQMNS-LRAEDTAVYYCARLAIGDSYWGQGTMVTVSSAS-TKGPSVFPLAPSSKSTSGG TAALGCLVKDYF-PEPVTVSWNSGALTSGVHTFPAVLOSSGLYSLSSVVT-VPSSSLGTQTYICNVNHKPSN TKVDKKVEPKSCD-KTHTCPPCPAPELLGGPSVFLFPPKPKDTLMISRTPE-VTCVVVDVSHEDPEVKFNWY VDGVEVHNAKT-KPREEQYASTYRVVSVLTVLHQDWLNGKEYKC-KVSNKALPAPIEKTISKAKGOPREPQ VYTLPPS-RDELTKNQVSLTCLVKGFYPSDIAVEWESNGQPEN-NYKTTPPVLDSDGSFFLYSKLTVDKSRW QQGNV-FSCSVMHEALHNHYTQKSLSLSPG (SEQ ID NO: 20), for use in the treatment of a fetal and neonatal alloimmune and/or autoimmune disorder.

In some embodiments, the light chain variable region of the isolated antibody includes, comprises, consists of, or consists essentially of a sequence having at least 90% identity to the sequence of QSALTQPAS-VSGSPGQSITISCTGTGSDVGSYNLVSWYQQHPGK-APKLMIYGDSERPSGVSNRFSGSKS GNTASLTIS-GLQAEDEADYYCSSYAGSGIYVFGTGTKVTVLGOP-KAAPSVTLFPPSSEELQANKATLVCLI SDFYP-GAVTVAWKADSSPVKAGVETTTPSKQSNNKYAAS-SYLSLTPEQWKSHKSYSCQVTHEGSTVEK TVAP-TECS (SEQ ID NO: 19); and the heavy chain variable region of the isolated antibody includes, comprises, consists of, or consists essentially of a sequence having at least 90% identity to the sequence of EVQLLESGG-GLVQPGGSLRLSCAASGFTFSDYAMGWVRQAPGK-GLEWVSSIGASGSQTRYADSVKGR FTISRDNSKNT-LYLQMNSLRAEDTAVYYCARLAIGDSYWGQGTMV-TVSSASTKGPSVFPLAPSSKSTSG GTAALGCLVKD-YFPEPVTVSWNSGALTSGVHTFPAVLQSSGLYSLS-SVVTVPSSSLGTQTYICNVNHKPS NTKVDKKVE-PKSCDKTHTCPPCPAPELLGGPSVFLFPPKPKDTL-MISRTPEVTCVVVDVSHEDPEVKFNW YVDGVEVH-NAKTKPREEQYASTYRVVSVLTVLHQDWLNGK-EYKCKVSNKALPAPIEKTISKAKGQPREP QVYTLP-PSRDELTKNQVSLTCLVKGFYPSDIAVEWESNGQ-PENNYKTTPPVLDSDGSFFLYSKLTVDKSR WQQGNVFSCSVMHEALHNHYTQKSLSLSPG (SEQ ID NO: 21), for use in the treatment of a fetal and neonatal alloimmune and/or autoimmune disorder.

In some embodiments, the light chain variable region of the isolated antibody includes, comprises, consists of, or consists essentially of a sequence having at least 90% identity to the sequence of QSALTQPASVSGSP-GQSITISCTGTGSDVGSYNLVSWYQQHPGKAPKLM-IYGDSERPSGVSNRFSGSKS GNTASLTISGLQAE-DEADYYCSSYAGSGIYVFGTGTKVTVLGQPKAAPS-VTLFPPSSEELQANKATLVCLI SDFYPGAVTVAWK-ADSSPVKAGVETTTPSKQSNNKYAASSYLSLT-PEQWKSHKSYSCQVTHEGSTVEK TVAPTECS (SEQ ID NO: 19); and the heavy chain variable region of the isolated antibody includes, comprises, consists of, or consists essentially of a sequence having at least 90% identity to the sequence of EVQLLESGGGLVQPGGSLRLS-CAASGFTFSNYAMGWVRQAPGKGLEWVSSIGASGA-QTRYADSVKGR FTISRDNSKNTLYLQMNSLRAED-TAVYYCARLAIGDSYWGQGTMVTVSSASTKGPSVF-PLAPSSKSTSG GTAALGCLVKDYFPEPVTVSWNS-GALTSGVHTFPAVLQSSGLYSLSSVVTVPSSSLGT-QTYICNVNHKPS NTKVDKKVEPKSCDKTHTCPPCP-APELLGGPSVFLFPPKPKDTLMISRTPEVTCVVVDVS-HEDPEVKFNW YVDGVEVHNAKTKPREEQYAST-YRVVSVLTVLHODWLNGKEYKCKVSNKALPA-PIEKTISKAKGQPREP QVYTLPPSREEMTKNOVSLT-CLVKGFYPSDIAVEWESNGOPENNYKTTPPVLD-SDGSFFLYSKLTVDKS RWQQGNVFSCSVMHEALHN-HYTQKSLSLSPG (SEQ ID NO: 22), for use in the treatment of a fetal and neonatal alloimmune and/or autoimmune disorder.

In some embodiments, the light chain variable region of the isolated antibody includes, comprises, consists of, or consists essentially of a sequence having at least 90% identity to the sequence of QSALTQPASVSG-SPGQSITISCTGTGSDVGSYNLVSWYQQHPGKAPKL-MIYGDSERPSGVSNRFSGSKS GNTASLTISGLQAE-DEADYYCSSYAGSGIYVFGTGTKVTVLGQPKAAPS-VTLFPPSSEELQANKATLVCLI SDFYPGAVTVA-WKADSSPVKAGVETTTPSKQSNNKYAASSYLSLT-PEQWKSHKSYSCQVTHEGSTVEK TVAPTECS (SEQ ID NO: 19); and the heavy chain variable region of the isolated antibody includes, comprises, consists of, or consists essentially of a sequence having at least 90/a identity to the sequence of EVQLLESGGGLVQPGGSLRLS-CAASGFTFSTYAMGWVRQAPGKGLEWVSSIGASG-QTRYADSVKGR FTISRDNSKNTLYLQMNSLRAED-TAVYYCARLAIGDSYWGQGTMVTVSSASTKGPSVF-PLAPSSKSTSG GTAALGCLVKDYFPEPVTVSWN-SGALTSGVHTFPAVLQSSGLYSLSSVVTVPSSSLG-TOTYICNVNHKPS NTKVDKKVEPKSCDKTH-TCPPCPAPELLGGPSVFLFPPKPKDTLMISRTPE-VTCVVVDVSHEDPEVKFNW YVDGVEVHNAK-TKPREEQYASTYRVVSVLTVLHQDWLNGKE-YKCKVSNKALPAPIEKTISKAKGQPREP QVYTLPPS-REEMTKNQVSLTCLVKGFYPSDIAVEWESNGQPEN-NYKTTPPVLDSDGSFFLYSKLTVDKS RWQQGN-VFSCSVMHEALHNHYTQKSLSLSPG (SEQ ID NO: 23), for use in the treatment of a fetal and neonatal alloimmune and/or autoimmune disorder.

In some embodiments, the light chain variable region of the isolated antibody includes, comprises, consists of, or consists essentially of a sequence having at least 90% a identity to the sequence of QSALTQPASVSGS-PGQSITISCTGTGSDVGSYNLVSWYQQHPGKAPKLM-IYGDSERPSGVSNRFSGSKS GNTASLTISGLQAE-DEADYYCSSYAGSGIYVFGTGTKVTVLGQPKAAP-SVTLFPPSSEELQANKATLVCLI SDFYPGAVTVA-WKADSSPVKAGVETTTPSKQSNNKYAASSYLSLT-PEQWKSHKSYSCOVTHEGSTVEK TVAPTECS (SEQ ID NO: 19); and the heavy chain variable region of the isolated antibody includes, comprises, consists of, or consists essentially of a sequence having at least 90% Identity to the sequence of EVQLLESGGGLVQPGGSLRLS-CAASGFTFSTYAMGWVRQAPGKGLEWVSSIGASG-SQTRYADSVKGRF TISRDNSKNTLYLQMNSLRAED-TAVYYCARLAIGDSYWGQGTMVTVSSASTKGPSVF-PLAPSSKSTSGG TAALGCLVKDYFPEPVTVSW-NSGALTSGVHTFPAVLQSSGLYSLSSVVTVPSSSLGT-QTYICNVNHKPSN TKVDKKVEPKSCDKTHTCPP-CPAPELLGGPSVFLFPPKPKDTLMISRTPEVTCVV-VDVSHEDPEVKFNWY VDGVEVHNAKTKPRE-EQYASTYRVVSVLTVLHQDWLNGKEYKCKVSNKA-LPAPIEKTISKAKGQPREPQ VYTLPPSREEMT-KNQVSLTCLVKGFYPSDIAVEWESNGQPENNYKTT-PPVLDSDGSFFLYSKLTVDKSR WQQGNVFSCSV-MHEALHNHYTOKSLSLSPG (SEQ ID NO: 24), for use in the treatment of a fetal and neonatal alloimmune and/or autoimmune disorder.

In some embodiments, the heavy chain variable region of the isolated antibody includes, comprises, consists of, or consists essentially of a sequence having at least 95%, 97%, 99%, or 100% identity to the sequence of any one of SEQ ID NOs: 20-24, for use in the treatment of a fetal and neonatal alloimmune and/or autoimmune disorder.

In some embodiments, the light chain variable region of the isolated antibody includes, comprises, consists of, or consists essentially of a sequence having at least 95%, 97%, 99%, or 100% identity to the sequence of SEQ ID NO: 19, for use in the treatment of a total and neonatal alloimmune and/or autoimmune disorder.

In some embodiments, the light chain variable region of the isolated antibody includes, comprises, consists of, or consists essentially of the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVFGT-GTKVTVLGQPKAAPSVTLFPPSSEELQANKATLVCLI SDFYPGAVTVAWKADSSPVKAGVETTTPSKQS-NNKYAASSYLSLTPEQWKSHKSYSCQVTHEGSTVEK TVAPTECS (SEQ ID NO: 19); and the heavy chain variable region of the isolated antibody includes, comprises, consists of, or consists essentially of the sequence of EVQLLESGG-GLVQPGGSLRLSCAASGFTFSTYAMGWVRQAPGK-GLEWVSSIGSSGAQTRYADSVKGRF TISRDNSKNT-LYLQMNSLRAEDTAVYYCARLAIGDSYWGQGTMV-TVSSASTKGPSVFPLAPSSKSTSGG TAALGCLVK-DYFPEPVTVSWNSGALTSGVHTFPAVLQSSGLYS-LSSVVTVPSSSLGTQTYICNVNHKPSN TKVDKKVE-PKSCDKTHTCPPCPAPELLGGPSVFLFPPKPKDT-LMISRTPEVTCVVVDVSHEDPEVKFNWY VDGVEV-HNAKTKPREEQYASTYRVVSVLTVLHQDWLN-GKEYKCKVSNKALPAPIEKTISKAKGQPREPQ VYTL-PPSRDELTKNQVSLTCLVKGFYPSDIAVEWESNGQ-PENNYKTTPPVLDSDGSFFLYSKLTVDKSRW QQGN-VFSCSVMHEALHNHYTQKSLSLSPG (SEQ ID NO: 20), for use in the treatment of a fetal and neonatal alloimmune and/or autoimmune disorder.

In some embodiments, the light chain variable region of the isolated antibody includes, comprises, consists of, or consists essentially of the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVFG-TGTKVTVLGQPKAAPSVTLFPPSSEELQANKATL-VCLI SDFYPGAVTVAWKADSSPVKAGVETTTPSK-QSNNKYAASSYLSLTPEQWKSHKSYSCQVTHEG-STVEK TVAPTECS (SEQ ID NO: 19); and the heavy chain variable region of the isolated antibody includes, comprises, consists of, or consists essentially of the sequence of EVQLLESGGGLVQPGGSLRLSCAASGFTFSDYA-MGWVRQAPGKGLEWVSSIGASGSQTRYADSVKGR FTISRDNSKNTLYLQMNSLRAEDTAVYYCAR-LAIGDSYWGQGTMVTVSSASTKGPSVFPLAPSS-KSTSG GTAALGCLVKDYFPEPVTVSWNSGALT-SGVHTFPAVLQSSGLYSLSSVVTVPSSSLGTOTYICN-VNHKPS NTKVDKKVEPKSCDKTHTCPPCPAPELL-GGPSVFLFPPKPKDTLMISRTPEVTCVVVDVSHEDPE-VKFNW YVDGVEVHNAKTKPREEQYASTYRVVSV-LTVLHQDWLNGKEYKCKVSNKALPAPIEKTISKA-KGQPREP QVYTLPPSRDELTKNQVSLTCLVKGFYPS-DIAVEWESNGQPENNYKTTPPVLDSDGSFFLYSK-LTVDKSR WQQGNVFSCSVMHEALHNHYTQKSLSL-SPG (SEQ ID NO: 21), for use in the treatment of a fetal and neonatal alloimmune and/or autoimmune disorder.

In some embodiments, the light chain variable region of the isolated antibody includes, comprises, consists of, or consists essentially of the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVFGT-GTKVTVLGQPKAAPSVTLFPPSSEELQANKATLVCLI SDFYPGAVTVAWKADSSPVKAGVETTTPSKQS-NNKYAASSYLSLTPEQWKSHKSYSCQVTHEGSTVEK TVAPTECS (SEQ ID NO: 19); and the heavy chain variable region of the isolated antibody includes, comprises, consists of, or consists essentially of the sequence of EVQLLESGG-GLVQPGGSLRLSCAASGFTFSNYAMGWVRQAPGK-GLEWVSSIGASGAQTRYADSVKGR FTISRDNSKNT-LYLQMNSLRAEDTAVYYCARLAIGDSYWGQGTMV-TVSSASTKGPSVFPLAPSSKSTSG GTAALGCLVKD-YFPEPVTVSWNSGALTSGVHTFPAVLQSSGLYS-LSSVVTVPSSSLGTQTYICNVNHKPS NTKVDKKVE-PKSCDKTHTCPPCPAPELLGGPSVFLFPPKPKDTLM-ISRTPEVTCVVVDVSHEDPEVKFNW YVDGVEVH-NAKTKPREEQYASTYRVVSVLTVLHQDWLNGK-EYKCKVSNKALPAPIEKTISKAKGQPREP QVYTLPPS-REEMTKNQVSLTCLVKGFYPSDIAVEWESNGQPEN-NYKTTPPVLDSDGSFFLYSKLTVDKS RWQQG-NVFSCSVMHEALHNHYTQKSLSLSPG (SEQ ID NO: 22), for use in the treatment of a fetal and neonatal alloimmune and/or autoimmune disorder.

In some embodiments, the light chain variable region of the isolated antibody includes, comprises, consists of, or consists essentially of the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVFGT-GTKVTVLGQPKAAPSVTLFPPSSEELQANKATLVCLI SDFYPGAVTVAWKADSSPVKAGVETTTPSKQS-NNKYAASSYLSLTPEQWKSHKSYSCQVTHEGSTVEK TVAPTECS (SEQ ID NO: 19); and the heavy chain variable region of the isolated antibody includes, comprises, consists of, or consists essentially of the sequence of EVQLLESGG-GLVQPGGSLRLSCAASGFTFSTYAMGWVRQAPGK-GLEWVSSIGASGGQTRYADSVKGR FTISRDNSKNT-LYLQMNSLRAEDTAVYYCARLAIGDSYWGQGTMV-TVSSASTKGPSVFPLAPSSKSTSG GTAALGCLVKD-YFPEPVTVSWNSGALTSGVHTFPAVLQSSGLYS-LSSVVTVPSSSLGTQTYICNVNHKPS NTKVDKKVE-PKSCDKTHTCPPCPAPELLGGPSVFLFPPKPKDTLM-ISRTPEVTCVVVDVSHEDPEVKFNW YVDGVEV-HNAKTKPREEQYASTYRVVSVLTVLHQDWLN-GKEYKCKVSNKALPAPIEKTISKAKGQPREP QVYTLPPSREEMTKNQVSLTCLVKGFYPSDIA- VEWESNGQPENNYKTTPPVLDSDGSFFLYSK-LTVDKS RWQQGNVFSCSVMHEALHNHYTQKSLSL-SPG (SEQ ID NO: 23), for use in the treatment of a fetal and neonatal alloimmune and/or autoimmune disorder.

In some embodiments, the light chain variable region of the isolated antibody includes, comprises, consists of, or consists essentially of the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVF-GTGTKVTVLGQPKAAPSVTLFPPSSEELQANK-ATLVCLI SDFYPGAVTVAWKADSSPVKAGVETT-TPSKQSNNKYAASSYLSLTPEQWKSHKSYS-CQVTHEGSTVEK TVAPTECS (SEQ ID NO: 19); and the heavy chain variable region of the isolated antibody includes, comprises, consists of, or consists essentially of the sequence of EVQLLESGGGLVQPGGSLRLS-CAASGFTFSTYAMGWVRQAPGKGLEWVSSIGASG-SQTRYADSVKGRF TISRDNSKNTLYLQMNSLRAED-TAVYYCARLAIGDSYWGQGTMVTVSSASTKGPSVF-PLAPSSKSTSGG TAALGCLVKDYFPEPVTVSWNSG-ALTSGVHTFPAVLOSSGLYSLSSVVTVPSSSLGT-QTYICNVNHKPSN TKVDKKVEPKSCDKTHTCPP-CPAPELLGGPSVFLFPPKPKDTLMISRTPEVTCVVV-DVSHEDPEVKFNWY VDGVEVHNAKTKPRE-EQYASTYRVVSVLTVLHQDWLNGKEYKCKVSNKA-LPAPIEKTISKAKGQPREPQ VYTLPPSREEMT-KNQVSLTCLVKGFYPSDIAVEWESNGQPENNYKTT-PPVLDSDGSFFLYSKLTVDKSR WQQGNVFSCSVMH-EALHNHYTQKSLSLSPG (SEQ ID NO: 24), for use in the treatment of a fetal and neonatal alloimmune and/or auto-immune disorder.

In another aspect, the application features an isolated antibody comprising: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence VGX$_1$YNX$_2$, the CDR L2 includes, comprises, consists of, or consists essentially of a sequence GDX$_3$X$_4$, the CDR L3 includes, comprises, consists of, or consists essentially of a sequence YX$_6$GSGIY, the CDR H1 includes, comprises, consists of, or consists essentially of a sequence Z$_1$YA, the CDR H2 includes, comprises, consists of, or consists essentially of a sequence Z$_6$IZ$_2$Z$_3$SZ$_4$Z$_5$QZ$_6$R, and the CDR H3 includes, comprises, consists of, or consists essentially of a sequence LAZ$_7$, wherein X$_1$ is any amino acid, X$_2$ is L or I, X$_3$ is S, N, or T, X$_4$ is Q, E, or N, X$_5$ is A or V, Z$_1$ is E, T, D, or N, Z$_2$ is any amino acid Z$_3$ is S or A, Z$_4$ is any amino acid, Z$_5$ is G, S, or A, Z$_6$ is any amino acid, Z$_7$ is I, L, or H, and Z$_8$ is S or T.

In another aspect, the application features an isolated antibody comprising: (1) a light chain variable region comprising a CDR L1, a CDR L2, and a CDR L3 and (2) a heavy chain variable region comprising a CDR H1, a CDR H2, and a CDR H3, wherein the CDR L1 includes, comprises, consists of, or consists essentially of a sequence VGX$_1$YNX$_2$, the CDR L2 includes, comprises, consists of, or consists essentially of a sequence GDX$_3$X$_4$, the CDR L3 includes, comprises, consists of, or consists essentially of a sequence YX$_6$GSGIY, the CDR H1 includes, comprises, consists of, or consists essentially of a sequence Z$_1$YA, the CDR H2 includes, comprises, consists of, or consists essentially of a sequence Z$_8$IZ$_2$Z$_3$SZ$_4$Z$_5$QZ$_6$R, and the CDR H3 includes, comprises, consists of, or consists essentially of a sequence LAZ$_7$, wherein X$_1$ is any amino acid, X$_2$ is a hydrophobic amino acid, X$_3$ is a polar amino acid, X$_4$ is a polar or acidic amino acid, $X_6$ is a hydrophobic amino acid, $Z_1$ is a polar or acidic amino acid, $Z_2$ is any amino acid, $Z_3$ is a polar or hydrophobic amino acid, $Z_4$ is any amino acid, $Z_5$ is G, S, or A, $Z_5$ is a hydrophobic or basic amino acid, $Z_6$ is any amino acid, $Z_7$ is a hydrophobic or basic amino acid, and $Z_8$ is S or T.

In some embodiments, the antibody is for use in the treatment of a fetal and neonatal alloimmune and/or auto-immune disorder. In some embodiments, the antibodies of the previous two aspects are for use with any of the above methods.

In some embodiments, the isolated antibody is an anti-FcRn antibody. In some cases, the antibody inhibits the binding of IgG to FcRn. In some embodiments, the isolated antibody does not bind to E115 of FcRn (SEQ ID NO: 30). In some embodiments, the isolated antibody binds an epitope that does not comprise E115 of FcRn (SEQ ID NO: 30).

The present application also features methods of decreasing pathogenic antibody transport across the placenta of a pregnant subject, increasing pathogenic antibody catabolism in a pregnant subject, and treating an antibody-mediated enhancement of viral disease in a fetus or a neonate by administering to a pregnant subject an isolated antibody that binds to human neonatal Fc receptor (FcRn). In some embodiments, the pathogenic antibody in the pregnant subject causes a fetal and neonatal alloimmune and/or autoimmune disorder in a fetus in the pregnant subject.

In some embodiments, the isolated antibody contains: (1) a light chain variable region that includes a CDR L1, a CDR L2, and a CDR L3 and (2) a heavy chain variable region that includes a CDR H1, a CDR H2, and a CDR H3, wherein the CDR L1 has a sequence having no more than two amino acid substitutions relative to the sequence of TGTGSDVGSYN-LVS (SEQ ID NO: 1), the CDR L2 has a sequence having no more than one amino acid substitution relative to the sequence of GDSERPS (SEQ ID NO: 2), the CDR L3 has a sequence having no more than one amino acid substitution relative to the sequence of SSYAGSGIYV (SEQ ID NO: 3), the CDR H1 has a sequence having no more than one amino acid substitution relative to the sequence of TYAMG (SEQ ID NO: 4), DYAMG (SEQ ID NO: 5), or NYAMG (SEQ ID NO: 6), the CDR H2 has a sequence having no more than two amino acid substitutions relative to the sequence of SIGSSGAQTRYADS (SEQ ID NO: 7), SIGASGSQTRY-ADS (SEQ ID NO: 8), SIGASGAQTRYADS (SEQ ID NO: 9), or SIGASGGQTRYADS (SEQ ID NO: 10), and the CDR H3 has a sequence having no more than one amino acid substitution relative to the sequence of LAIGDSY (SEQ ID NO: 11).

In some embodiments, the antibody binds human FcRn with a $K_D$ of less than 200, 150, 100, 50, or 40 pM.

In some embodiments, the antibody binds human FcRn with a $K_D$ that is less than or equal to that of an antibody having the light chain variable region and heavy chain variable region of N022, N023, N024, N026, or N027, and further having the same Fc region as that of the antibody to which it is being compared.

In other embodiments, the isolated antibody contains: (1) a light chain variable region that includes a CDR L1, a CDR L2, and a CDR L3 and (2) a heavy chain variable region that includes a CDR H1, a CDR H2, and a CDR H3, wherein the CDR L1 has the sequence of $X_1$GTGSDVGSYN$X_2$VS (SEQ ID NO: 12), the CDR L2 has the sequence of GD$X_3X_4$RPS (SEQ ID NO: 13), the CDR L3 has the sequence of $X_5$SYX$_6$GSGIYV (SEQ ID NO: 14), the CDR H1 has the sequence of $Z_1$YAMG (SEQ ID NO: 15), the CDR H2 has the sequence of SIGZ$_2$SGZ$_3$QTZ$_4$YADS (SEQ ID NO: 43), and the CDR H3 has the sequence of LAZ$_5$Z$_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$ is a polar or acidic amino acid. $Z_2$ is a polar or hydrophobic amino acid. $Z_3$ is G, S, or A, $Z_4$ is a basic amino acid, $Z_5$ is a hydrophobic or basic amino acid, and $Z_6$ is G, S, D, Q, or H, and wherein the antibody binds human FcRn with a $K_D$ that is less than or equal to that of antibody having the light chain variable region and heavy chain variable region of N026 and further having the same Fc region as the antibody being compared. In some embodiments, $X_1$ is T, A, S, or I. In other embodiments, $X_2$ is L or I. In some embodiments, $X_3$ is S, N, or T. In still other embodiments, $X_4$ is Q, E, or N, $X_5$ is C, S, I, or Y. In some embodiments, $X_6$ is A or V, $Z_1$ is E, T, D, or N. In further embodiments, $Z_2$ is S or A. In some embodiments, $Z_4$ is K or R. In yet other embodiments, $Z_5$ is I, L, or H.

In still other embodiments, the isolated antibody contains a light chain variable region that includes a CDR L1 having the sequence of TGTGSDVGSYNLVS (SEQ ID NO: 1), a CDR L2 having the sequence of GDSERPS (SEQ ID NO: 2), and a CDR L3 having the sequence of SSYAGSGIYV (SEQ ID NO: 3), and a heavy chain variable region that includes a CDR H1 having the sequence of $Z_1$YAMG (SEQ ID NO: 15), a CDR H2 having the sequence of SIGZ$_2$SGZ$_3$QTRYADS (SEQ ID NO: 44), and a CDR H3 having the sequence of LAIGDSY (SEQ ID NO: 11), wherein $Z_1$ is T, D, or N, $Z_2$ is S or A. and $Z_3$ is G, S or A.

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGSSGAQTRYADS (SEQ ID NO: 7), and a CDR H3 having the sequence of LAIGDSY (SEQ ID NO: 11).

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of DYAMG (SEQ ID NO: 5), a CDR H2 having the sequence of SIGASGSQTRYADS (SEQ ID NO: 8), and a CDR H3 having the sequence of LAIGDSY (SEQ ID NO: 11).

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of NYAMG (SEQ ID NO: 6), a CDR H2 having the sequence of SIGASGAQTRYADS (SEQ ID NO: 9), and a CDR H3 having the sequence of LAIGDSY (SEQ ID NO: 11).

In other embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGASGGQTRYADS (SEQ ID NO: 10), and a CDR H3 having the sequence of LAIGDSY (SEQ ID NO: 11).

In yet other embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGASGSQTRYADS (SEQ ID NO: 8), and a CDR H3 having the sequence of LAIGDSY (SEQ ID NO: 11).

In some embodiments, the light chain variable region of the isolated antibody of the application has a sequence having at least 90% identity to the sequence of

```
                                  (SEQ ID NO: 19)
QSALTQPASVSGSPGQSITISCTGTGSDVGSYNLV

SWYQQHPGKAPKLMIYGDSERPSGVSNRFSGSKSG

NTASLTISGLQAEDEADYYCSSYAGSGIYVFGTGT

KVTVLGQPKAAPSVTLFPPSSEELQANKATLVCLI

SDFYPGAVTVAWKADSSPVKAGVETTTPSKQSNNK

YAASSYLSLTPEQWKSHKSYSCQVTHEGSTVEKTV

APTECS.
```

In some embodiments, the heavy chain variable region of the isolated antibody of the application has a sequence having at least 90% identity to the sequence of

```
                                  (SEQ ID NO: 20)
EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In other embodiments, the heavy chain variable region of the isolated antibody of the application has a sequence having at least 90% identity to the sequence of

```
                                  (SEQ ID NO: 21)
EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS
```

```
-continued
SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In other embodiments, the heavy chain variable region of the isolated antibody of the application has a sequence having at least 90% identity to the sequence of

```
                                  (SEQ ID NO: 22)
EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the heavy chain variable region of the isolated antibody of the application has a sequence having at least 90% identity to the sequence of

```
                                  (SEQ ID NO: 23)
EVQLLESGGGLVQPGGSLRLSCAASGFTFSTYAMG

WVRQAPGKGLEWVSSIGASGGQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVSVLTVLHQDWLNGK

EYKCKVSNKALPAPIEKTISKAKGQPREPQVYTLP

PSREEMTKNQVSLTCLVKGFYPSDIAVEWESNGQP

ENNYKTTPPVLDSDGSFFLYSKLTVDKSRWQQGNV

FSCSVMHEALHNHYTQKSLSLSPG.
```

43

In other embodiments, the heavy chain variable region of the isolated antibody of the application has a sequence having at least 90% identity to the sequence of

```
                                       (SEQ ID NO: 24)
EVQLLESGGGLVQPGGSLRLSCAASGFTFSTYAMG

WVRQAPGKGLEWVSSIGASGSQTRYADSVKGRFTI

SRQNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the isolated antibody contains a light chain variable region and a heavy chain variable region, wherein the light chain variable region has a sequence having at least 90% identity to the sequence of QSALTOPASVSGSPGQSITISCTGTGSDVGSYN-LVSWYOQHPGKAPKLMIYGDSERPSGVSNRFSGSKS GNTASLTISGLQAEDEADYYCSSYAGSGIY-VFGTGTKVTVLGQPKAAPSVTLFPPSSEELQAN-KATLVCLI SDFYPGAVTVAWKADSSPVKAGVETT-TPSKQSNNKYAASSYLSLTPEQWKSHKSYS-CQVTHEGSTVEK TVAPTECS (SEQ ID NO: 19); and the heavy chain variable region has a sequence having at least 90% identity to the sequence of

```
                                       (SEQ ID NO: 20)
EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In other embodiments, the isolated antibody contains a light chain variable region and a heavy chain variable region, wherein the light chain variable region has a sequence having at least 90% identity to the sequence of QSALTOPASVSGSPGQSITISCTGTOSDVGSYN-LVSWYOQHPGKAPKLMIYGDSERPSGVSNRFSGSKS GNTASLTISGLQAEDEADYYCSSYAGSGIYVFGTGT-KVTVLGQPKAAPSVTLFPPSSEELQANKATLVCLI SDFYPGAVTVAWKADSSPVKAGVETTTPSKQS-NNKYAASSYLSLTPEQWKSHKSYSCQVTHEGSTVEK TVAPTECS (SEQ ID NO: 19); and the heavy chain variable region has a sequence having at least 90% identity to the sequence of

```
                                       (SEQ ID NO: 21)
EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In other embodiments, the isolated antibody contains a light chain variable region and a heavy chain variable region, wherein the light chain variable region has a sequence having at least 90% identity to the sequence of QSALTOPASVSGSPGQSITISCTGTGSDVGSYN-LVSWYOQHPGKAPKLMIYGDSERPSGVSNRFSGSKS GNTASLTISGLOAEDEADYYCSSYAGSGIYVFG-TGTKVTVLGQPKAAPSVTLFPPSSEELQANKATL-VCLI SDFYPGAVTVAWKADSSPVKAGVETTTPS-KQSNNKYAASSYLSLTPEQWKSHKSYSCOVTHEG-STVEK TVAPTECS (SEQ ID NO: 19); and the heavy chain variable region has a sequence having at least 90% identity to the sequence of

```
                                       (SEQ ID NO: 22)
EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTQVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ
```

-continued

```
PENNYKTTPPVLDSDGSFFLYSKLTVDKSRWQQGN

VFSCSVMHEALHNHYTQKSLSLSPG.
```

In other embodiments, the isolated antibody contains a light chain variable region and a heavy chain variable region, wherein the light chain variable region has a sequence having at least 90% identity to the sequence of QSALTQPASVSGSPGQSITISCTGTGSDVGSYN-LVSWYQQHPGKAPKLMIVGDSERPSGVSNRFSGSKS GNTASLTISGLQAEDEADYYCSSYAGSGIYVFGT-GTKVTVLGQPKAAPSVTLFPPSSEELQANKATLVCLI SDFYPGAVTVAWKADSSPVKAGVETTTPS-KQSNNKYAASSYLSLTPEQWKSHKSYSCQVTHEG-STVEK TVAPTECS (SEQ ID NO: 19); and the heavy chain variable region has a sequence having at least 90% identity to the sequence of

```
                                    (SEQ ID NO: 23)
EVQLLESGGGLVQPGGSLRLSCAASGFTFSTYAMG

WVRQAPGKGLEWVSSIGASGGQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTQVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In other embodiments, the isolated antibody contains a light chain variable region and a heavy chain variable region, wherein the light chain variable region has a sequence having at least 90% identity to the sequence of QSALTQPASVSGSPGQSITISCTGTGSDVGSYN-LVSWYQHPGKAPKLMIYGDSERPSGVSNRFSGSKS GNTASLTISGLQAEDEADYYCSSYAGSGIYVF-GTGTKVTVLGQPKAAPSVTLFPPSSEELQANKA-TLVCLI    SDFYPGAVTVAWKADSSPVKAGVETTTP-SKQSNNKYAASSYLSLTPEQWKSHKSYSCQVTHEG-STVEK TVAPTECS (SEQ ID NO: 19); and the heavy chain variable region has a sequence having at least 90% identity to the sequence of

```
                                    (SEQ ID NO: 24)
EVQLLESGGGLVQPGGSLRLSCAASGFTFSTYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV
```

-continued

```
DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In some embodiments, the heavy chain variable region of the isolated antibody of the application has a sequence having at least 95%, 97%, 99%, or 100% identity to the sequence of any one of SEQ ID NOs: 20-24. In other embodiments, the light chain variable region of the isolated antibody of the application has a sequence having at least 95%, 97%, 99%, or 100% identity to the sequence of SEQ ID NO: 19.

In some embodiments, the isolated antibody of the application further includes amino acid substitution N297A, relative to the sequence of any one of SEQ ID NOs: 20-24.

In other embodiments, the isolated antibody further includes amino acid substitutions D355E and L357M, relative to the sequence of any one of SEQ ID NOs: 20-24.

In other embodiments, the isolated antibody of the application further includes any one or more of the following amino acid substitutions: A23V, S30R, L80V, A84T, E85D, A93V, relative to the sequence of any one of SEQ ID NOs: 20-24 and Q38H, V58I, and G99D, relative to the sequence of SEQ ID NO: 19.

In yet other embodiment, the isolated antibody of the application does not contain a C-terminal lysine at residue 446, relative to the sequence of any one of SEQ ID NOs: 20-24.

In some embodiments, the antibody of any of the above aspects binds human FcRn with a $K_D$ that is less than or equal to that of an antibody having the light chain variable region and heavy chain variable region of N022, N023, N024, N026, or N027 and also having the same Fc region as that of the antibody being compared. For example, in a particular $K_D$ assay, the $K_D$ of the antibody is less than 200, 150, 100, 50, or 40 pM.

The amino acid positions assigned to complementary determining regions (CDRs) and framework regions (FRs) of any isolated antibody described herein are defined according to EU index of Kabat (Sequences of Proteins of Immunological Interest, 5th Ed. Public Health Service, National Institutes of Health. Bethesda, MD (1991)).

In some embodiments, the isolated antibody contains a light chain variable region and a heavy chain variable region, wherein the light chain variable region has the sequence of QSALTQPASVSGSPGQSITISCTGTGSDV-GSYNLVSWYQQHPGKAPKLMIYGDSERPSGVS-NRFSGSKS      GNTASLTISGLQAEDEADYYCSSY-AGSGIYVFGTGTKVTVLGQPKAAPSVTLFPPS-SEELQANKATLVCLI   SDFYPGAVTVAWKADSSPVK-AGVETTTPSKQSNNKYAASSYLSLTPEQWKSHKSY- SCQVTHEGSTVEK TVAPTECS (SEQ ID NO: 19); and the heavy chain variable region has the sequence of (SEQ ID NO: 20)

EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In some embodiments, the isolated antibody contains a light chain variable region and a heavy chain variable region, wherein the light chain variable region has the sequence of QSALTOPASVSGSPGQSITIS-CTGTGSDVGSYNLVSWYQQHPGKAPKLMIYGD-SERPSGVSNRFSGSKS GNTASLTISGLQAEDEAD-YYCSSYAGSGIYVFGTGTKVTVLGQPKAAPSVTLFP-PSSEELQANKATLVCLI SDFYPGAVTVAWKADSS-PVKAGVETTTPSKQSNNKYAASSYLSLTPEQWKSHK-SYSCOVTHEGSTVEK TVAPTECS (SEQ ID NO: 19); and the heavy chain variable region has the sequence of (SEQ ID NO: 21)

EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In some embodiments, the isolated antibody contains a light chain variable region and a heavy chain variable region, wherein the light chain variable region has the sequence of QSALTQPASVSGSPGQSITISCTGTGSD-VGSYNLVSWYQOHPGKAPKLMIYGDSERPSGVS-NRFSGSKS GNTASLTISGLQAEDEADYYCSSY-AGSGIYVFGTGTKVTVLGQPKAAPSVTLFPPS- SEELQANKATLVCLI SDFYPGAVTVAWKADSSPVK-AGVETTTPSKOSNNKYAASSYLSLTPEQWKSHKSYS-CQVTHEGSTVEK TVAPTECS (SEQ ID NO: 19); and the heavy chain variable region has the sequence of (SEQ ID NO: 22)

EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In some embodiments, the isolated antibody contains a light chain variable region and a heavy chain variable region, wherein the light chain variable region has the sequence of OSALTQPASVSGSPGOSITISCTGTG-SDVGSVNLVSWYQQHPGKAPKLMIYGDSERPSGV-SNRFSGSKS GNTASLTISGLQAEDEADYVCSSY-AGSGIYVFGTGTKVTVLGQPKAAPSVTLFPPS-SEELQANKATLVCLI SDFYPGAVTVAWKADSSPVK-AGVETTTPSKQSNNKYAASSYLSLTPEQWKSHKSYS-CQVTHEGSTVEK TVAPTECS (SEQ ID NO: 19); and the heavy chain variable region has the sequence of (SEQ ID NO: 23)

EVQLLESGGGLVQPGGSLRLSCAASGFTFSTYAMG

WVRQAPGKGLEWVSSIGASGGQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In some embodiments, the isolated antibody contains a light chain variable region and a heavy chain variable region, wherein the light chain variable region has the sequence of QSALTQPASVSGSPGQSITISCTGTGS-DVGSYNLVSWYQQHPGKAPKLMIYGDSERPSG-VSNRFSGSKS GNTASLTISGLQAEDEADYVCSSY-AGSGIYVFGTGTKVTVLGQPKAAPSVTLFPPS-SEELQANKATLVCLI SDFYPGAVTVAWKADSSPVK-AGVETTTPSKQSNNKYAASSYLSLTPEQWKSHKSY-SCQVTHEGSTVEK TVAPTECS (SEQ ID NO: 19); and the heavy chain variable region has the sequence of

```
                                 (SEQ ID NO: 24)
EVQLLESGGGLVQPGGSLRLSCAASGFTFSTYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTQLVKGFYPSDIAVEWESNGQ

PENNYKTTPPVLDSDGSFFLYSKLTVDKSRWQQGN

VFSCSVMHEALHNHYTQKSLSLSPG.
```

In some embodiments of any of the above aspects, the isolated antibody of the application is a monoclonal antibody. In some embodiments, the isolated antibody is IgG1. In some embodiments, the isolated antibody includes a λ light chain. In some embodiments, the isolated antibody includes a kappa light chain. In some embodiments, the glycosylation site on the Fc region of the isolated antibody is sialylated (e.g., disialylated).

In some embodiments of any of the above aspects, the isolated antibody of the application is a humanized or fully human antibody.

In some embodiments, the isolated antibody binds to human FcRn with a $K_D$ of 1-100, 5-150, 5-100, 5-75, 5-50, 10-50, or 10-40 pM.

In some embodiments, the isolated antibody of the application binds rodent, e.g., mouse or rat FcRn. In some embodiments, the isolated antibody of the application binds rodent, e.g., mouse or rat, FcRn with a $K_D$ of less than 200, 150, 100, 50, or 40 pM.

The present application features novel antibodies to human neonatal Fc receptor (FcRn). These anti-FcRn antibodies are useful, e.g., to promote clearance of autoantibodies in a subject, to suppress antigen presentation in a subject, to block an immune response, e.g., block an immune complex-based activation of the immune response in a subject, or to treat immunological diseases (e.g., autoimmune diseases) in a subject. These anti-FcRn antibodies are also useful in methods of decreasing pathogenic antibody transport across the placenta of a pregnant subject, increasing pathogenic antibody catabolism in a pregnant subject, and treating an antibody-mediated enhancement of viral disease in a fetus or a neonate by administering to a pregnant subject an isolated antibody that binds to FcRn. In some embodiments, the pathogenic antibody in the pregnant subject causes a fetal and neonatal alloimmune and/or autoimmune disorder in a fetus in the pregnant subject.

In one aspect, the application features an isolated antibody that binds to FcRn, wherein the antibody binds to: (a) at least one amino acid of the sequence of KQGTWGGDWPEAL (SEQ ID NO: 25); and (b) at least one amino acid of the sequence of FKALGGKGPYTL (SEQ ID NO: 26), wherein the antibody inhibits the binding of IgG to human FcRn.

In another aspect, the application features an isolated antibody that binds to human FcRn, wherein the antibody binds to at least one amino acid of the sequence of KQGTWGGDWPEAL (SEQ ID NO: 25), wherein the antibody binds to at least one of amino acid residues 5, 12, or 13 of SEQ ID NO: 25, and wherein the antibody inhibits the binding of IgG to human FcRn.

In another aspect, the application features an isolated antibody that binds to human FcRn, wherein the antibody binds to at least one amino acid of the sequence of KQGTWGGDWPEAL (SEQ ID NO: 25), wherein the antibody does not bind to a peptide consisting of the sequence GEEFMNFDLKQGT (SEQ ID NO: 27) or one or more amino acids of the sequence of EEFMNFDL (SEQ ID NO: 28), and wherein the antibody inhibits the binding of IgG to human FcRn.

In some embodiments, the antibody binds to at least one amino acid of the sequence of WGGDWPEAL (SEQ ID NO: 29).

In some embodiments, the antibody binds to at least amino acid residue 5 of SEQ ID NO: 25. In some embodiments, the antibody binds to at least amino acid residue 12 of SEQ ID NO: 25. In some embodiments, the antibody binds to at least amino acid residue 13 of SEQ ID NO: 25.

In some embodiments, the antibody binds to at least one amino acid of the sequence of FKALGGKGPYTL (SEQ ID NO: 26). In some embodiments, the antibody at least two amino acids of the sequence of FKALGGKGPYTL (SEQ ID NO: 26).

In another aspect, the application features an isolated antibody that binds to human FcRn, wherein the antibody binds at least one amino acid of the sequence of FKAL-GGKGPYTL (SEQ ID NO: 26), and wherein the antibody inhibits the binding of IgG to human FcRn. In some embodiments, the antibody binds to at least two amino acids of the sequence of FKALGGKGPYTL (SEQ ID NO: 26).

In some embodiments, the antibody further binds to at least one amino acid of the sequence of KQGTWGGDWPEAL (SEQ ID NO: 25). In some embodiments, the antibody further binds to at least two amino acids of the sequence of KQGTWGGDWPEAL (SEQ ID NO: 25).

In some embodiments, the antibody binds to at least one of amino acid residues 5, 12, or 13 of SEQ ID NO: 25. In some embodiments, the antibody binds to at least amino acid residue 5 of SEQ ID NO: 25. In some embodiments, the antibody binds to at least amino acid residue 12 of SEQ ID NO: 25. In some embodiments, the antibody binds to at least amino acid residue 13 of SEQ ID NO: 25.

In some embodiments, the antibody described herein binds human FcRn with a $K_D$ of less than or equal to that of antibody N026.

In some embodiments, the antibody is a monoclonal antibody. In some embodiments, the antibody is IgG1. In some embodiments, the antibody includes a λ light chain. In some embodiments, the isolated antibody includes a kappa light chain. In some embodiments, the antibody is a sialylated (e.g., disialylated) antibody. In some embodiments, the antibody is a humanized or fully human antibody.

In another aspect, the application features a nucleic acid molecule encoding an isolated anti-FcRn antibody described herein.

In another aspect, the application features a vector including the nucleic acid molecule that encodes an isolated anti-FcRn antibody described herein.

In another aspect, the application features a host cell that expresses an isolated anti-FcRn antibody described herein, wherein the host cell includes a nucleic acid molecule that encodes the isolated anti-FcRn antibody or a vector that includes the nucleic acid molecule, wherein the nucleic acid molecule or vector is expressed in the host cell. In some embodiments, the host cell is a Chinese hamster ovary (CHO) cell.

In another aspect, the application features a pharmaceutical composition including an isolated anti-FcRn antibody described herein and one or more pharmaceutically acceptable carriers or excipients. In some embodiments, the antibody is in a therapeutically effective amount.

In another aspect, the application features a method of preparing an isolated anti-FcRn antibody described herein, wherein the method includes: a) providing a host cell including a nucleic acid molecule that encodes the isolated anti-FcRn antibody or a vector that includes the nucleic acid molecule, and b) expressing the nucleic acid molecule or vector in the host cell under conditions that allow for the formation of the antibody.

In some embodiments, the method further includes the step of recovering the antibody at a concentration of about 1-100, 1-50, 1-25, 2-50, 5-50, or 2-20 mg/ml.

In some embodiments, the host cell used in the method is a CHO cell.

In another aspect, the application features a method of increasing pathogenic antibody (e.g., an IgG antibody) catabolism in a subject. In another aspect, the application features a method of reducing autoantibodies in a subject. In yet another aspect, the application features a method of reducing an immune complex-based activation of an immune response in a subject. The methods include administering to the subject an isolated antibody described herein or a pharmaceutical composition described herein.

In some embodiments, the immune response is an acute or chronic immune response in the subject.

In some embodiments, the acute immune response is activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura (ITP), autoimmune haemolytic anaemia (AIHA), immune neutropenia, dialated cardiomyopathy, and serum sickness.

In some embodiments, the chronic immune response is activated by a medical condition selected from the group consisting of chronic inflammatory demyelinating polyneuropathy (CIDP), systemic lupus, reactive arthropathies, primary biliary cirrhosis, ulcerative colitis, and antineutrophil cytoplasmic antibody (ANCA)-associated vasculitis.

In some embodiments, the subject has an autoimmune disease. The autoimmune disease may be alopecia areata, ankylosing spondylitis, antiphospholipid syndrome, Addison's disease, hemolytic anemia, autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

In another aspect, the application features a method of decreasing pathogenic antibody transport across the placenta of a pregnant subject. In another aspect, the application features a method of increasing pathogenic antibody catabolism in a pregnant subject. In yet another aspect, the application features a method of treating an antibody-mediated enhancement of viral disease in a fetus or a neonate. The methods include administering to the pregnant subject an isolated antibody described herein or a pharmaceutical composition described herein.

In some embodiments, the pathogenic antibody causes a fetal and neonatal alloimmune and/or autoimmune disorder in a fetus in the pregnant subject.

In some embodiments, the fetal and neonatal alloimmune and/or autoimmune disorder is selected from the group consisting of fetal and neonatal alloimmune thrombocytopenia (FNAIT), hemolytic disease of the fetus and newborn (HDFN), alloimmune pan-thrombocytopenia, congenital heart block, fetal arthrogryposis, neonatal myasthenia gravis, neonatal autoimmune hemolytic anemia, neonatal antiphospholipid syndrome, neonatal polymyositis, dermatomyositis, neonatal lupus, neonatal scleroderma. Behcet's disease, neonatal Graves' disease, neonatal Kawasaki disease, neonatal autoimmune thyroid disease, and neonatal type I diabetes mellitus.

In some embodiments, the pathogenic antibody is an IgG antibody.

In some embodiments, the viral disease is caused by a virus selected from the group consisting of an alpha virus infection, flavivirus infection, Zika virus infection, Chikungunya virus infection, Ross River virus infection, severe acute respiratory syndrome coronavirus infection, Middle East respiratory syndrome, avian influenza infection, influenza virus infection, human respiratory syncytial virus infection, Ebola virus infection, yellow fever virus infection, dengue virus infection, human immunodeficiency virus infection, respiratory syncytial virus infection, Hantavirus infection, Getah virus infection, Sindbis virus infection, Bunyamwera virus infection, West Nile virus infection, Japanese encephalitis virus B infection, rabbitpox virus infection, lactate dehydrogenase elevating virus infection, reovirus infection, rabies virus infection, foot-and-mouth disease virus infection, porcine reproductive and respiratory syndrome virus infection, simian hemorrhagic fever virus infection, equine infectious anemia virus infection, caprine arthritis virus infection, African swine fever virus infection, lentivirus infection, BK papovavirus infection, Murray Valley encephalitis virus infection, enterovirus infection, cytomegalovirus infection, pneumovirus infection, morbillivirus infection, and measles virus infection.

In some embodiments, the pregnant subject has or is at risk of having a medical condition that activates an immune response in the pregnant subject. In some embodiments, the medical condition is pemphigus vulgaris, lupus nephritis, myasthenia gravis, Guillain-Barre syndrome, antibody-mediated rejection, catastrophic anti-phospholipid antibody syndrome, immune complex-mediated vasculitis, glomerulitis, a channolopathy, nouromyolitis optica, autoimmune hearing loss, idiopathic thrombocytopenia purpura, autoimmune haemolytic anaemia, immune neutropenia, dialated cardiomyopathy, serum sickness, chronic inflammatory demyelinating polyneuropathy, systemic lupus, reactive arthropathies, primary biliary cirrhosis, ulcerative colitis, antineutrophil cytoplasmic antibody (ANCA)-associated vasculitis, alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

In some embodiments, the pregnant subject has a history of having had a previous fetus or neonate that had a fetal and neonatal alloimmune and/or autoimmune disorder.

In some embodiments, a pathogenic antibody associated with an immune disease is detected in a biological sample (e.g., a blood or urine sample) obtained from the pregnant subject.

In some embodiments, the isolated anti-FcRn antibody of the application binds rodent, e.g., mouse or rat FcRn. In some embodiments, the isolated anti-FcRn antibody of the application binds rodent, e.g., mouse or rat, FcRn with a $K_D$ of less than 200, 150, 100, 50, or 40 pM.

Definitions

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit FcRn antigen-binding activity.

"Antibody fragments" comprise a portion of an intact antibody, preferably the antigen binding or variable region of the intact antibody. Examples of antibody fragments include Fab, Fab', F(ab')$_2$, and Fv fragments, diabodies, linear antibodies, single-chain antibody molecules, and multispecific antibodies.

As used herein, the term "isolated antibody" refers to an antibody which has been separated and/or recovered from a component of its manufacturing host cell environment. Contaminant components of its manufacturing host cell environment are materials which would interfere with research, diagnostic, or therapeutic uses of the antibody. Contaminant components may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or non-reducing conditions using, for example, Coomassie blue or silver stain. An isolated antibody includes the antibody in situ within recombinant cells. Ordinarily, however, an isolated antibody will be prepared by at least one purification step. A pharmaceutical preparation of an isolated antibody typically has less than 250 ppm (e.g., less than 200 ppm, 150 ppm, 100 ppm) of host cell proteins (HCP) as determined by an ELISA based HCP assay performed as recommended by an FDA "Guidance for Industry" document.

As used herein, the term "monoclonal antibody" refers to an antibody obtained from a population of substantially homogeneous antibodies, i.e., individual antibodies in the population have the same primary sequence except for possible naturally occurring mutations that may be present in minor amounts. Monoclonal antibodies are highly specific and directed against a single antigenic site (i.e., an epitope on human FcRn). In contrast to polyclonal antibody preparations which typically include different antibodies directed against different epitopes, each monoclonal antibody is directed against a single epitope on the antigen. The modifier "monoclonal" indicates the character of the antibody as being obtained from a substantially homogenous population of antibodies, and is not to be construed as requiring production of the antibody by any particular method.

As used herein, the terms "variable region" and "variable domain" refer to the portions of the light and heavy chains of an antibody that include amino acid sequences of complementary determining regions (CDRs, e.g., CDR L1, CDR L2, CDR L3, CDR H1, CDR H2, and CDR H3) and framework regions (FRs). According to the methods used in this disclosure, the amino acid positions assigned to CDRs and FRs are defined according to Kabat (Sequences of Proteins of Immunological Interest, 5th Ed. Public Health Service, National Institutes of Health, Bethesda, MD (1991)). Using this numbering system, the actual linear amino acid sequence may contain fewer or additional amino acids corresponding to a shortening of, or insertion into, a CDR (defined further herein) or FR (defined further herein) of the variable region. For example, a heavy chain variable region may include a single inserted residue (i.e., residue 52a according to Kabat) after residue 52 of CDR H2 and inserted residues (i.e., residues 82a, 82b, 82c, etc. according to Kabat) after residue 82 of heavy chain FR. The Kabat numbering of residues may be determined for a given antibody by alignment at regions of homology of the sequence of the antibody with a "standard" Kabat numbered sequence.

As used herein, the terms "complementary determining regions" and "CDRs" refer to the regions of an antibody variable domain which are hypervariable in sequence and/or form structurally defined loops. A CDR is also known as a hypervariable region. The light chain and heavy chain variable regions each has three CDRs. The light chain variable region contains CDR L1, CDR L2, and CDR L3. The heavy chain variable region contains CDR H1, CDR H2, and CDR H3. Each CDR may include amino acid residues from a complementarity determining region as defined by Kabat (i.e. about residues 24-34 (CDR L1), 50-56 (CDR L2) and 89-97 (CDR L3) in the light chain variable region and about residues 31-35 (CDR H1), 50-65 (CDR H2) and 95-102 (CDR H3) in the heavy chain variable region.

As used herein, the term "FcRn" refers to a neonatal Fc receptor that binds to the Fc region of an IgG antibody, e.g., an IgG1 antibody. An exemplary FcRn is human FcRn having UniProt ID No. P55899. Human FcRn is believed to be responsible for maintaining the half-life of IgG by binding and trafficking constitutively internalized IgG back to the cell surface for the recycling of IgG.

As used herein, the terms "affinity" and "binding affinity" refer to the strength of the binding interaction between two molecules. Generally, binding affinity refers to the strength of the sum total of non-covalent interactions between a single binding site of a molecule and its binding partner, such as an isolated antibody and its target (e.g., an isolated anti-FcRn antibody and a human FcRn). Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. One method for determining the $K_D$ of an antibody to human FcRn is described in Example 2 ("the SPR (Surface Plasmon Resonance) method"). Using this method the $K_D$ of N022, N023, N024, N026, and N027 was 31, 31.4, 35.5, 36.5, and 19.3 pM, respectively.

As used herein, the term "inhibit IgG binding to FcRn" refers to the ability of an anti-FcRn antibody to block or inhibit the binding of IgG (e.g., IgG1) to human FcRn. In some embodiments, an anti-FcRn antibody binds FcRn, for example, at the site on human FcRn to which IgG binds. Thus, the anti-FcRn antibody is able to inhibit the binding of IgG (e.g., a subject's autoantibodies) to FcRn. In some embodiments, the molecule (e.g., an anti-FcRn antibody) substantially or completely inhibits binding to IgG. In some embodiments, the binding of IgG is reduced by 10%, 20%, 30%, 50%, 70%, 80%, 90%, 95%, or even 100%.

As used herein, the term "inhibit pathogenic antibody binding to FcRn" refers to the ability of an anti-FcRn antibody to block or inhibit the binding of a pathogenic antibody (e.g., pathogenic IgG antibody) to human FcRn. In some embodiments, an anti-FcRn antibody binds FcRn, for example, at the site on human FcRn to which the pathogenic antibody binds. Thus, the anti-FcRn antibody is able to inhibit the binding of pathogenic antibodies (e.g., pathogenic IgG antibodies) to FcRn. In some embodiments, the molecule (e.g., an anti-FcRn antibody) substantially or completely inhibits binding to pathogenic antibodies. In some embodiments, the binding of pathogenic antibodies to FcRn is reduced by 10%, 20%, 30%, 50%, 70%, 80%, 90%, 95%, or even 100%.

As used herein, the term "hydrophobic amino acid" refers to an amino acid having relatively low-water solubility. Hydrophobic amino acids are glycine, leucine, isoleucine, alanine, phenylalanine, methionine, tryptophan, valine, and proline. Particularly preferred hydrophobic amino acids in the present disclosure are alanine, leucine, isoleucine, and valine.

As used herein, the term "polar amino acid" refers to an amino acid having a chemical polarity in its side chain induced by atoms with different electronegativity. The polarity of a polar amino acid is dependent on the electronegativity between atoms in the side chain of the amino acid and the asymmetry of the structure of the side chain. Polar amino acids are serine, threonine, cysteine, histidine, methionine, tyrosine, tryptophan, asparagine, and glutamine. Particularly preferred polar amino acids in the present disclosure are serine, threonine, asparagine, glutamine, cysteine, and tyrosine.

As used herein, the term "acidic amino acid" refers to an amino acid whose side chain contains a carboxylic acid group having a pKa between 3.5 and 4.5. Acidic amino acids are aspartic acid and glutamic acid.

As used herein, the term "basic amino acid" refers to an amino acid whose side chain contains an amino group having a pKa between 9.5 and 13. Basic amino acids are histidine, lysine, and arginine.

As used herein, the term "percent (%) identity" refers to the percentage of amino acid (or nucleic acid) residues of a candidate sequence, e.g., an anti-FcRn antibody, that are identical to the amino acid (or nucleic acid) residues of a reference sequence, e.g., a wild-type anti-FcRn antibody, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position. A position may be altered by a substitution, deletion, or insertion. A substitution, deletion, or insertion may comprise a certain number of amino acids, (e.g., 1, 2, 3, 4, 5, 6, 7, 8, 9, 10, 11, 12, 13, 14, 15, or more). When describing a substitution, deletion, or insertion of no more than n amino acids, this is meant that the substitution, deletion, or insertion comprises, e.g., 1, 2, 3, 4, 5, 6, 7, 8, 9, 10, 11, 12, 13, 14, 15, . . . or n amino acids. The number or substitutions, deletions, or insertions can comprise a percent of the total sequence (e.g., 1%, 5%, 10%, 15%, 20%, or more) where the number of substitutions, deletions, or insertions alters 5%, 10%, 15%, 20% or more, of the amino acids in the total sequence. As used herein, the term "fetal and neonatal alloimmune and/or autoimmune disorder" refers to an immune disorder in a fetus and/or neonate that is caused by the transplacental transfer of maternal antibodies (e.g., pathogenic maternal antibodies) directed against fetal and/or neonate antigens. For example, a pregnant subject's antibodies (e.g., pathogenic antibodies) may react against antigens in the fetus (e.g., antigens the fetus inherited from the fetus' father). Examples of fetal and neonatal alloimmune and/or autoimmune disorders are provided herein.

As used herein, the term "pathogenic antibody" refers to an antibody that causes one or more immune diseases or disorders in a subject (e.g., a pregnant subject), a fetus in a pregnant subject, and/or a neonate. In some embodiments, pathogenic antibodies are autoantibodies produced in a subject (e.g., a pregnant subject) against one or more of the subject's own proteins, thus causing autoimmune diseases or disorders in the subject. In some embodiments, pathogenic antibodies in a pregnant subject may transfer through the placenta to the fetus and react against antigens from the fetus (e.g., antigens that the fetus inherited from the fetus' father), thus causing, e.g., fetal and neonatal alloimmune and/or autoimmune disorders.

As used herein, the term "antibody-mediated enhancement of viral disease" refers to a viral disease in which antibodies can facilitate viral entry into host cells, thus leading to increased or enhanced infectivity in the cells. In some embodiments, an antibody may bind to a viral surface protein and the antibody/virus complex may bind to an FcRn receptor on a cell surface through interaction between the antibody and the receptor. Subsequently, the antibody/virus complex may get internalized into the cell.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (e.g., transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell). As described herein, a host cell is used to express one or more polypeptides encoding anti-FcRn antibodies.

As used herein, the term "vector" refers to a nucleic acid molecule capable of transporting another nucleic acid molecule to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids.

As used herein, the term "subject" refers to a mammal, e.g., preferably a human. Mammals include, but are not limited to, humans and domestic and farm animals, such as monkeys (e.g., a cynomolgus monkey), mice, dogs, cats, horses, and cows, etc.

As used herein, the term "pharmaceutical composition" refers to a medicinal or pharmaceutical formulation that contains an active ingredient as well as one or more excipients and diluents to enable the active ingredient suitable for the method of administration. The pharmaceutical composition includes pharmaceutically acceptable components that are compatible with the anti-FcRn antibody. The pharmaceutical composition may be in aqueous form for intravenous or subcutaneous administration or in tablet or capsule form for oral administration.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. The pharmaceutically acceptable carrier must provide adequate pharmaceutical stability to the Fc construct. The nature of the carrier differs with the mode of administration. For example, for intravenous administration, an aqueous solution carrier is generally used; for oral administration, a solid carrier is preferred.

As used herein, the term "therapeutically effective amount" refers to an amount, e.g., pharmaceutical dose, effective in inducing a desired biological effect in a subject or patient or In treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

As used herein, the term "no more than" refers to an amount that is less than equal to. This may be an amount in integers. For example, no more than two substitutions can refer to 0, 1, or 2 substitutions.

As used herein, the terms "treatment" or "treating" refer to reducing, decreasing, decreasing the risk of, or decreasing the side effects of a particular disease or condition. Reducing, decreasing, decreasing the risk of, or decreasing the side effects of are relative to a subject who did not receive treatment, e.g., a control, a baseline, or a known control level or measurement.

DESCRIPTION OF THE DRAWINGS

FIG. 6 shows an experimental timeline and a graph that shows the efficacy of N027 in a mouse collagen antibody-induced arthritis model in transgenic mice.

FIGS. 8A-8C show graphs that show the dose-dependent FcRn occupancy achieved with N027 in aortic endothelial cells, venous endothelial cells, and placental trophoblast, respectively.

FIGS. 9A-9C show graphs that show 100% FcRn occupancy by N027 results in increased intracellular IgG accumulation in aortic endothelial cells, venous endothelial cells, and placental trophoblast, respectively.

FIGS. 12A and 12B show images of FcRn localized in endosomes in human endothelial and villous trophoblast cells.

FIGS. 13C and 13D show images that show N027 increases intracellular IgG and co-localization of IgG with lysosomes (lysosomal markers: Lamp-1 and Dextran).

FIG. 14 shows images of a comparison of the N027 Fab binding site on FcRn with Fc and albumin binding sites. Fab and Fc binding sites overlap with each other but are distinct from the albumin binding site.

FIG. 16 shows the N027 Fab:FcRn epitope and paratope mapped to sequences.

Figure 19:
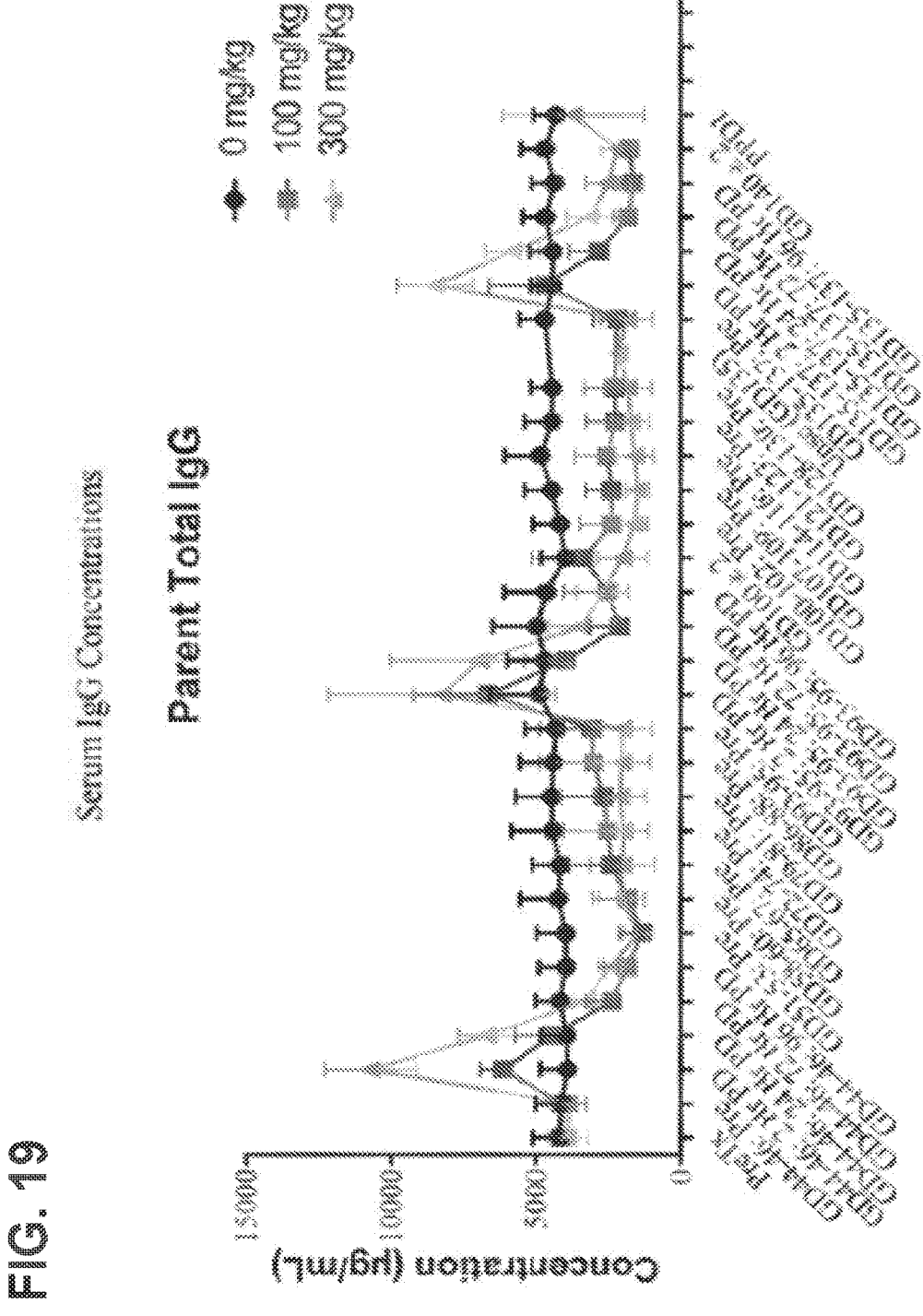

FIG. 19 is a graph showing maternal IgG concentrations after treatment with N027 during gestation.

Figure 20:
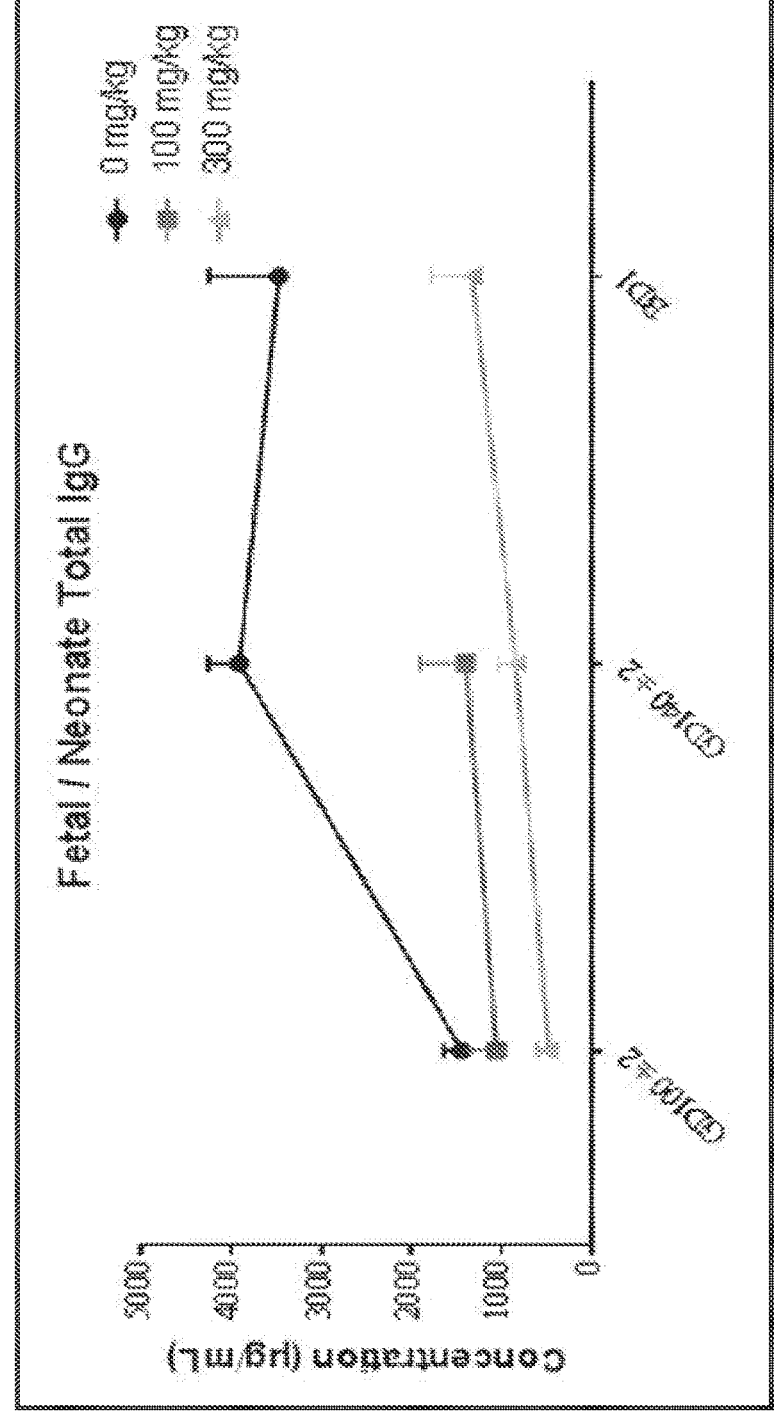

FIG. 20 is a graph showing fetal IgG levels after treatment of mothers with N027 during gestation.

DETAILED DESCRIPTION

The present disclosure features isolated antibodies that bind to human neonatal Fc receptor (FcRn) with high affinity. The present disclosure features anti-FcRn antibodies, methods and compositions for preparing anti-FcRn antibodies, and methods for blocking FcRn activity, reducing immune complex-based activation of an immune response, and treating immunological diseases. Furthermore, anti-FcRn antibodies can be used to decrease pathogenic antibody transport across the placenta of a pregnant subject, to increase pathogenic antibody catabolism in a pregnant subject, and to treat an antibody-mediated enhancement of viral disease in a fetus or a neonate.

I. Anti-FcRn Antibodies

In general, the disclosure features isolated antibodies that bind to the human FcRn. An anti-FcRn antibody refers to an antibody that can bind to human FcRn and inhibit IgG (e.g., IgG autoantibodies or pathogenic antibodies) binding to FcRn. In some embodiments, the antibody is a monoclonal antibody. In other embodiments, the antibody is a polyclonal antibody. In some embodiment, the antibody is IgG1. In some embodiment, the antibody includes a λ light chain. In some embodiment, the antibody is a sialylated antibody. In some embodiments, the antibody is selected from the group consisting of a chimeric antibody, an affinity matured antibody, a humanized antibody, and a human antibody. In certain embodiments, the antibody is an antibody fragment, e.g., a Fab, Fab', Fab'-SH, $F(ab')_2$, or scFv.

In some embodiments, the antibody is a chimeric antibody. For example, an antibody contains antigen binding sequences from a non-human donor grafted to a heterologous non-human, human, or humanized sequence (e.g., framework and/or constant domain sequences). In one embodiment, the non-human donor is a mouse. In another embodiment, an antigen binding sequence is synthetic, e.g., obtained by mutagenesis (e.g., phage display screening, etc.). In a further embodiment, a chimeric antibody has non-human (e.g., mouse) variable regions and human constant regions. In one example, a mouse light chain variable region is fused to a human K light chain. In another example, a mouse heavy chain variable region is fused to a human IgG1 constant region.

In some embodiments, when describing the CDR sequences of an antibody, the antibody is defined as including a set of 6 CDR sequences. Including a set of CDR sequences describes an antibody that consists of, comprises, or consists essentially of these CDR sequences.

In one aspect, the disclosure features an isolated antibody that binds to human neonatal Fc receptor (FcRn), the isolated antibody including: (1) a light chain variable region including a CDR L1, a CDR L2, and a CDR L3 and (2) a heavy chain variable region comprising a CDR H1, a CDR H2, and a CDR H3, wherein the CDR L1 includes the sequence SDVGSYNL (SEQ ID NO: 33) or VG_YNL (SEQ ID NO: 34), wherein the "_" can be any amino acid, the CDR L2 includes the sequence GDSE (SEQ ID NO: 35), the CDR L3 includes the sequence YAGSGIY (SEQ ID NO: 36), the CDR H1 includes the sequence TYA (SEQ ID NO:

37), the CDR H2 includes the sequence SIGASGSQTR (SEQ ID NO: 38) or SI_AS_SQ_R (SEQ ID NO: 39), wherein the "_" can be any amino acid, and the CDR H3 includes the sequence LAI (SEQ ID NO: 40), and, optionally, wherein (a) the CDR L1 has a deletion or has more than two amino acid substitutions relative to the sequence of TGTGSDVGSYNLVS (SEQ ID NO: 1), (b) the CDR L2 has a deletion or has more than one amino acid substitution relative to the sequence of GDSERPS (SEQ ID NO: 2), (c) the CDR L3 has a deletion or has more than one amino acid substitution relative to the sequence of SSYAGSGIYV (SEQ ID NO: 3), (d) the CDR H1 has a deletion or has more than one amino acid substitution relative to each of the sequences of TYAMG (SEQ ID NO: 4), DYAMG (SEQ ID NO: 5), and NYAMG (SEQ ID NO: 6), (e) the CDR H2 has a deletion or has more than two amino acid substitutions relative to each of the sequences of SIGSSGAQTRYADS (SEQ ID NO: 7), SIGASGSQTRYADS (SEQ ID NO: 8), SIGASGAQTRYADS (SEQ ID NO: 9), and SIGASGGOT-RYADS (SEQ ID NO: 10), or (f) the CDR H3 has a deletion or has more than one amino acid substitutions relative to the sequence of LAIGDSY (SEQ ID NO: 11). In some embodiments, the isolated antibody comprises the amino acid sequence KSG at Kabat positions 66-68.

In another aspect, the disclosure features an isolated antibody that binds to human FcRn, wherein the antibody binds to an epitope on FcRn comprising at least one, two, three, four, five, six, seven, eight, nine, ten, eleven, twelve, thirteen, fourteen, fifteen, sixteen, seventeen, eighteen, nineteen, or twenty amino acids selected from the group consisting of K80, A81, L82, G83, G84, K85, G86, P87, Y88, L112, N113, E115, G129, D130, W131, P132, E133, L135, A136, and Q139 of SEQ ID NO: 30, which corresponds to amino acids K103, A104, L105, G106, G107, K108, G109, P110, Y111, L135, N136, E138, G152, D153, W154, P155, E156, L158, A159, 0162, respectively, of wildtype FcRn. In some embodiments, the epitope on FcRn does not comprise E115, which corresponds to amino acid E138 of wildtype FcRn.

In another aspect, the disclosure features an isolated antibody that binds to an epitope on 02-microglobulin comprising at least one amino acid selected from the group consisting of 121, Q22, P52, and V105.

In another aspect, the disclosure features an isolated antibody that binds to FcRn, wherein the antibody binds to: (a) at least one amino acid of the sequence of KQGTWGGDWPEAL (SEQ ID NO: 25); and (b) a at least one amino acid of the sequence of FKALGGKGPYTL (SEQ ID NO: 26), wherein the antibody inhibits the binding of IgG to human FcRn.

The disclosure also features an isolated antibody that binds to human FcRn, wherein the antibody binds to at least one amino acid of the sequence of KQGTWGGDWPEAL (SEQ ID NO: 25), wherein the antibody binds to at least one of amino acid residues 5, 12, or 13 of SEQ ID NO: 25, and wherein the antibody inhibits the binding of IgG to human FcRn.

The disclosure also features an isolated antibody that binds to human FcRn, wherein the antibody binds to at least one amino acid of the sequence of KQGTWGGDWPEAL (SEQ ID NO: 25), wherein the antibody does not bind to a peptide consisting of the sequence EFMNFDLKQGT (SEQ ID NO: 27) or the sequence of EEFMNFDL (SEQ ID NO: 28), and wherein the antibody inhibits the binding of IgG to human FcRn.

In some embodiments, the anti-FcRn antibody described herein binds to at least one amino acid of the sequence of WGGDWPEAL (SEQ ID NO: 29). In some embodiments, the anti-FcRn antibody binds to at least amino acid residue 5 of SEQ ID NO: 25. In some embodiments, the anti-FcRn antibody binds to at least amino acid residue 12 of SEQ ID NO: 25. In some embodiments, the anti-FcRn antibody binds at least amino acid residue 13 of SEQ ID NO: 25.

In some embodiments, the anti-FcRn antibody binds to at least one amino acid of the sequence of FKALGGKGPYTL (SEQ ID NO: 26). The anti-FcRn antibody may also bind to t least two amino acids of the sequence of FKAL-GGKGPYTL (SEQ ID NO: 26).

In another aspect, the disclosure also features an isolated antibody that binds to human FcRn, wherein the antibody binds to at least one amino acid of the sequence of FKAL-GGKGPYTL (SEQ ID NO: 26), and wherein the antibody inhibits the binding of IgG to human FcRn.

In some embodiments of this aspect, the anti-FcRn antibody binds to at least two amino acids of the sequence of FKALGGKGPYTL (SEQ ID NO: 26). In some embodiments, the anti-FcRn antibody further binds to at least one amino acid of the sequence of KQGTWGGDWPEAL (SEQ ID NO: 25). In some embodiments, the anti-FcRn antibody further binds to at least two amino acids of the sequence of KQGTWGGDWPEAL (SEQ ID NO: 25). In some embodiments, the anti-FcRn antibody binds to at least one of amino acid residues 5, 12, or 13 of SEQ ID NO: 25. In some embodiments, the anti-FcRn antibody binds to at least amino acid residue 5 of SEQ ID NO: 25. In some embodiments, the anti-FcRn antibody binds to at least amino acid residue 12 of SEQ ID NO: 25. In some embodiments, the anti-FcRn antibody binds to at least amino acid residue 13 of SEQ ID NO: 25.

In another aspect, the disclosure features an isolated antibody capable of binding to human FcRn. The isolated antibody contains: (1) a light chain variable region that includes a CDR L1, a CDR L2, and a CDR L3 and (2) a heavy chain variable region that includes a CDR H1, a CDR H2, and a CDR H3, wherein the CDR L1 has a sequence having at least 92% identity to the sequence of TGTGSDVGSYNLVS (SEQ ID NO: 1), the CDR L2 has a sequence having at least 85% identity to the sequence of GDSERPS (SEQ ID NO: 2), the CDR L3 has a sequence having at least 90% identity to the sequence of SSY-AGSGIYV (SEQ ID NO: 3), the CDR H1 has a sequence having at least 80% identity to the sequence of TYAMG (SEQ ID NO: 4), DYAMG (SEQ ID NO: 5), or NYAMG (SEQ ID NO: 6), the CDR H2 has a sequence having at least 92% identity to the sequence of SIGSSGAQTRYADS (SEQ ID NO: 7), SIGASGSQTRYADS (SEQ ID NO: 8), SIGASGAQTRYADS (SEQ ID NO: 9), SIGASGGQTRY-ADS (SEQ ID NO: 10), TIGSSGAQTRYADS (SEQ ID NO: 41), SIGASGSQTRYADS (SEQ ID NO: 42), TIGASGAOTRYADS (SEQ ID NO: 43), or TIGASGGQTRYADS (SEQ ID NO: 32), and the CDR H3 has a sequence having at least 85% identity to the sequence of LAIGDSY (SEQ ID NO: 11). In some embodiments, the antibody binds human FcRn with a $K_D$ of less than 200, 150, 100, 50, or 40 pM. In some embodiments, the antibody binds human FcRn with a $K_D$ that is less than or equal (e.g., loss than) to that of an antibody having the light chain variable region and heavy chain variable region of N022, N023, N024, N026, or N027, and further having the same Fc region as the antibody being compared.

In some embodiments, an isolated antibody has a CDR L1 that comprises, consists of, consists essentially of, or has the sequence of $X_1$GTGSDVGSYNX$_2$VS (SEQ ID NO: 12), a CDR L2 that comprises, consists of, consists essentially of, or has the sequence of GDX$_3$X$_4$RPS (SEQ ID NO: 13), a CDR L3 that comprises, consists of, consists essentially of, or has the sequence of X$_5$SYX$_6$GSGIYV (SEQ ID NO: 14), a CDR H1 that comprises, consists of, consists essentially of, or has the sequence of Z$_1$YAMG (SEQ ID NO: 15), a CDR H2 that comprises, consists of, consists essentially of, or has the sequence of Z$_7$IGZ$_2$SGZ$_3$QTZ$_4$YADS (SEQ ID NO: 16), and a CDR H3 that comprises, consists of, consists essentially of, or has the sequence of LAZ$_5$Z$_6$DSY (SEQ ID NO: 17), where X$_1$ is a polar or hydrophobic amino acid (e.g., preferably T, A, S, or I), X$_2$ is a hydrophobic amino acid (e.g., preferably L or 1), X$_3$ is a polar amino acid (e.g., preferably S, N, or T), X$_4$ is a polar or acidic amino acid (e.g., preferably Q, E, or N), X$_5$ is a polar or hydrophobic amino acid (e.g., preferably C, S, I, or Y), X$_6$ is a hydrophobic amino acid (e.g., preferably A or V), Z$_1$ is a polar or acidic amino acid (e.g., preferably E, T, D, or N), Z$_2$ is a polar or hydrophobic amino acid (e.g., preferably S or A), Z$_3$ is G, S, or A, Z$_4$ is a basic amino acid (e.g., preferably K or R), Z$_5$ is a hydrophobic or basic amino acid (e.g., preferably I, L, or H), Z$_6$ is G, S, D, Q, or H, and Z$_7$ is S or T, and where the antibody binds human FcRn with a K$_D$ of less than 200, 150, 100, 50, or 40 pM.

In other embodiments, an isolated antibody has a CDR L1 that has the sequence of TGTGSDVGSYNLVS (SEQ ID NO: 1), a CDR L2 that has the sequence of GDSERPS (SEQ ID NO: 2), a CDR L3 that has the sequence of SSY-AGSGIYV (SEQ ID NO: 3), a CDR N that has the sequence of Z$_1$YAMG (SEQ ID NO: 15), a CDR H2 that has the sequence of Z$_7$IGZ$_2$SGZ$_3$QTRYADS (SEQ ID NO: 18), and a CDR H3 that has the sequence of LAIGDSY (SEQ ID NO: 11), where Z$_1$ is T, D, or N, Z$_2$ is S or A, Z$_3$ is G, S or A, and Z$_7$ is S or T.

Table 1 shows the amino acid sequences of the light and heavy chain complementary determining regions (CDRs) of some exemplary anti-FcRn antibodies.

TABLE 1

| Anti-FcRn antibody | CDR L1 | CDR L2 | CDR L3 | CDR H1 | CDR H2 | CDR H3 |
|---|---|---|---|---|---|---|
| N022 | TGTG SDVG SYNL VS (SEQ ID NO: 1) | GDSE RPS (SEQ ID NO: 2) | SSYA GSGI YV (SEQ ID NO: 3) | TYAM G (SEQ ID NO: 4) | SIGS SGAQ TRYA DS (SEQ ID NO: 7) | LAIG DSY (SEQ ID NO: 11) |
| N023 | TGTG SDVG SYNL VS (SEQ ID NO: 1) | GDSE RPS (SEQ ID NO: 2) | SSYA GSGI YV (SEQ ID NO: 5) | DYAM G (SEQ ID NO: 4) | SIGA SGSQ TRYA DS (SEQ ID NO: 8) | LAIG DSY (SEQ ID NO: 11) |
| N024 | TGTG SDVG SYNL VS (SEQ ID NO: 1) | GDSE RPS (SEQ ID NO: 2) | SSYA GSGI YV (SEQ ID NO: 6) | NYAM G (SEQ ID NO: 4) | SIGA SGAQ TRYA DS (SEQ ID NO: 9) | LAIG DSY (SEQ ID NO: 11) |

TABLE 1-continued

| Anti-FcRn antibody | CDR L1 | CDR L2 | CDR L3 | CDR H1 | CDR H2 | CDR H3 |
|---|---|---|---|---|---|---|
| N026 | TGTG SDVG SYNL VS (SEQ ID NO: 1) | GDSE RPS (SEQ ID NO: 2) | SSYA GSGI YV (SEQ ID NO: 3) | TYAM G (SEQ ID NO: 4) | SIGA SGGG TRYA DS (SEQ ID NO: 10) | LAIG DSY (SEQ ID NO: 11) |
| N027 | TGTG SDVG SYNL VS (SEQ ID NO: 1) | GDSE RPS (SEQ ID NO: 2) | SSYA GSGI YV (SEQ ID NO: 3) | TYAM G (SEQ ID NO: 4) | SIGA SGSQ TRYA DS (SEQ ID NO: 8) | LAIG DSY (SEQ ID NO: 11) |

Table 2 shows the SEQ ID NOs of the light and heavy chain variable regions of these exemplary anti-FcRn antibodies.

TABLE 2

| Anti-FcRn antibody | Light Chain Variable Region | Heavy Chain Variable Region |
|---|---|---|
| N022 | SEQ ID NO: 19 | SEQ ID NO: 20 |
| N023 | | SEQ ID NO: 21 |
| N024 | | SEQ ID NO: 22 |
| N026 | | SEQ ID NO: 23 |
| N027 | | SEQ ID NO: 24 |

In some embodiments, the light chain variable region of an isolated antibody has a sequence having at least 90% identity to the sequence of

```
                              (SEC ID NO: 19)
QSALTQPASVSGSPGQSITISCTGTGSDVGSYNLV

SWYQQHPGKAPKLMIYGDSERPSGVSNRFSGSKSG

NTASLTISGLQAEDEADYYCSSYAGSGIYVFGTGT

KVTVLGQPKAAPSVTLFPPSSEELQANKATLVCLI

SDFYPGAVTVAWKADSSPVKAGVETTTPSKQSNNK

YAASSYLSLTPEQWKSHKSYSCQVTHEGSTVEKTV

APTECS.
```

In some embodiments, the heavy chain variable region of an isolated antibody has a sequence having at least 90% identity to the sequence of

```
                              (SEQ ID NO: 20)
EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS
```

-continued

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In some embodiments, the heavy chain variable region of an isolated antibody has a sequence having at least 90% identity to the sequence of (SEQ ID NO: 21)

EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In some embodiments, the heavy chain variable region of an isolated antibody has a sequence having at least 90% identity to the sequence of (SEQ ID NO: 22)

EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In other embodiments, the heavy chain variable region of an isolated antibody has a sequence having at least 90% identity to the sequence of (SEQ ID NO: 23)

EVQLLESGGGLVQPGGSLRLSCAASGFTFSTYAMG

WVRQAPGKGLEWVSSIGASGGQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTQVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

In yet other embodiments, the heavy chain variable region of an isolated antibody has a sequence having at least 90% a identity to the sequence of (SEQ ID NO: 24)

EVQLLESGGGLVQPGGSLRLSCAASGFTFSTYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

The disclosure features an isolated antibody including a light chain variable region and a heavy chain variable region, where the light chain variable region has a sequence having at least 90% identity to the sequence of QSALTQPASVSGSPGQSITISCTGTGSDVGSYN-LVSWYQQHPGKAPKLMIYGDSERPSGVSNRFSGSKS GNTASLTISGLOAEDEADYYCSSYAGSGIYVFGTG-TKVTVLGQPKAAPSVTLFPPSSEELQANKATLVCLI SDFYPGAVTVAWKADSSPVKAGVETTTPSKQSN-NKYAASSYLSLTPEQWKSHKSYSCQVTHEOSTVEK TVAPTECS (SEQ ID NO: 19); and the heavy chain variable region has a sequence having at least 90% identity to the sequence of

```
                                    (SEQ ID NO: 20)
EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

The disclosure features an isolated antibody including a light chain variable region and a heavy chain variable region, where the light chain variable region has a sequence having at least 90% identity to the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVF-GTGTKVTVLGQPKAAPSVTLFPPSSEELQANKA-TLVCLI SDFYPGAVTVAWKADSSPVKAGVETTTP-SKQSNNKYAASSYLSLTPEQWKSHKSYSCQVTHEG-STVEK TVAPTECS (SEQ ID NO: 19); and the heavy chain variable region has a sequence having at least 90% identity to the sequence of

```
                                    (SEQ ID NO: 21)
EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

The disclosure features an isolated antibody including a light chain variable region and a heavy chain variable region, where the light chain variable region has a sequence having at least 90% identity to the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIV-VFGTGTKVTVLGQPKAAPSVTLFPPSSEELQANK- ATLVCLI SDFYPGAVTVAWKADSSPVKAGVETTTP-SKQSNNKYAASSYLSLTPEQWKSHKSYSCQVTHEG-STVEK TVAPTECS (SEQ ID NO: 19); and the heavy chain variable region has a sequence having at least 90% identity to the sequence of

```
                                    (SEQ ID NO: 22)
EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTQVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

The disclosure features an isolated antibody including a light chain variable region and a heavy chain variable region, where the light chain variable region has a sequence having at least 90% identity to the sequence of QSALTQPASVSGSPGQSITISCTGTGSDVGSYN-LVSWYQQHPGKAPKLMIYGDSERPSGVSNRFSGSKS GNTASLTISGLQAEDEADYYCSSYAGSGIYVFGT-GTGTKVTVLGQPKAAPSVTLFPPSSEELQANKATLVCLI SDFYPGAVTVAWKADSSPVKAGVETTTPSKQSN-NKYAASSVLSLTPEQWKSHKSVSCQVTHEGSTVEK TVAPTECS (SEQ ID NO: 19); and the heavy chain variable region has a sequence having at least 90% identity to the sequence of

```
                                    (SEQ ID NO: 23)
EVQLLESGGGLVQPGGSLRLSCAASGFTFSTYAMG

WVRQAPGKGLEWVSSIGASGGQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

The disclosure features an isolated antibody including a light chain variable region and a heavy chain variable region, where the light chain variable region has a sequence having at least 90% identity to the sequence of QSALTQPASVSGSPGQSITISCTGTGSDVGSYN-LVSWYQQHPGKAPKLMIYGDSERPSGVSNRFSGSKS GNTASLTISGLQAEDEADYVCSSYAGSGIYVFG-TGTKVTVLGQPKAAPSVTLFPPSSEELQANK-ATLVCLI SDFYPGAVTVAWKADSSPVKAGVETTTP-SKQSNNKYAASSYLSLTPEQWKSHKSYSCQVTHEG-STVEK TVAPTECS (SEQ ID NO: 19); and the heavy chain variable region has a sequence having at least 90%/identity to the sequence of

```
                                        (SEQ ID NO: 24)
EVQLLESGGGLVQPGGSLRLSCAASGFTFSTYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

Furthermore, in any of the anti-FcRn antibodies described herein, the heavy chain variable region of the antibody has a sequence having at least 95%, 97%, 99%, or 100% identity to the sequence of any one of SEQ ID NOs: 20-24. In any of the anti-FcRn antibodies described herein, the light chain variable region has a sequence having at least 95%, 97%, 99%, or 100% identity to the sequence of SEQ ID NO: 19.

The antibodies may further contain amino acid substitutions, additions, and/or deletions outside of the CDRs (i.e., in framework regions (FRs)). An amino acid substitution, addition, and/or deletion can be a substitution, addition, and/or deletion of one or more amino acids (e.g., 1, 2, 3, 4, 5, 6, 7, 8, or more). An amino acid substitution, addition, and/or deletion can be a substitution, addition, and/or deletion of eight or fewer, seven or fewer, six or fewer, five or fewer, four or fewer, three or fewer, or two or tower single amino acids. In some embodiments, the antibodies may further include any one or more of the following amino acid substitutions: A23V, S30R, L80V, A84T, E85D, A93V, relative to the sequence of any one of SEQ ID NOs: 20-24, and Q38H, V581, and G99D, relative to the sequence of SEQ ID NO: 19.

In some embodiments, the antibodies may include amino acid substitutions, additions, and/or deletions in the constant regions (e.g., Fc region) of the antibody that, e.g., lead to decreased effector function, e.g., decreased complement-dependent cytolysis (CDC), antibody-dependent cell-mediated cytolysis (ADCC), and/or antibody-dependent cell-mediated phagocytosis (ADCP), and/or decreased B-cell killing. The constant regions are not involved directly in binding an antibody to its target, but exhibit various effector functions, such as participation of the antibody in antibody-dependent cellular toxicity. In some embodiments, the antibodies are characterized by decreased binding (i.e., absence of binding) to human complement factor C1q and/or human Fc receptor on natural killer (NK) cells. In other embodiments, the antibodies are characterized by decreased binding (i.e., absence of binding) to human FcγRI, FcγRIIA, and/or FcγRIIIA. To alter or reduce an antibody-dependent effector function, such as CDC, ADCC, ADCP, and/or B-cell killing, antibodies may be of the IgG class and contain one or more amino acid substitutions E233, L234, G236, D265, D270, N297, E318, K320, K322, A327, A330, P331, and/or P329 (numbering according to the EU index of Kabat (Sequences of Proteins of Immunological Interest, 5th Ed. Public Health Service, National Institutes of Health, Bethesda, MD (1991))). In some embodiments, the antibodies contain the mutations L234A/L235A or D265A/N297A. Preferably, an anti-FcRn antibody contains amino acid substitution N297A, relative to the sequence of any one of SEQ ID NOs: 20-24, such that the antibody is changed to an aglycosylated form. The resulting effectorless antibody shows very little binding to complement or Fc receptors (i.e., complement C1q binding), indicating low CDC potential.

In other embodiments, the antibodies may include those having specific amino acid changes that improve stability of the antibody.

Moreover, in other embodiments, to minimize potential immunogenicity, some antibodies, e.g., N024, N026, and N027, may undergo an allotype change from G1m17.1 to G1m17 by substituting amino acids D355 and L357 (relative to the sequence of any one of SEQ ID NOs: 20-24) to glutamic acid and methionine, respectively.

In other embodiments, the antibodies, e.g., N022-N024, N026, and N027, do not contain a C-terminal lysine, e.g., a C-terminal lysine at residue 446 relative to the sequence of any one of SEQ ID NOs: 20-24.

The disclosure features an isolated antibody containing a light chain variable region and a heavy chain variable region, wherein the light chain variable region has the sequence of QSALTQPASVSGSPGQSITISCTGTGSD-VGSYNLVSWYQQHPGKAPKLMIYGDSERPSG-VSNRFSGSKS GNTASLTISGLQAEDEADYYCSSY-AGSGIYVFGTGTKVTVLGQPKAAPSVTLFPPS-SEELQANKATLVCLI SDFYPGAVTVAWKADSSPVK-AGVETTTPSKQSNNKYAASSYLSLTPEQWKSHKSY-SCQVTHEGSTVEK TVAPTECS (SEQ ID NO: 19); and the heavy chain variable region has the sequence of

```
                                        (SEQ ID NO: 20)
EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL
```

-continued

```
PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

The disclosure features an isolated antibody containing a light chain variable region and a heavy chain variable region, wherein the light chain variable region has the sequence of QSALTQPASVSGSPGQSITISCTGTGSD-VGSYNLVSWYQQHPGKAPKLMIYGDSERPSGVS-NRFSGSKS GNTASLTISGLQAEDEADVYCSSY-AGSGIYVFGTGTKVTVLGQPKAAPSVTLFPPS-SEELQANKATLVCLI SDFYPGAVTVAWKADSSPVK-AGVETTTPSKQSNNKYAASSYLSLTPEQWKSHKSYS-CQVTHEGSTVEK TVAPTECS (SEQ ID NO: 19); and the heavy chain variable region has the sequence of

```
                                      (SEQ ID NO: 21)
EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

The disclosure features an isolated antibody containing a light chain variable region and a heavy chain variable region, wherein the light chain variable region has the sequence of QSALTQPASVSGSPGQSITISCTGTGSD-VGSYNLVSWYQQHPGKAPKLMIYGDSERPSGV-SNRFSGSKS GNTASLTISGLQAEDEADYYCSSY-AGSGIYVFGTGTKVTVLGQPKAAPSVTLFPPS-SEELQANKATLVCLI SDFYPGAVTVAWKADSSPVK-AGVETTTPSKQSNNKYAASSYLSLTPEQWKSHKSY-SCOVTHEGSTVEK TVAPTECS (SEQ ID NO: 19); and the heavy chain variable region has the sequence of

```
                                      (SEQ ID NO: 22)
EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG
```

-continued

```
VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

The disclosure features an isolated antibody containing a light chain variable region and a heavy chain variable region, wherein the light chain variable region has the sequence of QSALTQPASVSGSPGQSITISCTGTGSD-VGSYNLVSWYQOHPGKAPKLMIYGDSERPSGVS-NRFSGSKS GNTASLTISGLQAEDEADYYCSSY-AGSGIYVFGTGTKVTVLGQPKAAPSVTLFPPS-SEELQANKATLVCLI SDFYPGAVTVAWKADSSPVK-AGVETTTPSKQSNNKYAASSYLSLTPEQWKSHKSYS-CQVTHEGSTVEK TVAPTECS (SEQ ID NO: 19); and the heavy chain variable region has the sequence of

```
                                      (SEQ ID NO: 23)
EVQLLESGGGLVQPGGSLRLSCAASGFTFSTYAMG

WVRQAPGKGLEWVSSIGASGGQTRYADSVKGRFTI

SRQNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTQVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

The disclosure features an isolated antibody containing a light chain variable region and a heavy chain variable region, wherein the light chain variable region has the sequence of QSALTQPASVSGSPGQSITISCTGTGSD-VGSYNLVSWYQQHPGKAPKLMIYGDSERPSGVS-NRFSGSKS GNTASLTISGLOAEDEADYYCSSY-AGSGIYVFGTGTKVTVLGQPKAAPSVTLFPPS-SEELQANKATLVCLI SDFYPGAVTVAWKADSSPVK-AGVETTTPSKQSNNKYAASSYLSLTPEQWKSHKSYS-CQVTHEGSTVEK TVAPTECS (SEQ ID NO: 19); and the heavy chain variable region has the sequence of

```
                                      (SEQ ID NO: 24)
EVQLLESGGGLVQPGGSLRLSCAASGFTFSTYAMG

WVRQAPGKGLEWVSSIGASGSQTRYADSVKGRFTI
```

-continued

```
SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.
```

In yet other embodiments, the antibodies are sialylated antibodies.

In any of the anti-FcRn antibodies described herein, in some embodiments, the antibody binds mouse or rat FcRn with a $K_D$ of less than 200, 150, 100, 50, or 40 pM.

In any of the anti-FcRn antibodies described herein, in some embodiments, the antibody binds to human FcRn with an affinity of between 1-100, 5-150, 5-100, 5-75, 5-50, 10-50, or 10-40 pM.

The anti-FcRn antibodies may be of immunoglobulin antibody isotype IgG, IgE, IgM, IgA, or IgD. Preferably, the anti-FcRn antibodies are of immunoglobulin antibody isotype IgG. The anti-FcRn antibodies may also be of any immunoglobulin antibody isotype subclasses. For example, the anti-FcRn antibodies may be of IgG subclass IgG1, IgG2, IgG3, or IgG4. Preferably, the anti-FcRn antibodies are of subclass IgG1. In particular, the anti-FcRn antibodies contain an IgG G1m17 or G1m17.1 allotype heavy chain. In some embodiments, the light chain of the andi-FcRn antibodies may be a K light chain, a λ light chain, or a κ-λ chimeric light chain. In preferred embodiments, the anti-FcRn antibodies contain a full-length λ light chain.

In some embodiments, the antibodies (e.g., N022-N024, N026, and N027, preferably N027 and/or N024) are monoclonal. The antibodies may also be polyclonal, chimeric, humanized or fully human. In some embodiments, the antibody may be affinity matured. In other embodiments, the antibody may be an antibody fragment.

Without being bound by theory, it is believed that the anti-FcRn antibodies compete with and inhibit the binding of IgG to human FcRn. Epitope mapping by hydrogen-deuterium exchange of the antibodies indicates that the antibodies bind to an epitope on FcRn located in and/or adjacent to the Fc-FcRn interaction interface, which suggests that the antibodies block IgG binding to FcRn by direction inhibition. Furthermore, the epitope-mapped binding site is distant from the albumin-binding site of FcRn.

In some embodiments, serum albumin binding is not inhibited. In some cases serum albumin levels are not decreased after anti-FcRn antibody administration.

II. Sialylated Anti-FcRn Antibodies

In some embodiments, the glycosylation site of the Fc region of anti-FcRn antibodies is at least 25%, 50%, 75% or more sialylated, on a mole basis. The antibodies may be sialylated with a sialyltransferase (ST6 Gal-I), which sialylates a substrate in an ordered fashion. Specifically, under certain conditions, ST6 sialyltransferase catalyzes addition of a sialic acid on the α1,3 arm of glycans on the Fc region of anti-FcRn antibodies, followed by addition of a second sialic acid on the α1,6 arm, followed by removal of sialic acid from the α1,3 arm.

Isolated anti-FcRn antibodies may be sialylated during production in the manufacturing host cells (e.g., mammalian cells, e.g., mammalian cells co-transfected with—or over-expressing—an ST6 sialyltransferase). In other embodiments, isolated anti-FcRn antibodies may be sialylated in vitro, post purification from the manufacturing host cell, e.g., enzymatically or through chemical conjugation. Methods of producing sialylated anti-FcRn antibodies are described in PCT Publication WO2014/179601.

III. FcRn Inhibition

Human neonatal Fc receptor (FcRn) is a type I transmembrane protein that functions as an IgG- and serum albumin-binding, intracellular-IgG trafficking protein. FcRn is expressed in endothelial cells, luminal epithelial cells, hepatocytes, podocytes, granulocytes, monocytes, macrophages, dendritic cells, and NK cells, but not on B or T cells. FcRn maintains the half-life of IgG by binding and trafficking constitutively internalized IgG back to the cell surface. Binding of both Fc and serum albumin by FcRn occurs in the early endosome at pH 6.0, followed by sorting of the FcRn into vesicles, which traffic the FcRn-bound IgG and/or albumin back to the cell surface where FcRn rapidly releases the IgG and/or albumin at pH 7.4. This trafficking cycle maintains the half-life of IgG and albumin by recycling both into the circulation and preventing trafficking to the lysosomes for degradation. FcRn also captures internalized IgG Fc in epithelial cells and transports them bidirectionally to the opposing apical or basolateral membranes. This function allows IgG to traffic to the lumen of organs such as the gastrointestinal tract or the transport of IgG or IgG-antigen complexes from the lumen to the vasculature or lymphoid tissues in the stromal layers.

In order to study the contribution of FcRn to IgG homeostasis, mice have been engineered so that parts of the light and heavy chains of FcRn have been "knocked out" so that these proteins are not expressed (Junghans et al., *Proc Nat Acad Sci USA* 93:5512, 1996). In these mice, the serum half-life and concentrations of IgG were dramatically reduced, suggesting an FcRn-dependent mechanism of IgG homeostasis. Studies in rodent models, such as the one discussed above, suggest that blockage of FcRn function can increase IgG catabolism, including that of pathogenic autoantibodies, thereby inhibiting disease (e.g., an autoimmune disease) development. FcRn may also contribute to antigen presentation through trafficking of immune complexes to antigen degradation and MHC loading compartments.

Placental transfer of maternal IgG antibodies to the fetus is an important FcRn-dependent mechanism that provides protection to the neonate while his/her humoral response is inefficient. During fetal life, FcRn in the syncytiotrophoblast layers of the placenta is responsible for the transfer of maternal IgG antibodies to the fetus. Pathogenic maternal antibodies (e.g., pathogenic maternal IgG antibodies) may also cross the placenta by binding to FcRn and cause alloimmune disorders and/or autoimmune disorders in the fetus and neonate. In some embodiments, pathogenic antibodies in the pregnant subject cause a fetal and neonatal alloimmune and/or autoimmune disorder in a fetus in the pregnant subject. The anti-FcRn antibodies described herein (e.g., N022-N024, N026, and N027, preferably N027 and/or N024) may compete with and inhibit the binding of maternal pathogenic antibodies (e.g., maternal pathogenic IgG antibodies) to FcRn, thereby increasing the catabolism and decreasing the half-life of these pathogenic antibodies.

The present disclosure provides isolated anti-FcRn antibodies that bind to human FcRn. The anti-FcRn antibodies may compete with and inhibit the binding of other anti-FcRn antibodies (e.g., IgG, IgG autoantibodies) to FcRn, thereby increasing the catabolism and decreasing the half-life of other anti-FcRn antibodies (e.g., IgG, IgG autoantibodies). The anti-FcRn antibodies may be used in a method of treating or reducing immune complex-based activation of an immune response in a subject, such as an immune response caused by autoantibodies in an autoimmune disease. Reducing an immune response may be described as reducing an immune response relative to a subject who does not receive treatment (e.g., a control subject). The anti-FcRn antibodies may also be used in methods of decreasing pathogenic antibody transport (e.g., pathogenic maternal IgG antibody transport) across the placenta of a pregnant subject, increasing pathogenic antibody catabolism in a pregnant subject, and treating an antibody-mediated enhancement of viral disease in a fetus or a neonate by administering to a pregnant subject an isolated antibody that binds to human FcRn. Decreasing pathogenic antibody transport across the placenta of a pregnant subject, may be described as decreasing pathogenic antibody transport relative to a subject who does not receive treatment (e.g., a control subject).

IV. Vectors, Host Cells, and Antibody Production

The anti-FcRn antibodies can be produced from a host cell. A host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc.). The choice of nucleic acid vectors depends in part on the host cells to be used. Generally, preferred host cells are of either prokaryotic (e.g., bacterial) or eukaryotic (e.g., mammalian) origin.

Nucleic Acid Vector Construction and Host Cells

A nucleic acid sequence encoding the amino acid sequence of an anti-FcRn antibody may be prepared by a variety of methods known in the art. These methods include, but are not limited to, oligonucleotide-mediated (or site-directed) mutagenesis and PCR mutagenesis. A nucleic acid molecule encoding an anti-FcRn antibody may be obtained using standard techniques, e.g., gene synthesis. Alternatively, a nucleic acid molecule encoding a wild-typo anti-FcRn antibody may be mutated to contain specific amino acid substitutions using standard techniques in the art, e.g., QuikChange™ mutagenesis. Nucleic acid molecules can be synthesized using a nucleotide synthesizer or PCR techniques.

Nucleic acid sequences encoding anti-FcRn antibodies may be inserted into a vector capable of replicating and expressing the nucleic acid molecules in prokaryotic or eukaryotic host cells. Many vectors are available in the art and can be used. Each vector may contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In some embodiments, mammalian cells are used as host cells. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In other embodiments, E. coli cells are used as host cells. Examples of E. coli strains include, but are not limited to, E. coli 294 (ATCC® 31,446), E. coli λ 1776 (ATCC® 31,537, E. coli BL21 (DE3) (ATCC® BAA-1025), and E. coli RV308 (ATCC® 31,608). Different host cells have characteristic and specific mechanisms for the posttranslational processing and modification of protein products. Appropriate cell lines or host systems may be chosen to ensure the correct modification and processing of the anti-FcRn antibody expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols (Methods in Molecular Biology)*, Humana Press; 2nd ed. 2004 (Jul. 20, 2004) and Vladimir Voynov and Justin A. Caravella (eds.) *Therapeutic Proteins: Methods and Protocols (Methods in Molecular Biology)* Humana Press; 2nd ed. 2012 (Jun. 28, 2012).

Protein Production, Recovery, and Purification

Host cells used to produce the anti-FcRn antibodies may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and CO$_2$ levels, such as 5 to 10% (preferably 8%). The pH of the medium is generally from about 6.8 to 7.4, e.g., 7.0, depending mainly on the host organism. If an inducible promoter is used in the expression vector, protein expression is induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified. An anti-FcRn antibody may be purified by any method known in the art of protein purification, for example, by protein A affinity, other chromatography (e.g., ion exchange, affinity, and size-exclusion column chromatography), centrifugation, differential solubility, or by any other standard technique for the purification of proteins. (see *Process Scale Purification of Antibodies*, Uwe Gottschalk (ed.) John Wiley & Sons, Inc., 2009). In some instances, an anti-FcRn antibody can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from the influenza hemagglutinin protein.

Alternatively, anti-FcRn antibodies can be produced by the cells of a subject (e.g., a human), e.g., in the context of therapy, by administrating a vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding the anti-FcRn antibody. The vector, once inside a cell of the subject (e.g., by transformation, transfection, electroporation, calcium phosphate precipitation, direct microinjection, infection, etc.) will promote expression of the anti-FcRn antibody, which is then secreted from the cell. If treatment of a disease or disorder is the desired outcome, no further action may be required. If collection of the protein is desired, blood may be collected from the subject and the protein purified from the blood by methods known in the art.

V. Pharmaceutical Compositions and Preparations

The disclosure features pharmaceutical compositions that include one or more anti-FcRn antibodies described herein (e.g., N022-N024, N026, and N027, preferably N027 and/or N024). In some embodiments, pharmaceutical compositions contain one or more antibodies as the therapeutic proteins. In other embodiments, pharmaceutical compositions containing one or more antibodies may be used in combination with other agents (e.g., therapeutic biologics and/or small molecules) or compositions in a therapy. In addition to a therapeutically effective amount of the antibody, the pharmaceutical compositions may contain one or more pharmaceutically acceptable carriers or excipients, which can be formulated by methods known to those skilled in the art.

Acceptable carriers and excipients in the pharmaceutical compositions are nontoxic to recipients at the dosages and concentrations employed. Acceptable carriers and excipients may include buffers, antioxidants, preservatives, polymers, amino acids, and carbohydrates. Pharmaceutical compositions can be administered parenterally in the form of an injectable formulation. Pharmaceutical compositions for injection (i.e., intravenous injection) can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (2nd od.) Taylor & Francis Group, CRC Press (2006).

The pharmaceutical composition may be formed in a unit dose form as needed. The amount of active component, e.g., one or more anti-FcRn antibodies (e.g., N022-N024, N026, and N027, preferably N027 and/or N024), included in the pharmaceutical preparations is such that a suitable dose within the designated range is provided (e.g., a dose within the range of 0.01-500 mg/kg of body weight).

VI. Routes, Dosage, and Administration

Pharmaceutical compositions that contain one or more anti-FcRn antibodies described herein (e.g., N022-N024, N026, and N027, preferably N027 and/or N024) as the therapeutic proteins may be formulated for intravenous administration, parenteral administration, subcutaneous administration, intramuscular administration, intra-arterial administration, intrathecal administration, or intraperitoneal administration. In particular, intravenous administration is preferred. The pharmaceutical composition may also be formulated for, or administered via, oral, nasal, spray, aerosol, rectal, or vaginal administration. For injectable formulations, various effective pharmaceutical carriers are known in the art.

The dosage of the pharmaceutical compositions depends on factors including the route of administration, the disease to be treated, and physical characteristics, e.g., age, weight, general health, of the subject. Typically, the amount of an anti-FcRn antibody described herein (e.g., N022-N024, N026, and N027, preferably N027 and/or N024) contained within a single dose may be an amount that effectively prevents, delays, or treats the disease without inducing significant toxicity. A pharmaceutical composition may include a dosage of an anti-FcRn antibody ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 1 to about 100 mg/kg and, in a more specific embodiment, about 1 to about 50 mg/kg. The dosage may be adapted by the physician in accordance with conventional factors such as the extent of the disease and different parameters of the subject.

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., Intravenous dosage forms, subcutaneous dosage forms, and oral dosage forms (e.g., ingestible solutions, drug release capsules). Generally, therapeutic proteins are dosed at 1-100 mg/kg, e.g., 1-50 mg/kg. Pharmaceutical compositions that contain an anti-FcRn antibody described herein (e.g., N022-N024, N026, and N027, preferably N027 and/or N024) may be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines.

VII. Methods of Treatment and Indications

The blockade of human FcRn by anti-FcRn antibodies may be of therapeutic benefit in diseases that are driven by IgG autoantibodies. The ability of FcRn blockade to induce overall pathogenic antibody (e.g., an IgG antibody) catabolism and removal of multiple species of autoantibodies without perturbing serum albumin, small circulating metabolites, or lipoproteins offers a method to expand the utility and accessibility of an autoantibody removal strategy to patients with autoantibody-driven autoimmune disease pathology. While this disclosure is not bound by theory, the dominant mechanism of action of an anti-FcRn antibody may be to increase the catabolism of pathogenic autoantibodies in circulation and decrease autoantibody and immune complex deposition in affected tissues.

The pharmaceutical compositions and methods containing one or more anti-FcRn antibodies described herein (e.g., N022-N024, N026, and N027, preferably N027 and/or N024) are useful to promote catabolism and clearance of pathogenic antibodies, e.g., IgG and IgG autoantibodies in a subject, to reduce the immune response, e.g., to block immune complex-based activation of the immune response in a subject, and to treat immunological conditions or diseases in a subject. In particular, the pharmaceutical compositions and methods are useful to reduce or treat an immune complex-based activation of an acute or chronic immune response. The acute immune response may be activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura (ITP), autoimmune haemolytic anaemia (AIHA), immune neutropenia, dialated cardiomyopathy, and serum sickness. The chronic immune response may be activated by a medical condition selected from the group consisting of chronic inflammatory demyelinating polyneuropathy (CIDP), systemic lupus, a chronic form of a disorder indicated for acute treatment, reactive arthropathies, primary biliary cirrhosis, ulcerative colitis, and antineutrophil cytoplasmic antibody (ANCA)-associated vasculitis.

In some embodiments, the pharmaceutical compositions and methods are useful to decrease the risk of or decrease the risk of developing anemia in the fetus. In some embodiments, the pharmaceutical compositions and methods are useful to decrease or obviate the need for IUT (intrauterine transfusion). In some embodiments, the pharmaceutical compositions and methods are useful to decrease or obviate the need for antenatal PP+IVIg, postnatal transfusion, IVIg, and/or phototherapy. In some embodiments, the pharmaceutical compositions and methods are useful to reduce or treat an immune response activated by an autoimmune disease. The autoimmune disease may be selected from the group consisting of alopecia areata, ankylosing spondylitis, antiphospholipid syndrome, Addison's disease, hemolytic anemia, autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

In particular, the pharmaceutical compositions and methods are useful to reduce or treat an immune response activated by systemic lupus erythematosus, antiphospholipid syndrome, pemphigus vulgaris/bullous pemphigoid, antineutrophil cytoplasmic antibody (ANCA)-associated vasculitis, myasthenia gravis, or neuromyelitis optica.

The pharmaceutical compositions and methods are useful in methods of decreasing pathogenic antibody transport (e.g., pathogenic maternal IgG antibody transport) across the placenta of a pregnant subject, increasing pathogenic antibody catabolism in a pregnant subject, and treating an antibody-mediated enhancement of viral disease in a fetus or a neonate by administering to a pregnant subject an isolated antibody that binds to human FcRn. Diseases and disorders that may benefit from FcRn inhibition by the isolated anti-FcRn antibodies described herein (e.g., N022-N024, N026, and N027, preferably N027 and/or N024) include diseases and disorders in a fetus and/or neonate that are caused by the transfer of maternal pathogenic antibodies (e.g., maternal pathogenic IgG antibodies) across the placenta from a pregnant subject to the fetus and/or neonate.

In some embodiments, the diseases and disorders that may benefit from FcRn inhibition by the isolated anti-FcRn antibodies described herein (e.g., N022-N024, N026, and N027, preferably N027 and/or N024) are fetal and neonatal alloimmune and/or autoimmune disorders. Fetal and neonatal alloimmune disorders are disorders in a fetus and/or neonate that is caused by pathogenic antibodies in the pregnant subject. The pathogenic antibodies in the pregnant subject may attack the antigens of the fetus (e.g., antigens the fetus inherited from the fetus' father), causing the fetus or the neonate to have a fetal and neonatal alloimmune and/or autoimmune disorder.

Examples of fetal and neonatal alloimmune and/or autoimmune disorders that may be treated by the methods described herein include, but are not limited to, fetal and neonatal alloimmune thrombocytopenia (FNAIT), hemolytic disease of the fetus and newborn (HDFN), alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma. Behcet's disease, neonatal Graves' disease, neonatal Kawasaki disease, neonatal autoimmune thyroid disease, and neonatal type I diabetes mellitus.

In some embodiments, the diseases and disorders that may benefit from FcRn inhibition by the isolated anti-FcRn antibodies described herein (e.g., N022-N024, N026, and N027, preferably N027 and/or N024) are viral diseases wherein antibodies facilitate viral entry into host cells, leading to increased or enhanced infectivity in the cells, e.g., antibody-mediated enhancement of viral disease. In some embodiments, an antibody may bind to a viral surface protein and the antibody/virus complex may bind to an FcRn on a cell surface through interaction between the antibody and the receptor. Subsequently, the antibody/virus complex may get internalized into the cell. For example, a virus may gain entry into the cells and/or tissues of a fetus through forming a complex with a maternal IgG antibody. A maternal IgG antibody may bind to a viral surface protein and the IgG/virus complex may bind to an FcRn in the syncytiotrophoblasts of the placenta, which then transfers the complex into the fetus.

In some embodiments, the methods described herein may be used to treat an antibody-mediated enhancement of viral disease. In some embodiments, the viral diseases that are enhanced by pathogenic antibodies (e.g., pathogenic IgG antibodies) include, but are not limited to, viral diseases caused by an alpha virus infection, flavivirus infection, Zika virus infection, Chikungunya virus infection, Ross River virus infection, severe acute respiratory syndrome coronavirus infection, Middle East respiratory syndrome, avian influenza infection, influenza virus infection, human respiratory syncytial virus infection, Ebola virus infection, yellow fever virus infection, dengue virus infection, human immunodeficiency virus infection, respiratory syncytial virus infection, Hantavirus infection, Getah virus infection, Sindbis virus infection, Bunyamwera virus infection, West Nile virus infection, Japanese encephalitis virus B infection, rabbitpox virus infection, lactate dehydrogenase elevating virus infection, reovirus infection, rabies virus infection, foot-and-mouth disease virus infection, porcine reproductive and respiratory syndrome virus infection, simian hemorrhagic fever virus infection, equine infectious anemia virus infection, caprine arthritis virus infection, African swine fever virus infection, lentivirus infection, BK papovavirus infection, Murray Valley encephalitis virus infection, enterovirus infection, cytomegalovirus infection, pneumovirus infection, morbillivirus infection, and measles virus infection.

The blockade of human FcRn by anti-FcRn antibodies may be of therapeutic benefit in diseases that are driven by pathogenic antibodies (e.g., pathogenic IgG antibodies). The ability of FcRn blockade to induce overall pathogenic antibody catabolism and removal of multiple species of pathogenic antibodies without perturbing serum albumin, small circulating metabolites, or lipoproteins offers a method to expand the utility and accessibility of a pathogenic antibody removal strategy to patients with pathogenic antibody-driven autoimmune disease pathology. While not bound by theory, the dominant mechanism of action of an anti-FcRn antibody may be to increase the catabolism of pathogenic antibodies in circulation and decrease pathogenic antibody and immune complex deposition in affected tissues.

The anti-FcRn antibodies described heroin (e.g., N022-N024, N026, and N027, preferably N027 and/or N024) may be administered to a pregnant subject who has or is at risk of having a medical condition that activates an immune response in the pregnant subject. In some embodiments, the pregnant subject may have had, in the past, a medical condition that activated an immune response in the pregnant subject. In some embodiments, the pregnant subject has a history of having had a previous fetus or neonate that had a fetal and neonatal alloimmune and/or autoimmune disorder. In some embodiments, the anti-FcRn antibodies described herein may be administered to a pregnant subject if a pathogenic antibody associated with an immune disease is detected in a biological sample (e.g., a blood or urine sample) obtained from the pregnant subject. In some embodiments, the pathogenic antibody detected in the biological sample of the pregnant subject is known to bind to an antigen from the fetus in the pregnant subject (e.g., an antigen that the fetus inherited from the fetus' father).

In some embodiments, the anti-FcRn antibodies described herein (e.g., N022-N024, N026, and N027, preferably N027 and/or N024) may be administered to a subject who is planning to become pregnant and who has or is at risk of having a medical condition that activates an immune response in the pregnant subject, and/or who has had, in the past, a medical condition that activated an immune response in the pregnant subject. In some embodiments, a subject is planning to become pregnant and has a history of having had a previous fetus or neonate that had a fetal and neonatal alloimmune and/or autoimmune disorder. In some embodiments, the anti-FcRn antibodies described herein may be administered to a subject who is planning to become pregnant and whose biological sample contains a pathogenic antibody associated with an immune disease.

In some embodiments, the anti-FcRn antibodies described herein may be administered to a subject (e.g., a pregnant subject) to reduce or treat an immune complex-based activation of an acute or chronic immune response in the subject. The acute immune response may be activated by a medical condition (e.g., pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dialated cardiomyopathy, serum sickness, chronic inflammatory demyelinating polyneuropathy, systemic lupus, reactive arthropathies, primary biliary cirrhosis, ulcerative colitis, or antineutrophil cytoplasmic antibody (ANCA)-associated vasculitis).

In some embodiments, the anti-FcRn antibodies described herein may be administered to a subject (e.g., a pregnant subject) to reduce or treat an immune response activated by an autoimmune disease. The autoimmune disease may be, for example, alopecia areata, ankylosing spondylitis, antiphospholipid syndrome, Addison's disease, hemolytic anemia, warm autoimmune hemolytic anemia (wAIHA), anti-factor antibodies, heparin induced thrombocytopenia (HICT), sensitized transplant, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

EXAMPLES

Example 1—Antibody Production

IgG heavy and light chain nucleic acid molecules were cloned in vector pCDNA 3.3 using osteonectin secretion signals. HEK 293F cells were grown in Expi293 media at 37° C. with 8% $CO_2$. Cells were transfected at a density of $3\times10^6$/ml with 1 mg total DNA per liter. Enhancers were added on days 2 and 3 following manufacturer's directions and the cells were cultured until day 5 or 6 before cell viability dropped to below 50% to 60%. The cells were then spun out by centrifugation and the spent media was sterile filtered and stored at 4° C. until antibody purification. Antibodies were purified by a two-column procedure: POROS Protein A chromatography followed by POROS HS-50 cation exchange chromatography. The former separated most of the host cell proteins from the expressed antibodies while the latter removed the heavy chain dimers, light chain dimers, and half antibodies, as well as higher molecular weight species. The fractions from the HS-50 cation exchange column were pooled based on an SDS-PAGE gel analysis to maximize purity of the full-length antibodies. The collected fractions were put over a Sephadex G50 buffer exchange column equilibrated in PBS at pH 7.2. The peak fractions were pooled and concentrated to greater than 10 mg/ml using 30 kDa spin concentrators and frozen at −30° C. in 2 mg and 5 mg aliquots. The final protein samples were checked for purity by SDS-PAGE.

Example 2—Binding Affinities

Through affinity maturation, we identified more than 100 anti-FcRn antibodies having binding affinities to human FcRn with a $K_D$ in the sub-micromolar range. Five antibodies (N022-N024, N026, and N027) were selected for further characterization. Surface Plasmon Resonance (SPR) was used to determine the on- and off-rates ($k_a$ and $k_d$, respectively) for each of these five antibodies. Briefly, a Bio-Rad GLC sensor chip was inserted into the ProteOn XPR 36 and air initialized. After initialization the running buffer was switched to freshly prepared buffer, either HBSP+ (0.01 M HEPES, 0.15 M NaCl, 0.05% P20, pH 7.4) or Sodium Phosphate Buffer (0.02 M Sodium Phosphate, 0.15 M NaCl, 0.05% P20, pH 6.0) as appropriate, which was used for the remainder of the assay and for all dilutions. The chip was preconditioned using one injection each of 0.5% SDS, 50 mM NaOH and 10 mM HCl at 30 μl/min for 60 seconds (s). A mouse anti-Human Fc mAb from GE Healthcare (BR100839) was diluted to 10 μg/ml in 10 mM acetate buffer pH 5.0 and approximately 5,700 response units (RU) was immobilized using standard amine coupling chemistry in the horizontal orientation onto a GLC sensor chip. The anti-hFcRn mAbs to be tested were captured onto the surface in the vertical orientation, with the goal of immobilizing approximately 200 response units (RU) per interaction spot. The rhFcRn was diluted in a five-point three-fold dilution series starting at 1.25 μg/ml, leaving one lane as buffer-only for a double reference. The analyte was flowed across the sensor surface in the horizontal orientation at 100 μl/min for 240 s with a 3,600 s dissociation time. Regeneration was accomplished by injecting 3M $MgCl_2$ at 100 μl/min for 30 s in both the horizontal and vertical directions. These procedures were repeated for all ligands.

Data analysis was conducted using the ProteOn Manager software. Each interaction step was adjusted for the Y and X direction using the Auto Process tool, followed by interspot channel referencing to remove non-specific interactions and blank lane double referencing to remove assay drift. The data was fit using the Langmuir 1:1 kinetic model with a grouped Rmax. The $k_a$, $k_d$ and $K_D$ values obtained from ProteOn Manager in a single run were averaged and their percent CV was calculated in Microsoft Excel when the N was three or greater.

Table 3 shows that five anti-FcRn antibodies, N022, N023, N024, N026, and N027, all bind with high affinity to human FcRn at pH 7.4. The equilibrium dissociation constant, $K_D$, of the anti-FcRn antibodies ranged from 19.4 pM (N027) to 36.5 pM (N026) for binding to human FcRn at pH 7.4, 298K. Table 3 also shows the rapid on-rates and slow off-rates of the five anti-FcRn antibodies. At pH 7.4, 298K, the on-rates were in the range of $0.93\text{-}1.42\times10^6$ 1/Ms for binding to human FcRn. The off-rates were in the range of $2.31\text{-}4.44\times10^6$ 1/s.

TABLE 3

| | $k_a$ (1/Ms) | $k_d$ (1/s) | $K_D$ (M) | $R_{max}$ | Chi2 | $K_D$ (pM) |
|---|---|---|---|---|---|---|
| N022 | 1.42E+06 | 4.42E−05 | 3.10E−11 | 146.93 | 7.65 | 31 |
| N023 | 9.27E+05 | 2.91E−05 | 3.14E−11 | 193.43 | 5.26 | 31.4 |
| N024 | 1.13E+06 | 4.03E−05 | 3.55E−11 | 181.17 | 6.12 | 35.5 |

TABLE 3-continued

| | $k_a$ (1/Ms) | $k_d$ (1/s) | $K_D$ (M) | $R_{max}$ | Chi2 | $K_D$ (pM) |
|---|---|---|---|---|---|---|
| N026 | 1.22E+06 | 4.44E−05 | 3.65E−11 | 163.9 | 5.68 | 36.5 |
| N027 | 1.19E+06 | 2.31E−05 | 1.94E−11 | 211.33 | 7.81 | 19.4 |

Example 3—IgG Competition

Figure 1:
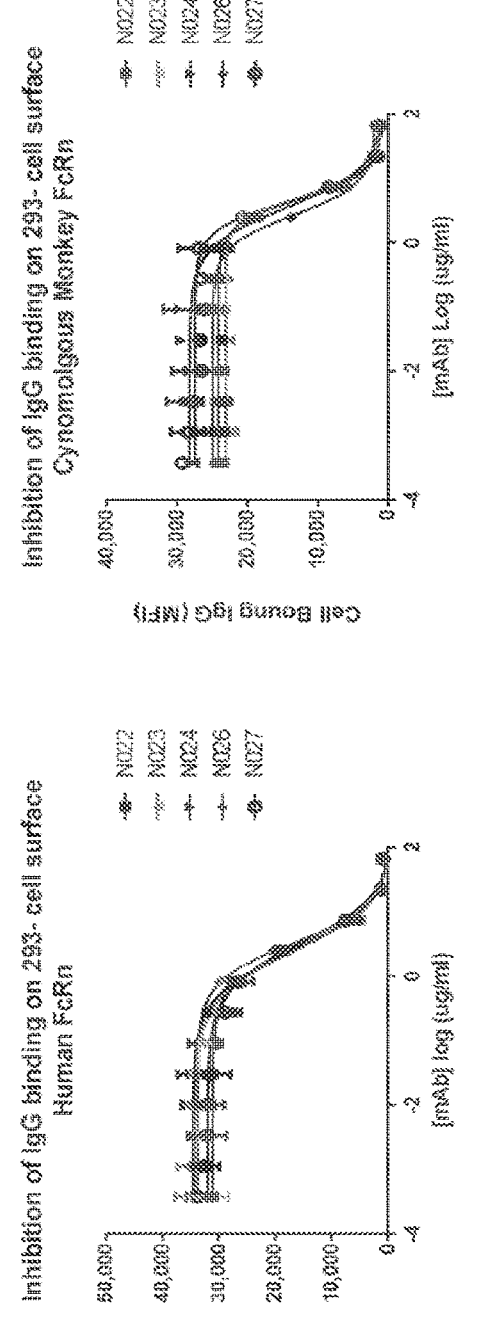
FIG. 1 shows two graphs and a table that show IgG competitive binding of antibodies N022-N024, N026, and N027 to human or cynomolgus monkey FcRn at pH 6.0.

The ability of anti-FcRn antibodies to compete with IgG for binding to human or cynomolgus monkey FcRn was evaluated on human embryonic kidney (HEK) 293 cells ectopically expressing cell surface, glycophosphatidylinositol (GPI)-linked FcRn. Human and cynomolgus monkey FcRn alpha amino acid sequences exhibit 97.5% sequence identity. Nine amino acid residues of 355 are different between human and cynomolgus monkey FcRn alpha, but none are in the epitope-mapped binding region. The level of cell-bound IgG was determined using 66 nM of fluorescent probe-labeled, non-specific IgG. The binding of IgG to cell surface FcRn was done at pH 6.0, which allows the Fc portion of IgG to interact with FcRn. As shown in FIG. 1, the amount of cell-bound IgG significantly decreased as the concentration of the anti-FcRn antibody (N022-N024, N026, or N027) increased. The binding of IgG was inhibited in a concentration- and saturation-dependent manner by each of the five exemplary anti-FcRn antibodies, demonstrating the ability of the anti-FcRn antibodies, N022-N024, N026, and N027, to effectively compete with and inhibit binding of IgG to FcRn at pH 6.0. The EC50 values of the antibodies ranged between 2 and 6 nM.

Example 4—Effect of Anti-FcRn Antibodies on IgG Catabolism in Mice

Figure 2:
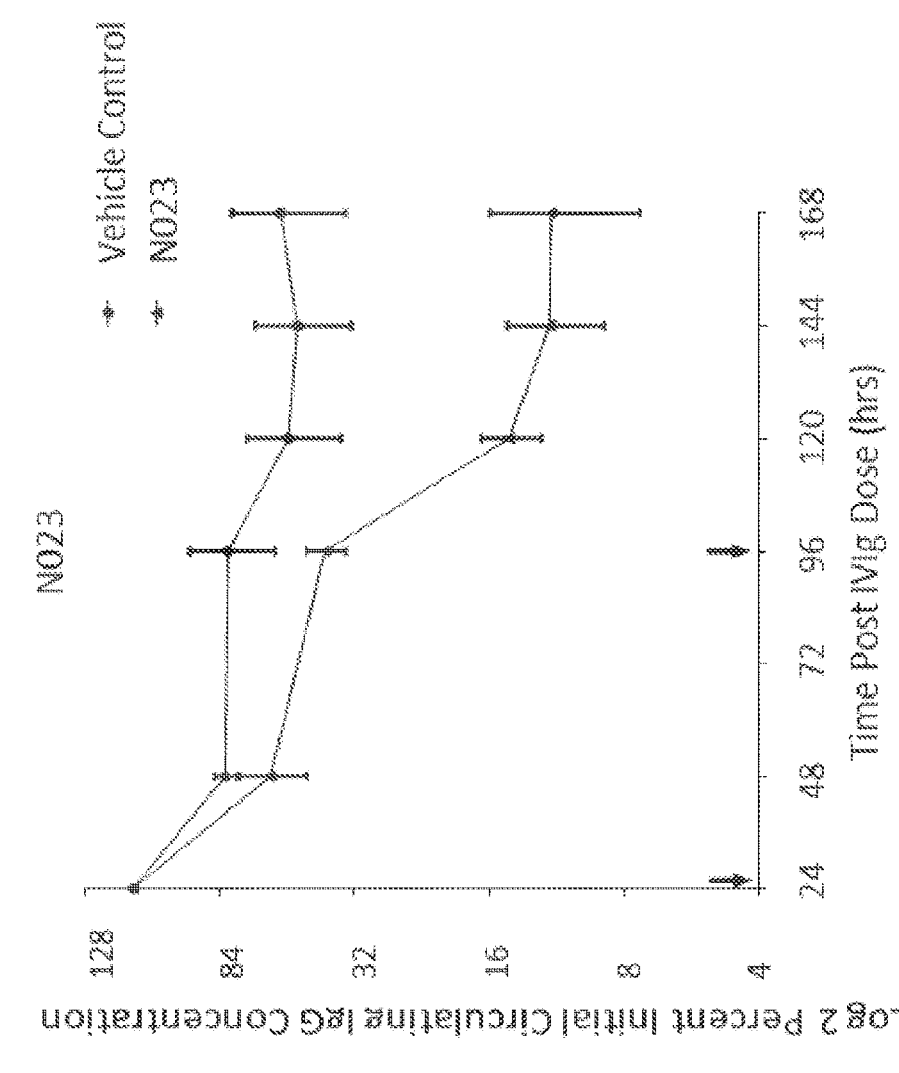
FIG. 2 shows graphs that show the effects of antibodies N023, N024, N026, and N027 on IgG catabolism in transgenic mice.

To measure the effect of the anti-FcRn antibodies on IgG catabolism in vivo, human FcRn transgenic mouse strain, homozygous B6.Cg-Fcgrt$^{tm1Dcr}$ Tg(FCGRT)32Dcr/DcrJ mice, which lacks mouse FcRn but expresses human FcRn in a tissue distribution similar to the endogenous mouse and human FcRn, was used. FcRn−/−hFcRn (32) Tg mice injected with 500 mg/kg human IVIG tracer on day 0 were administered a single dose of an anti-FcRn antibody at 10 mg/kg on days 1 and 4. As shown in FIG. 2, the catabolism of IgG was increased by the administration of anti-FcRn antibodies as seen by lower levels of IgG measured over time in anti-FcRn antibody-treated mice. The activities of N024 ($K_D$=35.5 pM), N026 ($K_D$=36.5 pM), and N027 ($K_D$=19.4 pM) appeared to be similar at 10 mg/kg.

Example 5—In Vitro Characterizations of Anti-FcRn Antibodies

Cellular binding affinities of the antibodies were measured on human embryonic kidney (HEK) 293 cells ectopically expressing cell surface, glycophosphatidylinositol (GPI)-linked human or cynomolgus monkey FcRn. FcRn is a type I transmembrane protein with the IgG and albumin binding domains oriented to the luminal side of endosomal membranes or to the cell surface when transported to the plasma membrane. The binding of anti-FcRn antibodies to cell surface, membrane-associated FcRn on HEK293 cells at pH 7.4 mimics binding in a physiologically-relevant environment and at the pH where only the Fab domain and not the Fc domain of the antibodies interact with FcRn. The FcRn extracellular domain was displayed on the cell surface at high density through a C-terminal engineered GPI linkage. The anti-FcRn antibodies were labeled with a fluorescent probe. The antibodies were allowed to bind for 30 minutes on ice. Cells were then washed at 4° C. and bound antibodies were detected using a fluorophore-labeled secondary antibody, e.g., a goat anti-human IgG F(ab)$_2$. The binding to human FcRn was concentration dependent and antibodies displayed EC50 values ranging from 4 to 7 nM.

Cellular binding affinities of the antibodies were also measured on endogenously expressed human FcRn. Monocytes express the highest levels of FcRn and show the highest percent positivity for FcRn expression in mouse and human blood. Monocytic cell line THP-1 was used to evaluate binding of anti-FcRn antibodies to endogenous human FcRn at pH 7.4. Since endogenous FcRn is primarily in intracellular endosomal vesicles, the THP-1 cells were first fixed and then permeablized with a mild detergent and fixed prior to incubation for 30 minutes at 4° C. with anti-FcRn antibodies in the presence of bovine serum to block non-specific Fc receptor binding. This assay was able to distinguish antibodies with better binding to endogenous human FcRn. The binding of anti-FcRn antibodies to THP-1 cells is concentration dependent. All antibodies, e.g., N022-N024, N026, and N027, showed better binding affinities than IgG1. Antibody N027 displayed the highest binding affinity with an EC50 value of 3.0 nM.

Figure 4A:
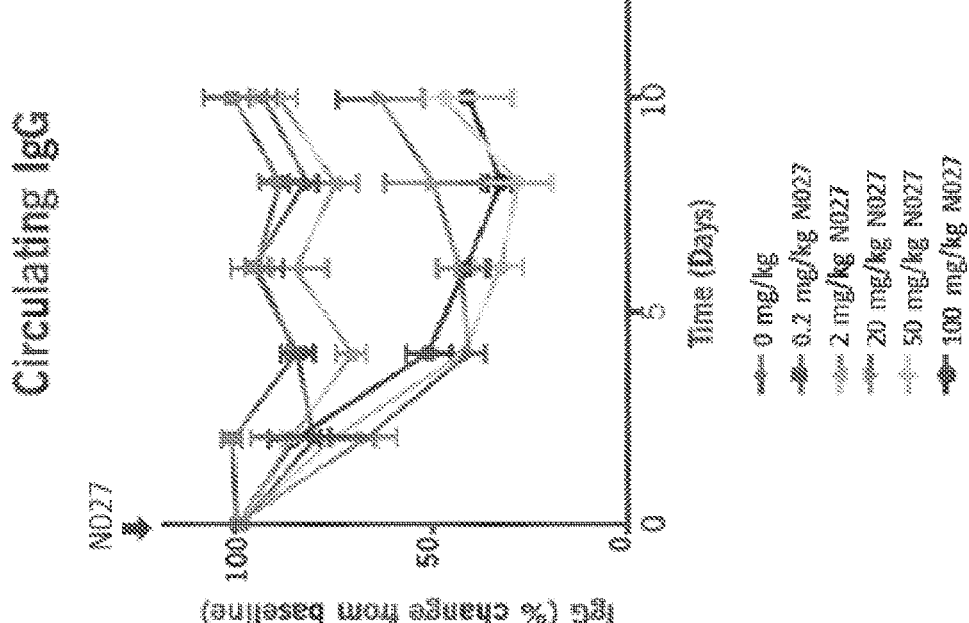
FIGS. 4A-4C show graphs that show the selective induction of IgG catabolism and target occupancy in cynomolgus monkeys following administration of different doses of antibody N027.
Figure 4B:
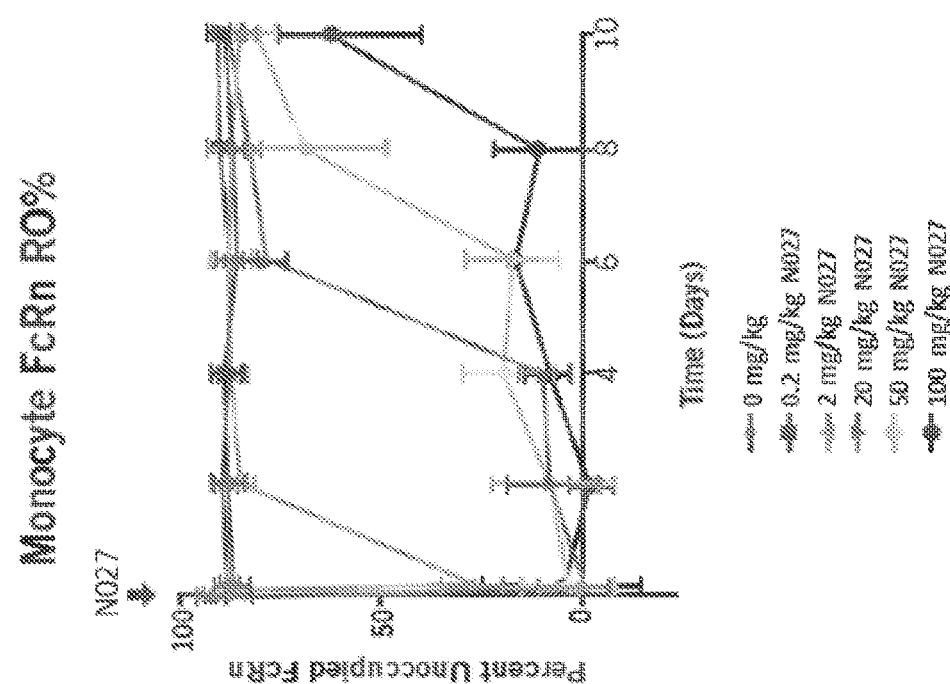
Figure 4C:
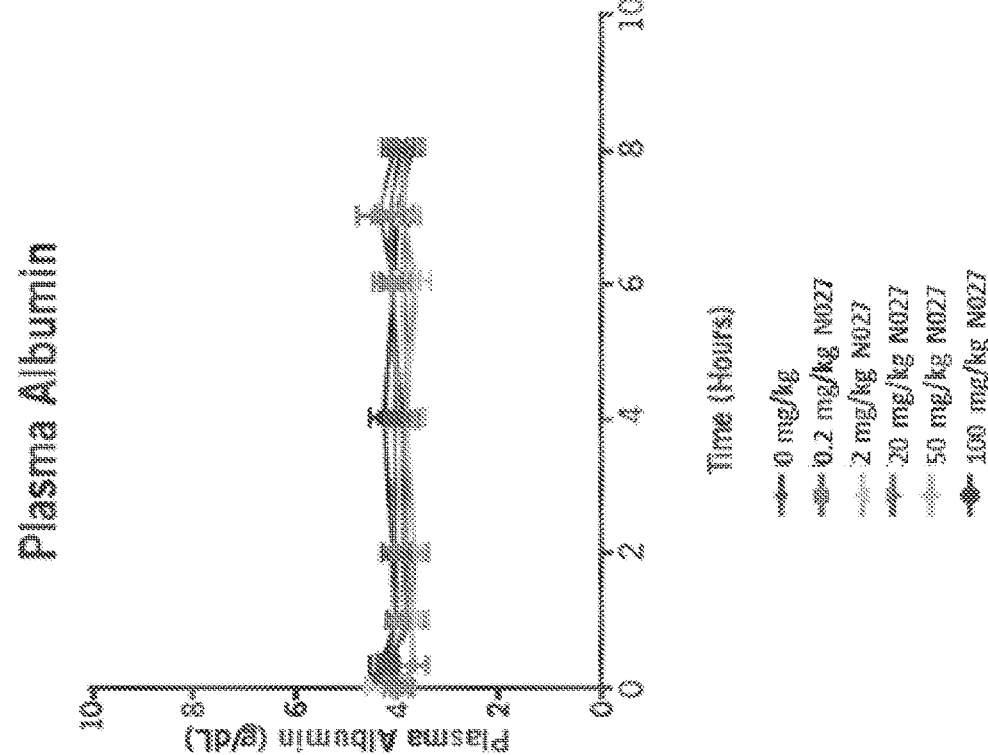

Epitope mapping by hydrogen-deuterium exchange of the antibodies indicated that the antibodies bind to an epitope that comprises at least a portion of two amino acid sequences on human FcRn. One amino acid sequence includes at least one amino acid of the sequence of KQGTWGGDWPEAL (SEQ ID NO: 25), located in and/or adjacent to the Fc-FcRn interaction interface, which suggests that the antibodies block IgG binding to FcRn by direction inhibition. The first amino acid sequence comprises W131 of FcRn (SEQ ID NO: 30). The second amino acid sequence includes at least one amino acid of the sequence of FKALGGKGPYTL (SEQ ID NO: 26). The second amino acid sequence comprises Y88 of FcRn (SEQ ID NO: 30). The epitope of the anti-FcRn antibody includes one or both of a) an amino acid sequence comprising W131 of FcRn and b) an amino acid sequence comprising Y88 of FcRn. In some embodiments, the epitope comprises at least a) an amino acid sequence comprising W131 of FcRn and b) an amino acid sequence comprising Y88 of FcRn. In some embodiments, the epitope comprises either a) an amino acid sequence comprising W131 of FcRn or b) an amino acid sequence comprising Y88 of FcRn. The epitope-mapped binding sites are distant from the albumin-binding site of FcRn. Thus, serum albumin-binding should not be inhibited and serum albumin levels should not be decreased. An enzyme-linked immunosorbent assay (ELISA) was used to confirm that the antibodies do not inhibit serum albumin binding to FcRn. Soluble His-tagged extracellular domain of human FcRn was bound to the plate surface and pre-incubated with increasing concentrations of anti-FcRn antibody at pH 6.0. Horseradish peroxidase (HRP)-conjugated human serum albumin was allowed to bind to the soluble, His-tagged FcRn. None of the antibodies inhibited albumin binding to FcRn. Furthermore, in vivo experimental evidence also showed that cynomolgus monkey albumin levels remained constant after anti-FcRn antibody administration, indicating that albumin recycling was not disturbed by antibody binding to FcRn (FIG. 4C).

Figure 3:
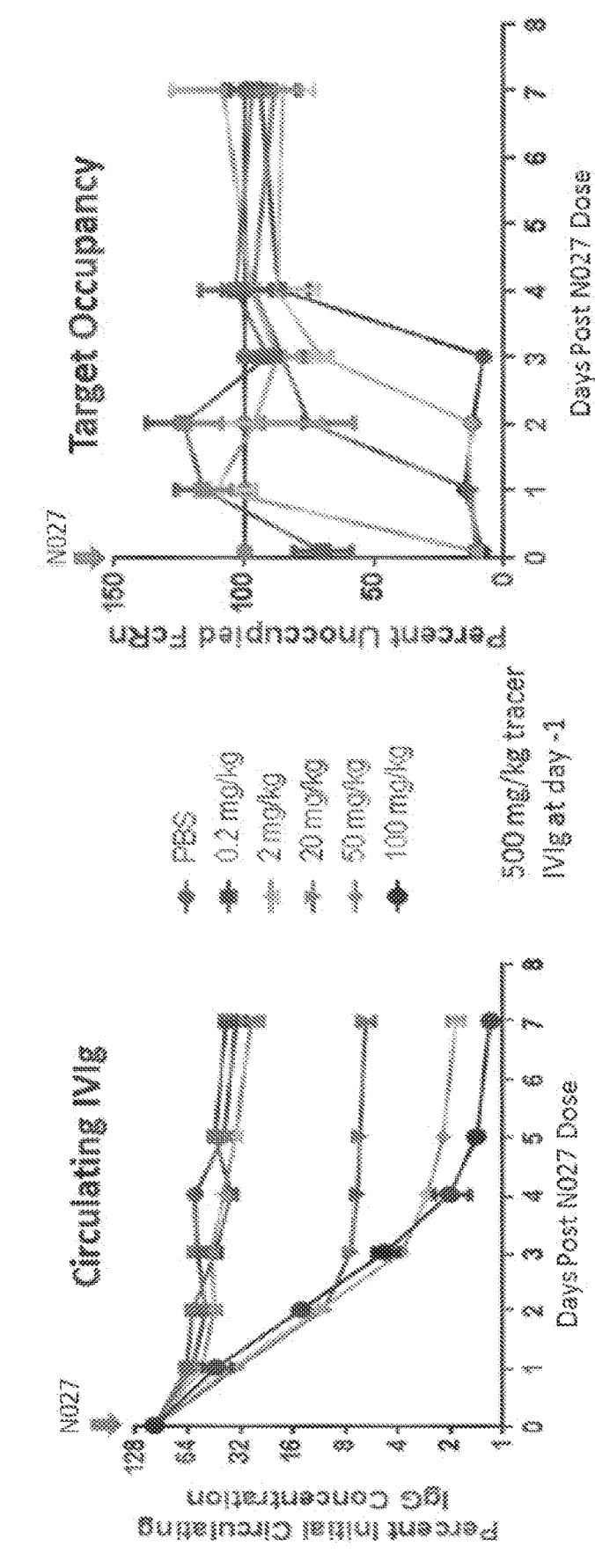
FIG. 3 shows graphs that show the dose-dependent effects of antibody N027 on IgG levels and target occupancy in transgenic mice.

Example 6—Effect of Anti-FcRn Antibodies on IgG Levels and Target Occupancy in Mice N027 was dosed intravenously (i.v.) 24 hrs after administration of 500 mg/kg human IVIg (tracer) to homozygous B6.Cg-Fcgrt$^{tm1Dcr}$Tg(FCGRT)32Dcr/DcrJ mice. Circulating human IgG was detected by ELISA on each day. Target occupancy was measured on each day in monocytes from RBC-lysed whole blood by fluorescence-activated cell sorting (FACS), after incubation of cells with immunophenotyping cell surface markers followed by fixation and permeabilization. Unoccupied FcRn was measured by staining with Dy650-labeled N027 (n=4 males per group). As shown in FIG. 3, IgG levels and the percentage of unoccupied FcRn were decreased by the administration of N027 in a dose-dependent manner.

Example 7—Selective Induction of IgG Catabolism and Target Occupancy in Cynomolgus Monkeys To study the effect of N027 on induction of IgG catabolism and target receptor occupancy, N027 was dosed i.v. on day 0 in cynomolgus monkeys. Circulating endogenous IgG and albumin was detected by ELISA. Target occupancy was measured in monocytes from RBC-lysed whole blood by FACS, after incubation of cells with immunophenotyping cell surface markers followed by fixation and permeabilization. Unoccupied FcRn was measured by staining with Dy650-labeled N027. (n=3 males per group). As shown in FIGS. 4A-4C, IgG level and the percentage of unoccupied FcRn were decreased by the administration of N027 in a dose-dependent manner, while plasma albumin levels stayed unchanged.

Example 8—Biodistribution of N027 in Mice

Figure 5:
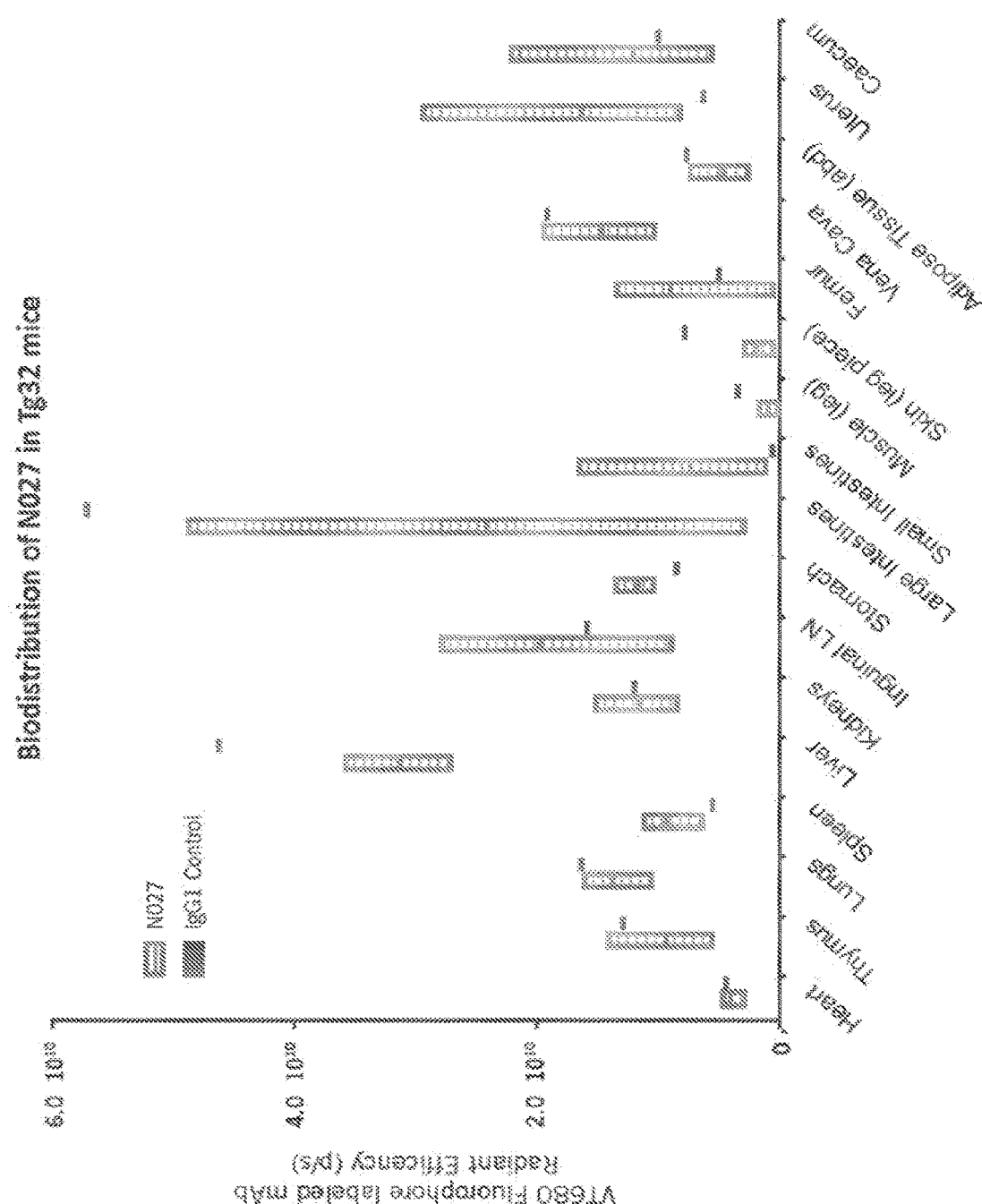
FIG. 5 shows a graph that shows the biodistribution of N027 in transgenic mice.

To compare the biodistribution of N027 and a human IgG with no target mediated distribution, N027 or human IgG1 isotype control antibody labeled with fluorophore (VivoTag 680) were administered i.v. to homozygous B6.Cg-Fcgt$^{tm1Dcr}$Tg(FCGRT)32Dcr/DcrJ mice at 30 mg/kg. Levels of labeled antibody were measured in individual organs by quantitative ex vivo fluorescence imaging. As shown in FIG. 5, the biodistribution of N027 in various organs in mice is similar to that of an isotype control antibody.

Example 9—Efficacy of N027 in Mouse Collagen Antibody-Induced Arthritis

Figure 6:
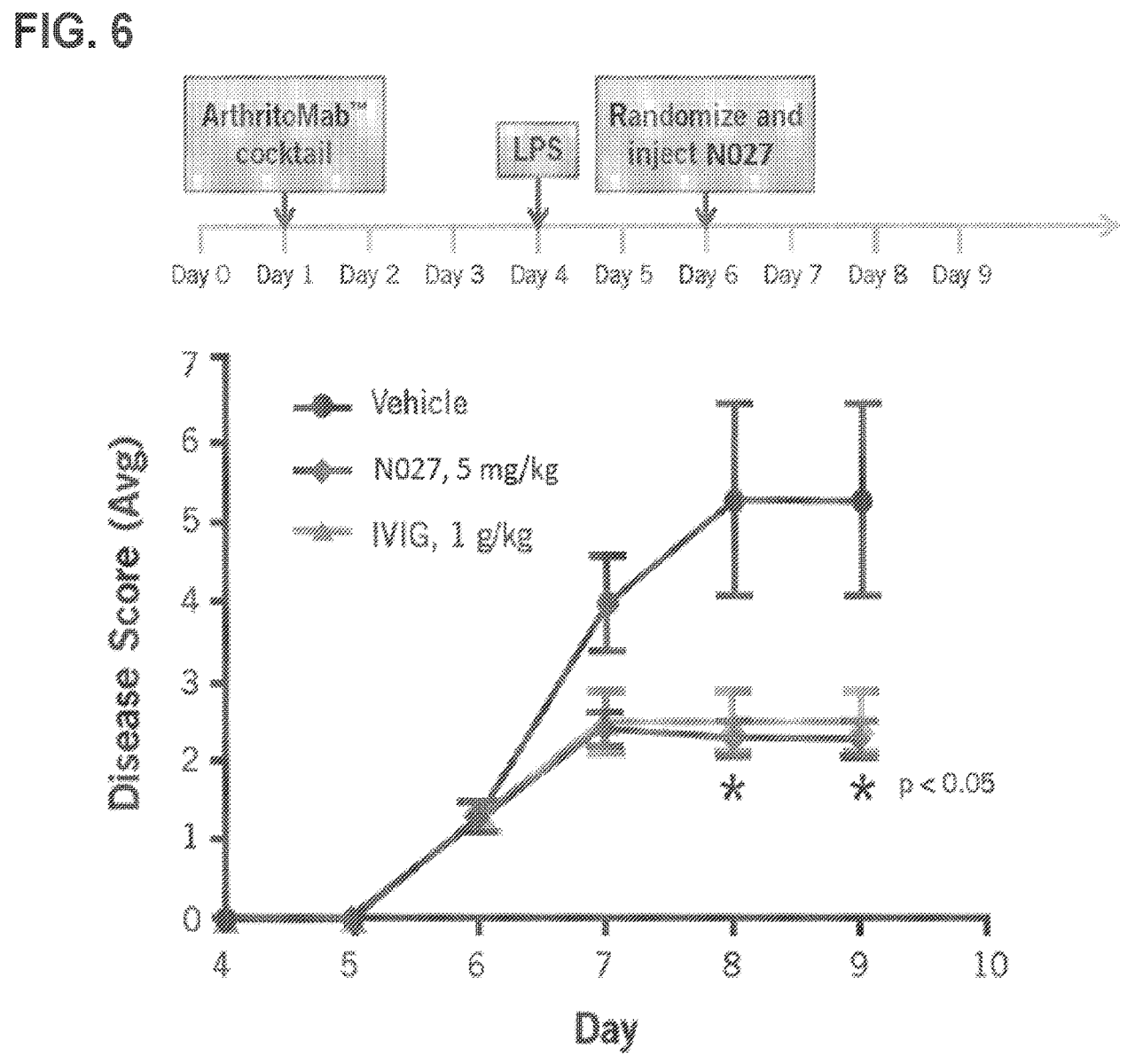

Collagen antibody-induced arthritis was induced in homozygous B6.Cg-Fcgrt$^{tm1Dcr}$Tg(FCGRT)32Dcr/DcrJ mice by intraperitoneal (i.p.) injection of ArthritoMab™ cocktail (MD Biosciences) on day 1 and inflammatory disease activity induced with 100 μg LPS dosed i.p. on day 4. N027 was dosed therapeutically i.v. at 5 mg/kg (arrow), on day 6 post disease induction and randomization. IVIG at 1 g/kg (positive control group) or vehicle-PBS (negative control) were dosed on day 6 after randomization (n=5 per group). As shown in FIG. 6, N027 potently inhibits collagen antibody-induced arthritis in human transgenic FcRn mice when dosed therapeutically.

Example 10—Efficacy of N027 in Mouse Chronic Idiopathic Thrombocytopenia Purpura (ITP)

Figure 7:
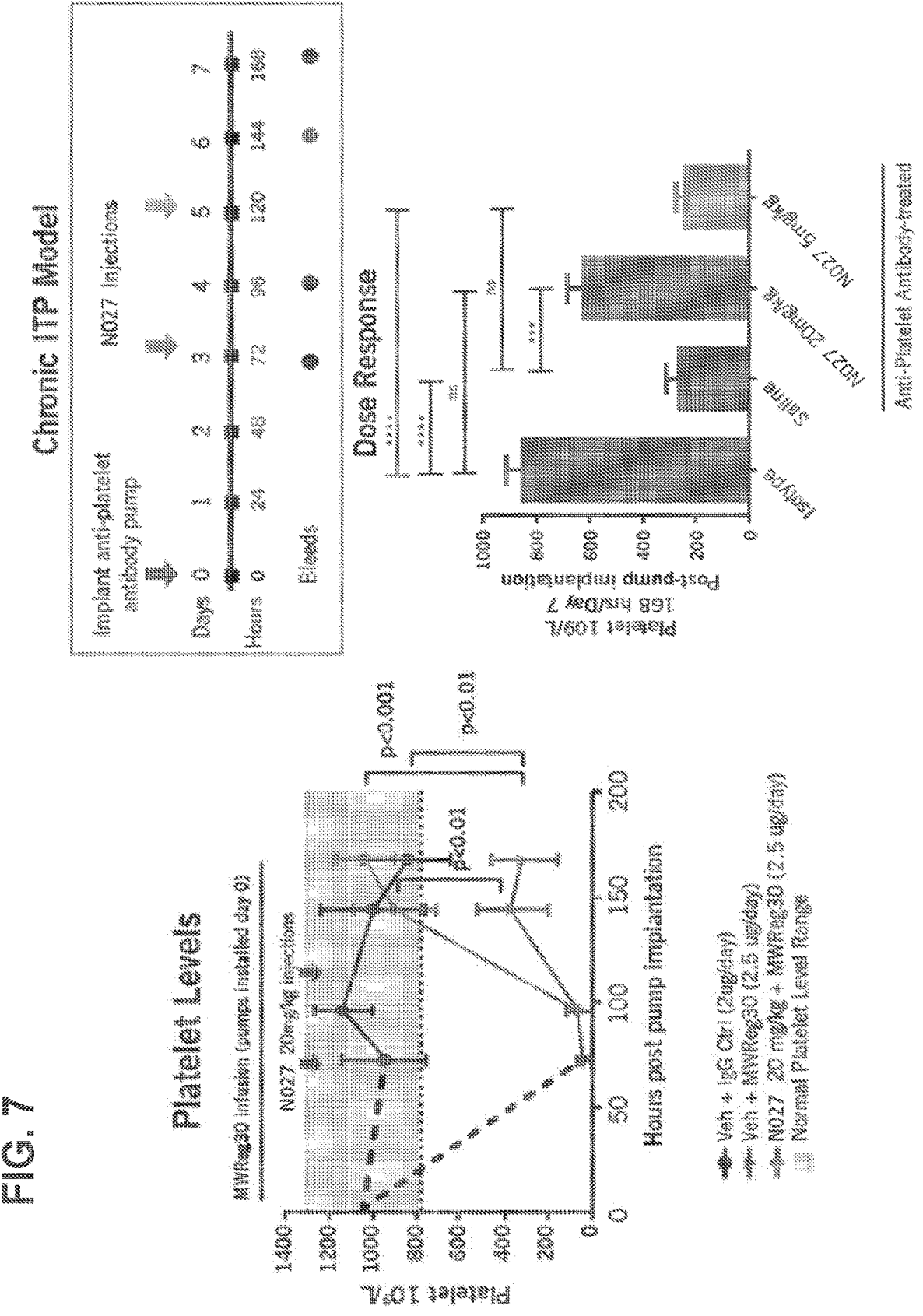
FIG. 7 shows an experimental timeline and two graphs that show the efficacy of N027 in a mouse chronic idiopathic thrombocytopenia purpura (ITP) model in transgenic mice.

Thrombocytopenia was induced in homozygous B6.Cg-Fcgrt$^{tm1Dcr}$Tg(FCGRT)32Dcr/DcrJ mice by continuous subcutaneous infusion of anti-platelet antibody (anti-CD41, MWReg30) via a miniosmotic pump. Circulating platelet levels were decreased to $300 \times 10^9$/L or less by 72 hrs (Day 3) after pump implantation. N027 was dosed therapeutically i.v. 72 hrs (day 3) and 120 hrs (Day 5) post-pump implantation (A, n=4 per group; B, n=7 per group). FIG. 7 shows that N027 when dosed therapeutically, can effectively restore platelet levels in mice having thrombocytopenia.

Figure 8A:
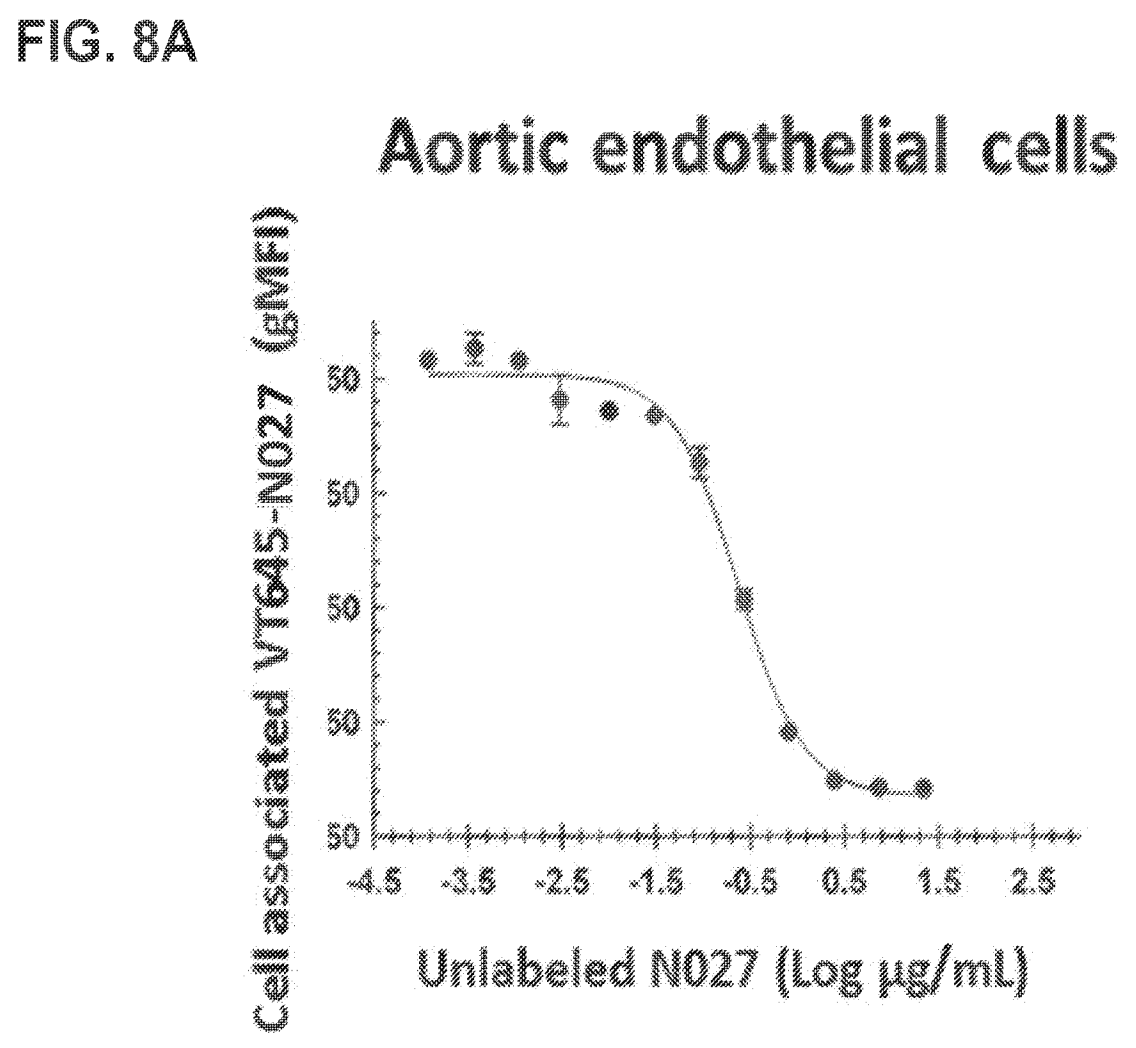
Figure 8B:
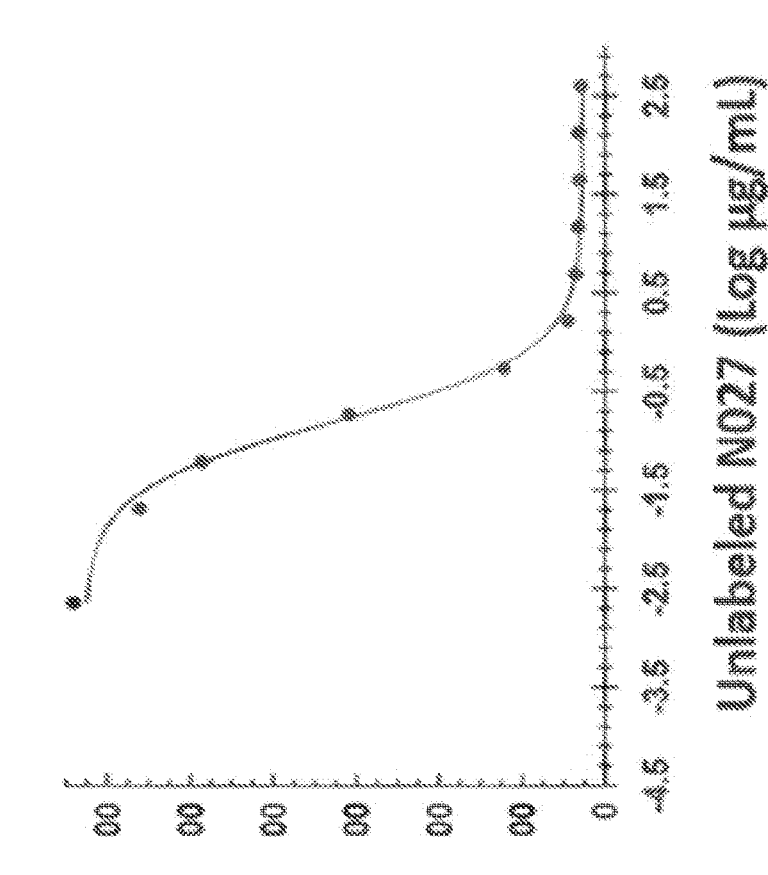
Figure 8C:
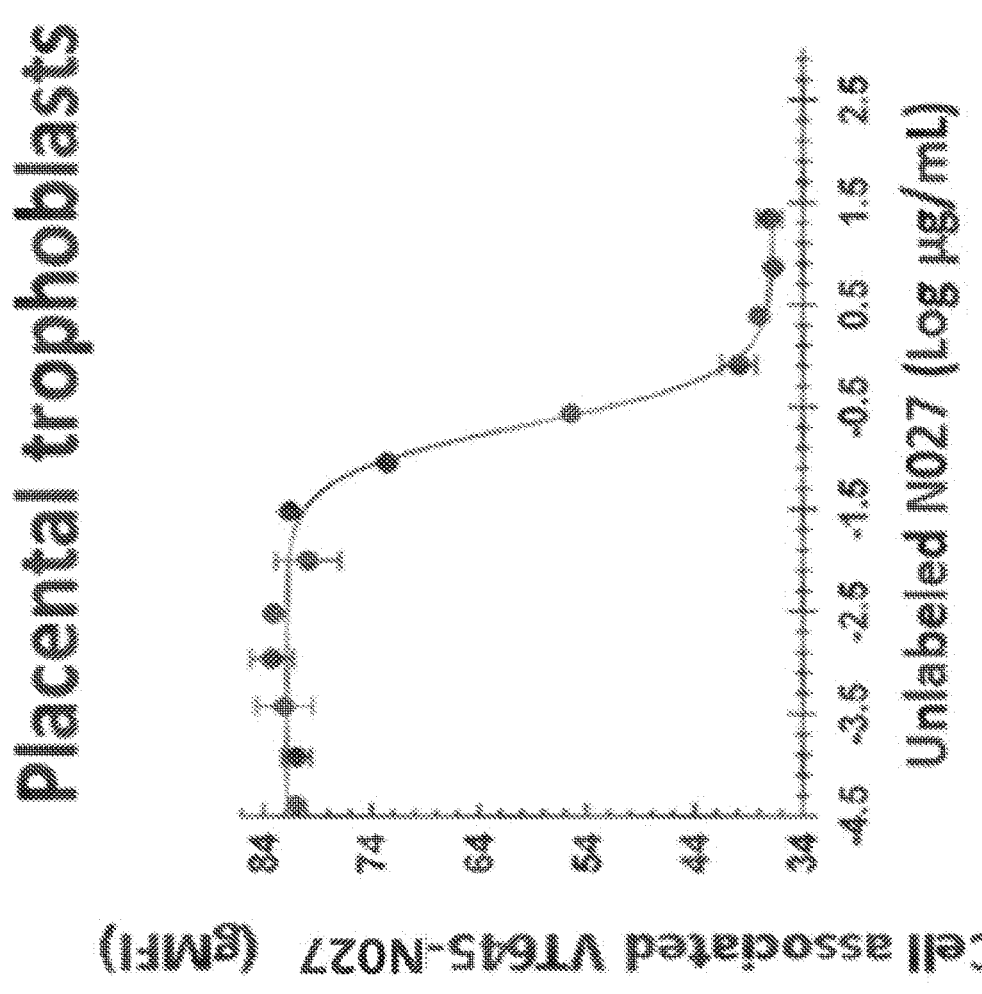

Example 11—Concentration Dependent FcRn Occupancy was Achieved with N027 in Target Cell Types The receptor occupancy by N027 was compared across different cell types such as primary human aortic endothelial cells (HAECs), human umbilical vein endothelial cells (HUVECs) cells and placental trophoblasts (HVTs). Cells were grown to confluency in complete EBM-2 media (Lonza, Waterville) or in trophoblast media (ScienCell). Cell monolayers were incubated in 1 ml of media with different concentrations of unlabeled N027 for 1 hour at 37° C. After washing, cells were harvested with cold HyQTase, fixed and permeabilized before incubation with VivoTag645-labeled N027 (10 µg/ml), for 30 minutes at 4° C. in the dark. Following incubation, cells were washed with permeabilization buffer before resuspending in FACS buffer. Cell-associated VivoTag645-N027 was measured by flow cytometry. The values represent geometric mean fluorescence intensity (gMFI)±SD (n=2). FIGS. 8A, 8B, and 8C show the FcRn occupancy across N027 concentrations for the HAECs, HUVECs and HVTs, respectively. The results as summarized in Table 4 show that human ECs (HAECs, HUVECs) as well as placental HVTs exhibit similar concentration dependence receptor occupancy by N027.

TABLE 4

| Human Primary Cells | $IC_{50}$ | 100% FcRn occupancy dose |
| --- | --- | --- |
| Aortic endothelial cells (HAECs) | 0.23 µg/mL | 2.43 µg/mL |
| Venous endothelial cells (HUVECs) | 0.15 µg/mL | 4.99 µg/mL |
| Placental trophoblast cells (HVTs) | 0.15 µg/mL | 2.43 µg/mL |

Example 12—N027 Concentrations Achieving 100% Receptor Occupancy Result in Increased Intracellular IgG Accumulation The relation between levels of receptor occupancy and alterations in IgG intracellular trafficking by N027 was compared across different cell types. Human endothelial cells (HAECs and HUVECs) were cultured in endothelial cell culture (EBM-2, Lonza) while human placental trophoblasts (HVTs) were cultured in trophoblast media (ScienCell). Cell monolayers were then pulsed for 4-5 hours at 37° C. in 1 mL media containing either:

1. varying concentrations of N027+VivoTag645-IgG (50 µg/mL); or
2. varying concentrations of Isotype control IgG+VivoTag645-IgG (50 µg/mL)

Figure 9A:
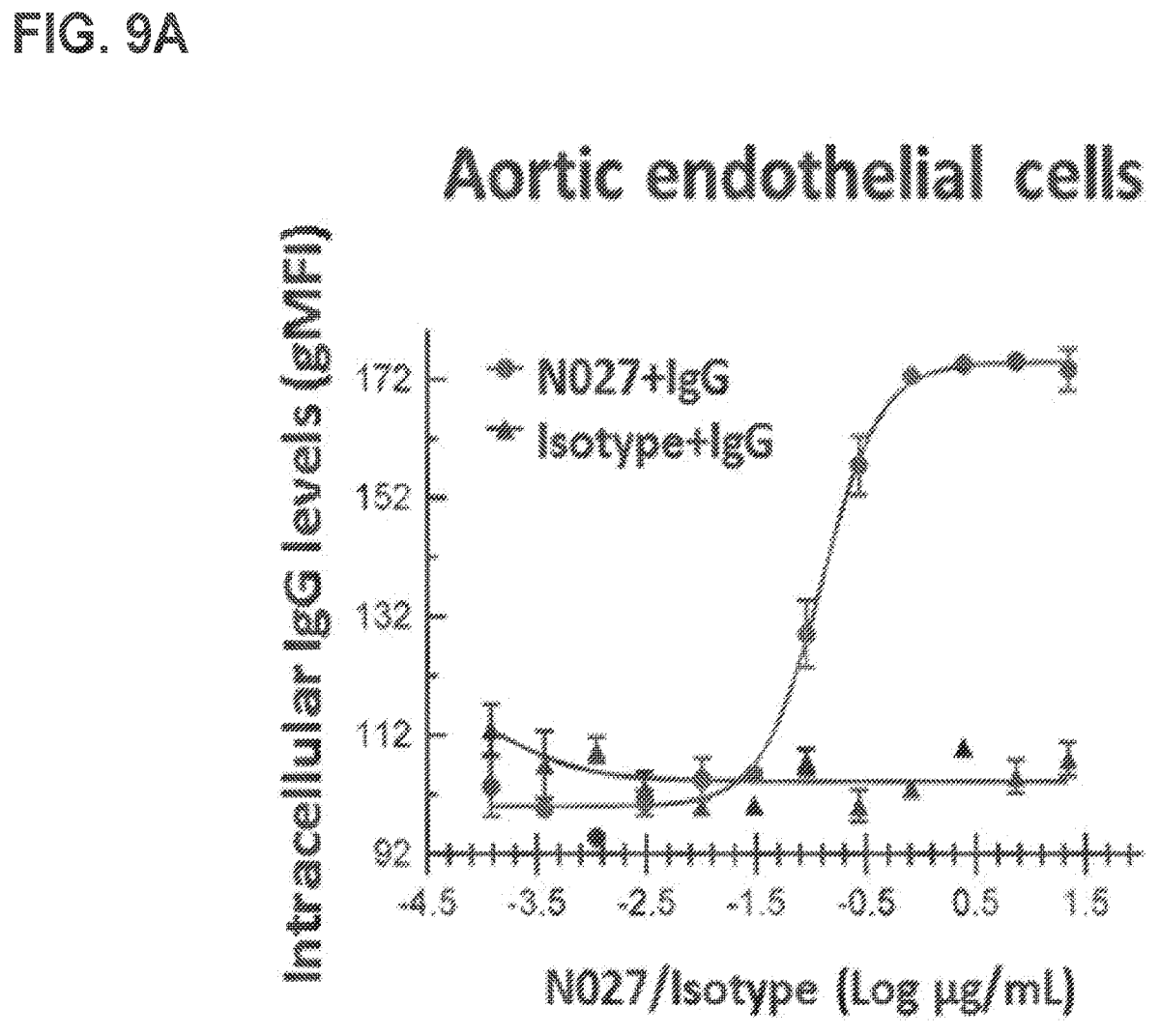
Figure 9B:
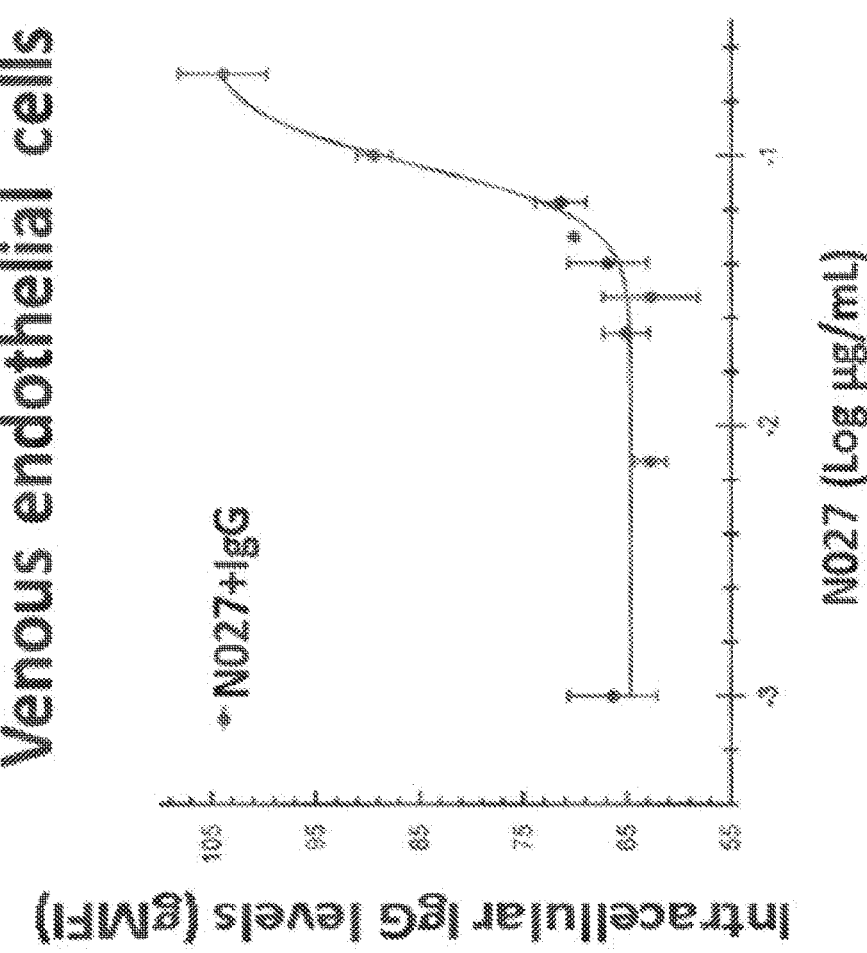
Figure 9C:
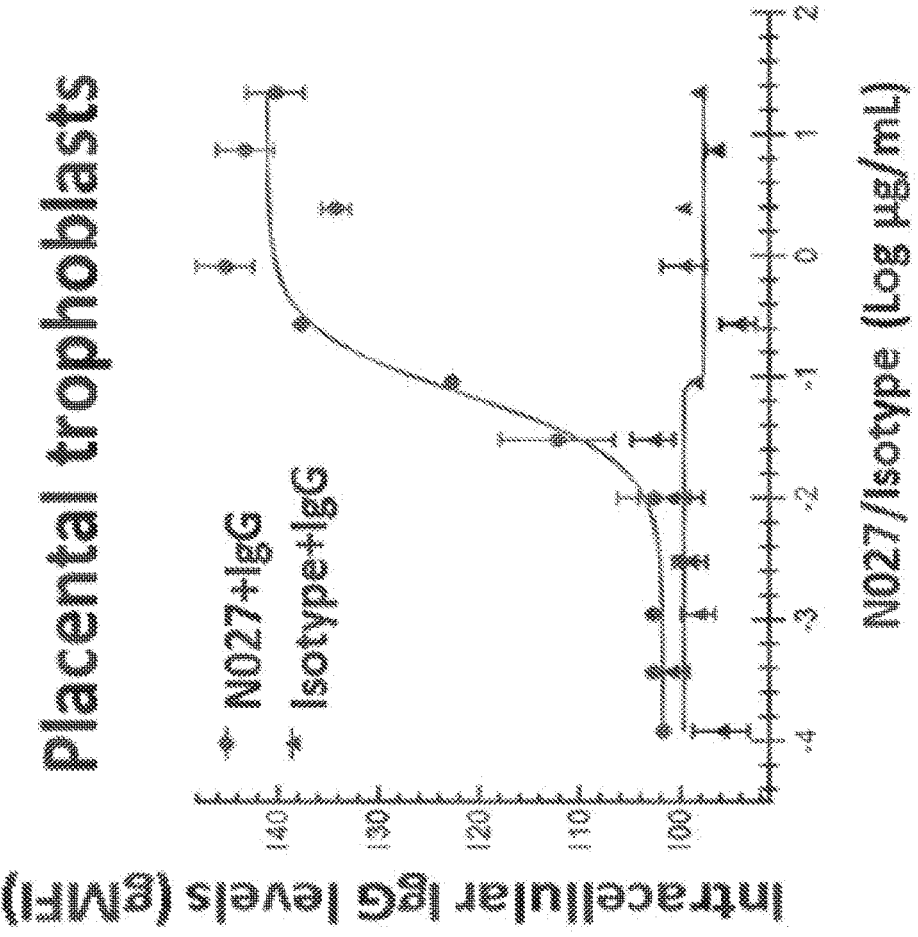

Cell monolayers were then washed in cold media followed by cell detachment by HyQtase treatment. Cell associated VivoTag645-N027 was measured by flow cytometry. Values represent geometric mean fluorescence intensity (gMFI)±SD (n=2). FIGS. 9A, 9B, and 9C show the intracellular IgG levels for the HAECs, HUVECs and HVTs, respectively, corresponding to various doses of N027. N027 doses corresponding to >100% FcRn occupancy resulted in significantly higher IgG accumulation compared to isotype controls. The results demonstrate that the effective N027 concentrations needed to achieve saturating levels of IgG accumulation is similar in these target cell types and ranges from 4.99 to 2.43 µg/mL as summarized in Table 5

TABLE 5

| Human Primary Cells | $IC_{50}$ | 100% FcRn occupancy dose |
| --- | --- | --- |
| Aortic endothelial cells (HAECs) | 0.12 µg/mL | 2.43 µg/mL |
| Venous endothelial cells (HUVECs) | 0.15 µg/mL | 4.99 µg/mL |
| Placental trophoblast cells (HVTs) | 0.07 µg/mL | 3.68 µg/mL |

Example 13—Measurement of Time to 100% FcRn-Occupancy

Figure 10:
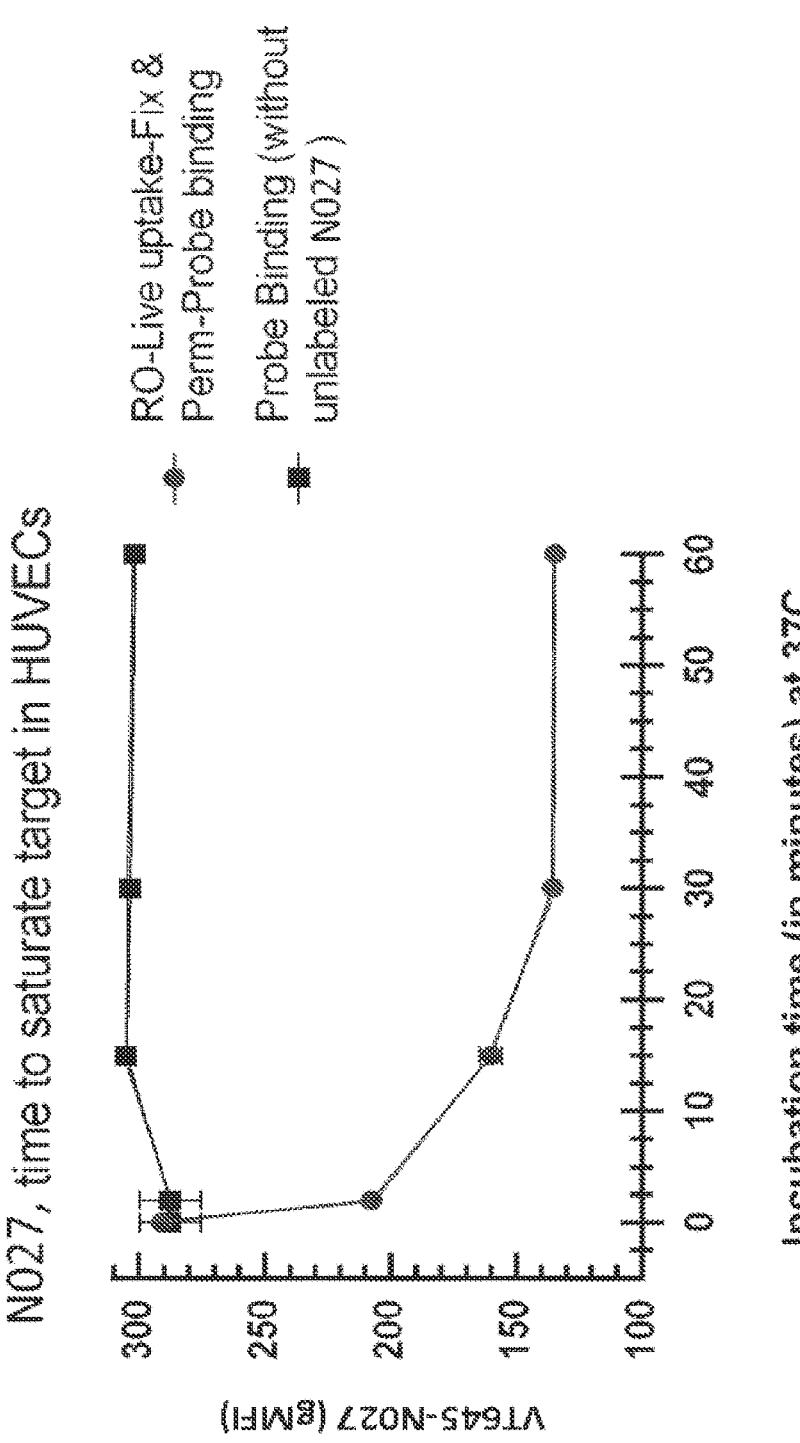
FIG. 10 shows a graph that shows the amount of time it takes to achieve 100% FcRn occupancy by N027.

To determine the time taken by N027 to saturate FcRn and block IgG trafficking, confluent vascular endothelial cell (HUVEC) monolayers were incubated with or without a saturating concentration of N027 (16.6 µg/ml) in EBM-2 media for the indicated times at 37° C. (FIG. 10). Upon completion of incubation, cells were washed and harvested with cold HyQtase, followed by fixing and permeabilization. These cells were then incubated in permeabilization buffer+ 10% human serum and VivoTag645-labeled N027 (10 µg/mL) for 30 minutes at 4° C. in the dark. The cells were then washed with permeabilization buffer, resuspended in FACS buffer and cell-associated VivoTag645-N027 was measured by FACS. Values represent mean gMFI±SD (n=2). The results shown in FIG. 10 indicates that 100% FcRn-occupancy by N027 was achieved in about 30 minutes in this endothelial cell type.

Example 14—Human Vascular Endotheilal Cells and Placental Trophoblasts Exhibit Similar FcRn Turnover Rates which are Unaltered by N027

Figure 11A:
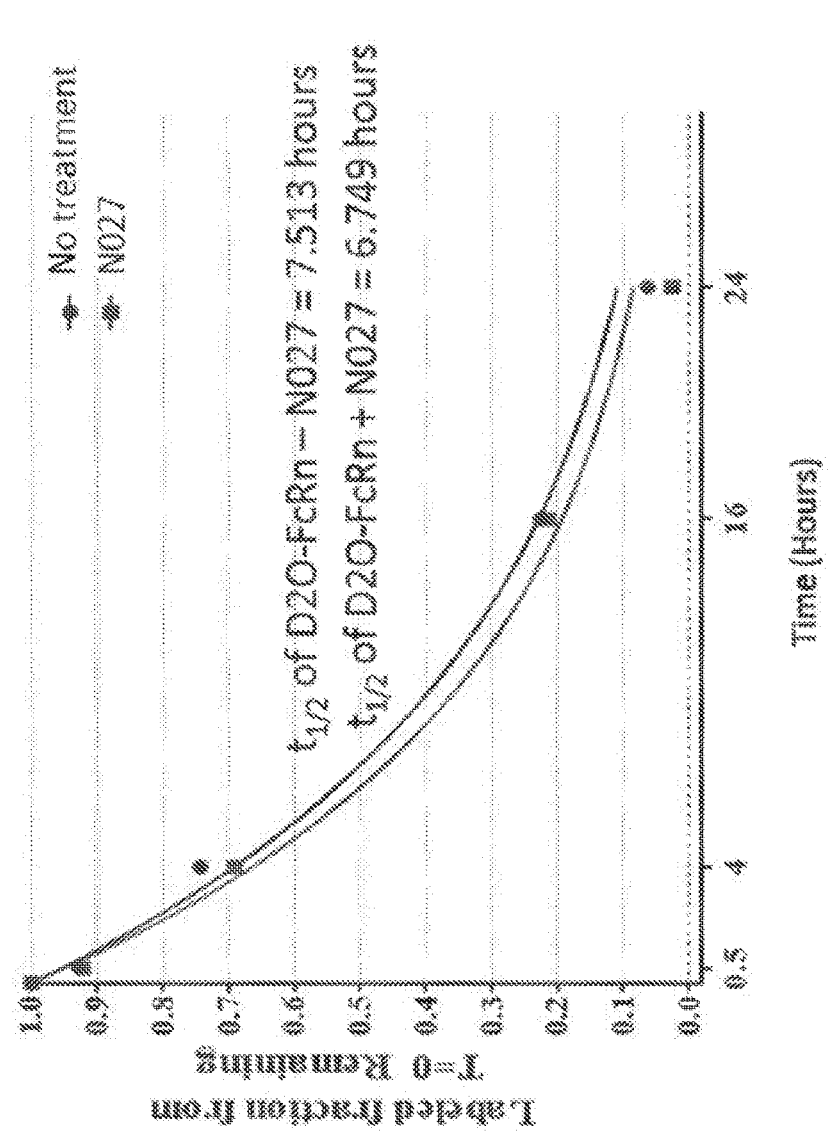
FIGS. 11A and 11B show graphs that show N027 treatment does not alter FcRn turnover rates in human endothelial and villous trophoblast cells, respectively.
Figure 11B:
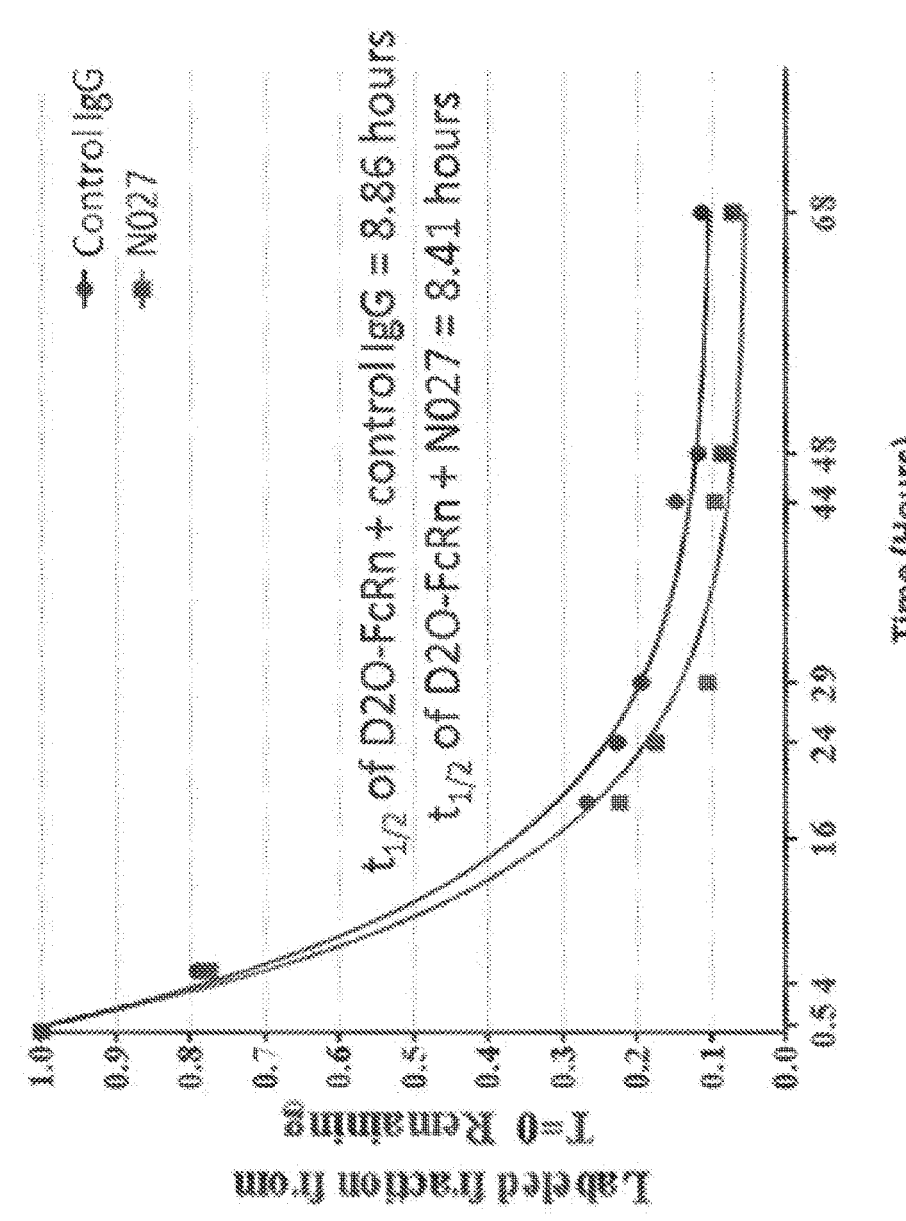

The FcRn turnover rates of human vascular endothelial cells (HUVECs) and placental trophoblasts (HVTs) were compared in the presence and absence of N027. Cells were cultured in 75 cm² flask in 25% D20 (Deuterium Oxide, from Aldrich) containing media for three days. After three days, the media was replaced with normal media containing N027 (100 µg/mL) or control IgG (100 µg/ml) or mock treatment. Cells were then harvested from the flasks at indicated times post media change (FIGS. 11A and 11B). The cell monolayers were washed; cells were harvested, pelleted, and individual pellets were lysed and digested separately. Shotgun proteomics and targeted proteomics were performed. Using Qual Browser, isotopic relative intensities were extracted and fractional abundances were calculated for each isotopomer by dividing each intensity by the total. Fractional abundance values were used to calculate the percentage of $D_2O$-labeled FcRn remaining in the system. FIGS. 11A and 11B show that FcRn turnover rates are similar between human vascular endothelial cells (HUVECs) and placental trophoblasts (HVTs). Furthermore, treatment with N027 did not change the FcRn turnover rates.

Example 15—FcRn Localization in Target Cells

The localization of N027 was compared in human vascular endothelial cells (HUVECs) and placental trophoblasts (HVTs). Cells were grown on glass coverslips in EBM-2/ TM media. Live cells were incubated in media containing DyLight594-N027 (2 µg/mL) for 1 hour at 37° C. Cells were then washed and imaged live on fluorescence microscope in confocal mode with 60× dry objective using appropriate filters. Representative single cell images show similar local-ization pattern of N027 bound to the endocytic pool of FcRn in both cell types (FIGS. 12A and 12B). The circle in the center of the cell indicates the location of the nucleus.

Figures 13A, 13B:
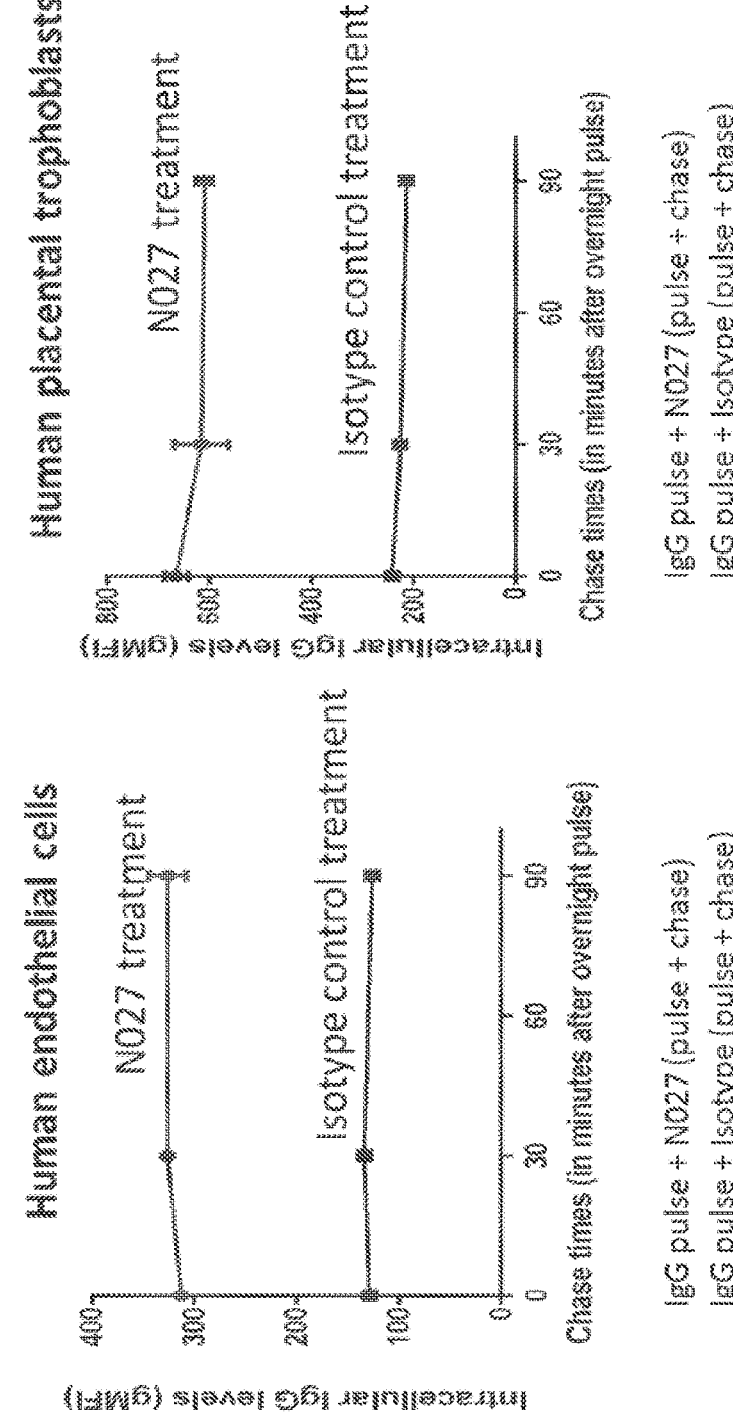
FIGS. 13A and 13B show graphs that show the effect of N027 treatment on dynamics of IgG trafficking in human endothelial cells and human placental trophoblasts, respectively.

Example 168—Effect of N027 Treatment on Dynamics of IgG Trafficking: Intracellular IgG Accumulation and Co-Localization with Lysosomes The effect of N027 treatment on dynamics of intracellular IgG accumulation was compared across FcRn expressing target cell types such as human vascular endothelial cells (HUVECs) and placental trophoblasts (HVTs). Cells were grown to confluency in EBM-2 media (Lonza, Waterville) or TM1 media (ScienCell). Confluent cell monolayers were then pulsed in 1 ml media containing either N027 (2 μg/ml)+VivoTag645-IgG (50 μg/mL) or isotype control IgG (2 μg/mL)+VivoTag645-IgG (50 μg/ml) for 20 hours at 37° C. Cell monolayers were then washed and then chased for 0 min, 30 min, and 90 min at 37° C. in chase media containing either N027 (2 μg/mL) or Isotype control (2 μg/ml). After each chase period, cells were washed, detached, and col-lected by HyQtase treatment. Cell-associated VivoTag645-N027 was measured by flow cytometry. Values represent geometric mean fluorescence intensity (gMFI)±SD (n=2). Cells treated with N027 showed higher levels of intracellular IgG. Further, the effect of N027 on the dynamics of intra-cellular IgG accumulation was similar between the two cells types tested as shown in FIGS. 13A and 13B.

Figure 13C:
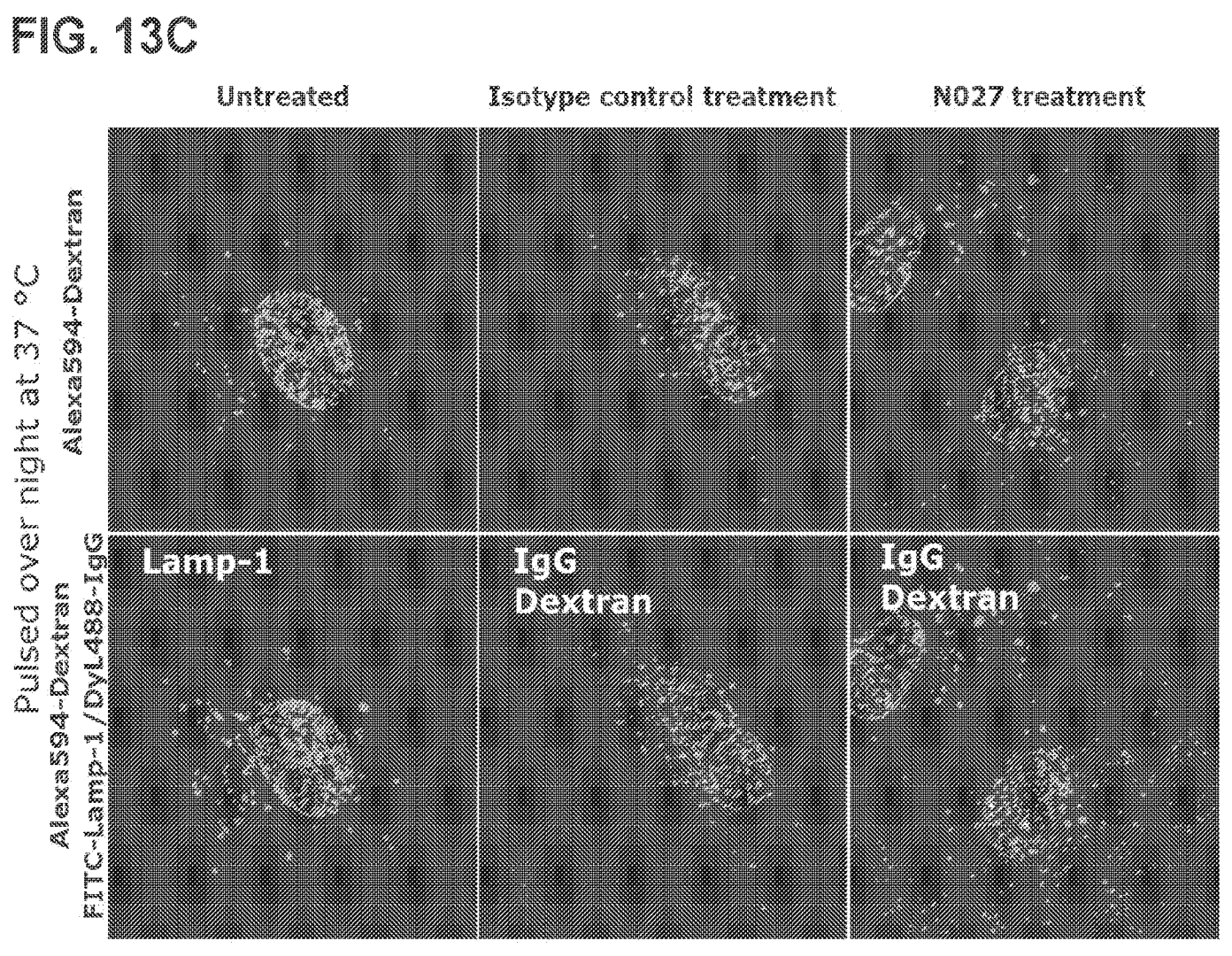
Figure 13D:
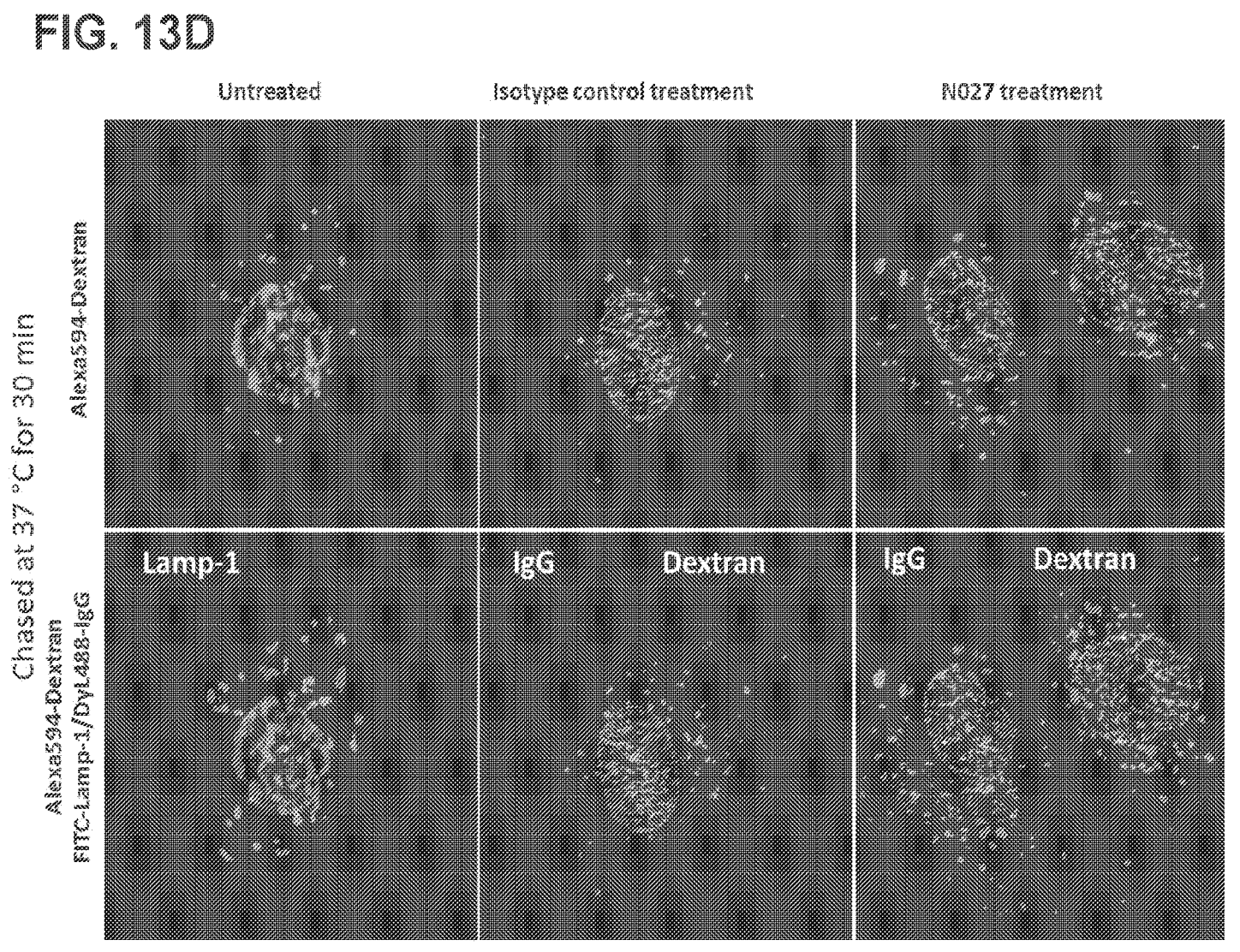

We also determined whether N027 increases intracellular IgG and co-localization of IgG with lysosomes in primary human umbilical vein endothelial cells (HUVECs). Cells were grown on glass coverslips and incubated in media containing 10 μg/ml Alexa Fluor 594 Dextran (10,000 MW, anionic, fixable) for 2 hours at 37° C. Following incubation cells were washed and pulsed at 37° C. for 20 hours in either N027 (2 μg/ml)+DyLight 488-IgG (50 μg/ml) containing media or Isotype control IgG (2 μg/ml)+DyLight 488-IgG (50 μg/ml) containing media; or in media without any IgG-treatments. The plates were washed in cold media and then chased for 0 min or 30 min at 37 GC. The following chase conditions were used: the N027+DyLight 488-IgG pulsed set was chased in the presence of N027 (2 μg/mL); the Isotype+DyLight 488-IVIG pulsed set was chased in the presence of isotype control IgG (2 μg/mL) and the set without any IgG-treatments was chased in media only. Cells were washed, incubated in BD Cytofix/Cytoperm solution for 30 min at 4° C. in the dark, washed with perm wash buffer followed by incubation in perm wash buffer+10% normal mouse serum+5 μg/ml mouse anti-human Lamp1 antibody for overnight at 4° C. in the dark. Cells were then washed with perm wash buffer and PBS, and then mounted on glass slides. Cell imaging was done using confocal mode on Olympus fluorescence microscope with a 60× dry objec-tive with 2× optical magnification. As presented in FIGS. 13C and 13D, it was shown that N027 treatment increases the accumulation of IgG in the lysosomal compartment as compared to isotype control IgG-treated cells.

Example 17—Determination and Analysis of a Structure of FcRn (a Heterodimer Comprised of FcRn/p51 and β2-Microglobulin/p14) in Complex with the N027 Fab The complex of N027 Fab:FcRn was purified and con-centrated to about 9 mg/ml in a buffer composed of 30 mM HEPES (pH 7.5), 200 mM NaCl, 3% glycerol. This complex was set up in sitting drop vapor diffusion crystallization experiments. Drops consisting of 0.3 μl protein solution plus 0.3 μl reservoir solution were mixed over a reservoir of 80 μl of the reservoir solution. The plates were sealed and allowed to equilibrate at 4° C.

Plate-like crystals grew in several conditions over the course of 4 days to 7 weeks. The crystal that ultimately led to the structure of the complex grew in a mother liquor consisting of 10% PEG 1000, 10% PEG 8000. The crystal was cryoprotected by soaking for about 2 minutes in a solution of 25% PEG 1000, 10% PEG 8000, 100 mM NaCl before mounting in a cryoloop and plunge-freezing in liquid nitrogen.

X-ray diffraction data were collected at the Stanford Synchrotron Radiation Lightsource (SSRL) on beamline BL9-2, using a Dectris Pilatus 6M detector and a wavelength of 0.97946 Å. The diffraction images were processed to a resolution of 2.7 Å using HKL-2000 followed by various programs in the CCP4 (Collaborative Computational Proj-ect, Number 4) software suite. Details of data collection and processing are contained in Table 6.

The 2.7 Å structure of the N027 Fab:FcRn complex was solved by molecular replacement using search models con-sisting of a complete FcRn (heterodimer of large and small subunits, p51 and p14, respectively) from Protein Data Bank (PDB) ID No. 4k71 and individual heavy and light chains of human Fab from PDB ID No. 5v7u with the program Phaser. There is one complete complex in the asymmetric unit with a solvent content of approximately 65%. The structure was subsequently completed and refined by successive rounds of manual building and real space refinement in the program Coot followed by restrained refinement against the X-ray data using the program Refmac5 and validation using the program Molprobity and various tools within Coot. The last several rounds of refinement in Refmac5 included TLS refinement with each chain defined as an individual TLS group. Details of structure solution and refinement are contained in Table 7.

TABLE 6

| Parameter | Value* |
|---|---|
| Space group | C121 |
| Unit cell parameters | |
| a, b, c (Å) | 183.2, 67.6, 105.2 |
| α, β, γ (°) | 90.0, 104.9, 90.0 |
| Resolution range (Å) | 41.5-2.7 (2.75-2.70) |
| No. of reflections | 115,072 |
| No. of unique reflections | 33,982 |
| Completeness (%) | 98.1 (96.4) |
| Multiplicity | 3.4 (3.2) |
| (I/σ | 7.4 (1.0) |
| $R_{merge}$ (%) | 13.5 (75.7) |
| $R_{pim}$ (%) | 8.6 (48.2) |
| Overall B from Wilson plot (Å²) | 40.8 |

*values in parentheses are for the highest resolution shell

TABLE 7

| Parameter | Value |
|---|---|
| Resolution range (Å) | 41.5-2.7 |
| Fraction of test reflections (%) | 4.9 |
| Final $R_{work}$ (%) | 21.5 |
| Final $R_{free}$ (%) | 26.3 |
| Mean B value (overall, Å²) | 28.6 |
| R.m.s. deviations | |
| Bonds (Å) | 0.01 |
| Angles (°) | 1.50 |

TABLE 7-continued

| Parameter | Value |
|---|---|
| Ramachandran plot | |
| Most favored (%) | 95.39 |
| Allowed (%) | 4.35 |
| Outliers (%) | 0.26 |

Structural Analysis of the FcRn Epitope

Figure 14:
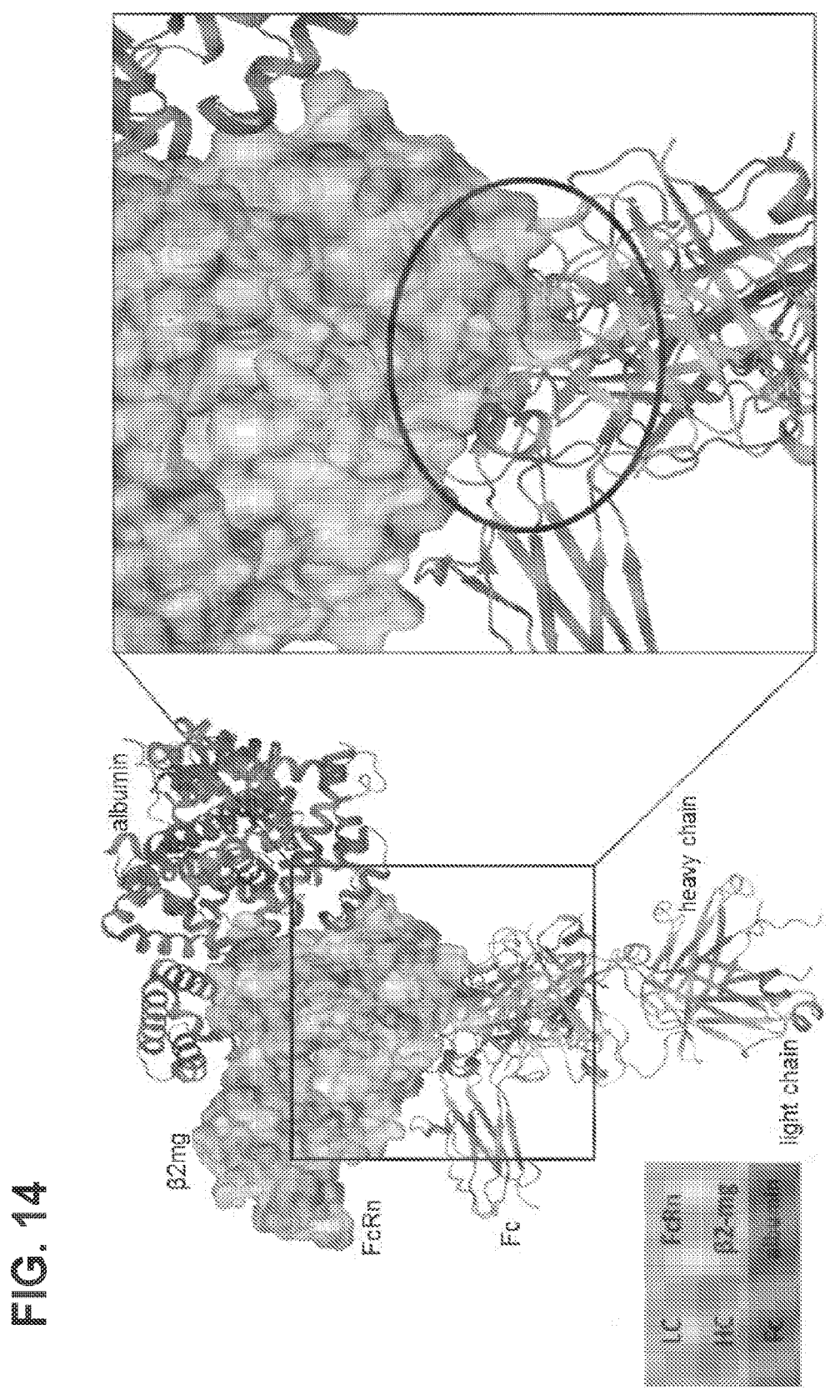
Figure 15:
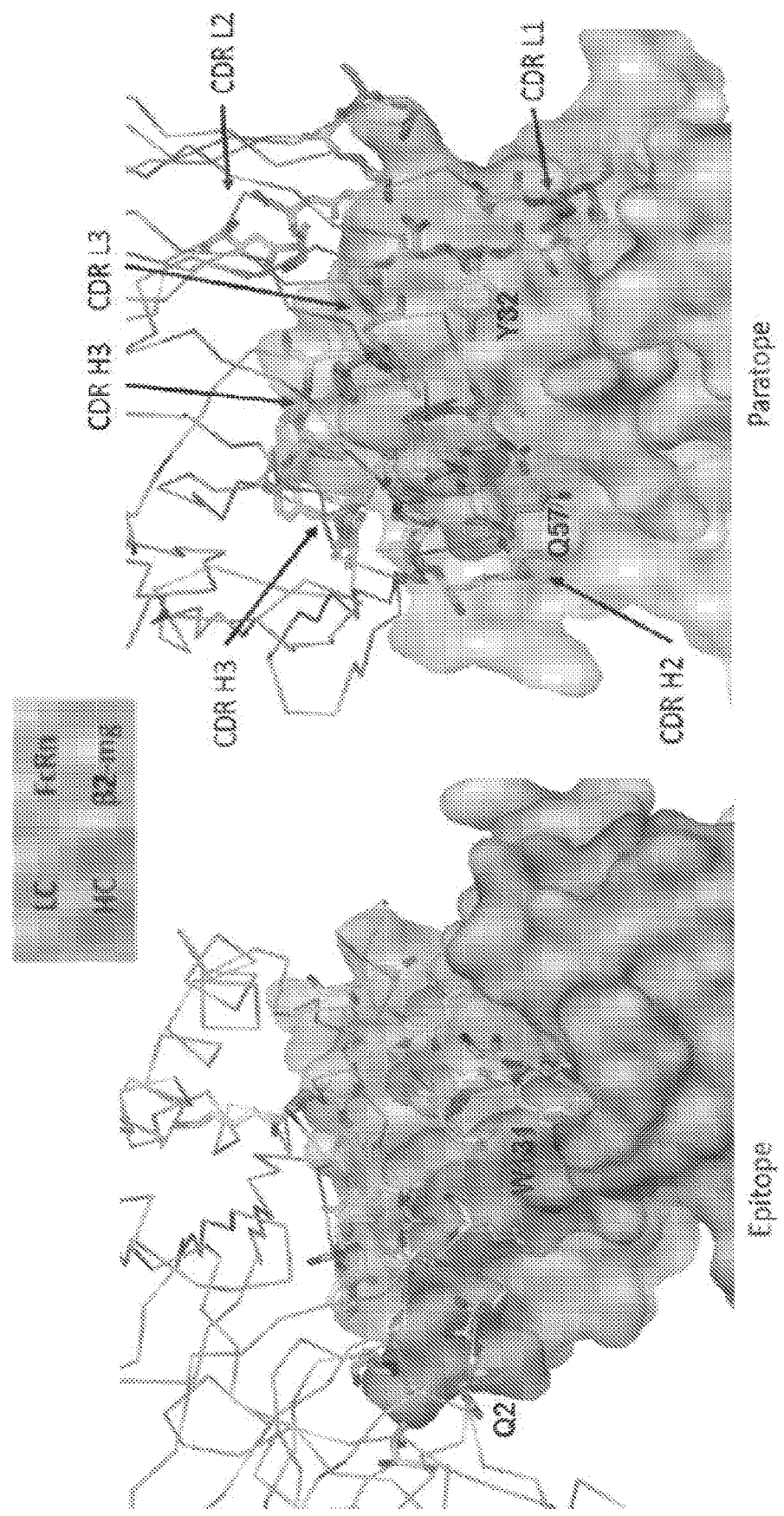
FIG. 15 shows images of the epitope on the N027 Fab surface (left) and paratope on the FcRn surface (right).

The epitope of FcRn defined by the crystal structure is composed primarily of amino acids on the FcRn/p51 subunit but four amino acids from the P2-microglobulin/p14 subunit are also involved. Overall, the interaction between the N027 Fab and FcRn buries approximately 1020 Å², with 470 Å² between the light chain and FcRn, 414 Å² between the heavy chain and FcRn, and 136 Å² between the light chain and β2-microglobulin. All three CDR loops from both chains of the N027 Fab are involved in the paratope with CDR H2 and CDR L1 together contributing about half of the interacting amino acid with eight apiece. CDRs H1, H3, and L2 contribute three amino acids each and CDR L3 contributes five. Three amino acids (KSG) at positions 66-68 Kabat in the light chain framework between CDRs L2 and L3 are also involved in binding. The epitope/paratope interface is fully defined by the electron density and has been fully modeled unambiguously. The Fab binding opitope on FcRn overlaps the canonical Fc binding site so tight binding by the FcRn antibodies is expected to block Fc binding. Additionally, the albumin binding site remains accessible. Additionally, a N-acetylglucosamine is present on Gln102 of FcRn that is well-defined by the electron density. An overview of the epitope as defined by the crystal structure is depicted and are mapped onto the sequence in FIGS. 14-16. The W131 and Y88 residues on FCGRT appear to be the most significant residues that bind through H-bonding to the CDR L3 (YAGSGIY) and CDR H2 (R58) on the anti-FcRn N027 molecule.

Example 18—Suppression of Endogenous Maternal and Fetal IgG in Cynomolgus Monkeys by N027 and Lack of N027 Transfer to Fetal Circulation Pregnant female cynomolgus monkeys wore dosed weekly from Gestation Day 45 (GD45) to C-section at GD100 (mid-gestation) or GD140 (late gestation). A cohort of animals was also included in the study that were allowed to deliver their infants (birth day [BD1]). The design study is depicted in Table 8.

TABLE 8

Study Design

| Group No. | Test Material | Dose Level (mg/ kg) | Dose Volume (mL/ kg) | Dose Concen- tration (mg/mL) | No. of Females for C-section[a] GD100 ± 2 | GD140 ± 2 | Live Birth BD1 |
|---|---|---|---|---|---|---|---|
| 1 | Control | 0 | 10 | 0 | 4 | 4 | 3 |
| 2 | N027 | 100 | 10 | 10 | 4 | 4 | — |
| 3 | N027 | 300 | 10 | 30 | 4 | 4 | 3 |

[a]Twenty-four (24) pregnant females were initially enrolled on study (8 per group). Four pregnancies per group were assigned to the GD140 ± 2 C-section cohort, and the remaining 4 pregnancies per group were assigned to the GD100 ± 2 cohort.

IgG concentrations were measured in maternal and neonatal blood samples using a standard validated total IgG ELISA (Table 9). Briefly, polystyrene plates (96-well) were coated with commercially available anti-human IgG antigen. The coated plate(s) were washed to remove unbound sample and then blocked using with blocking buffer followed by a wash to remove the residual blocking buffer. Serum samples were diluted and added to the anti-human IgG coated wells and incubated at room temperature for 60±5 minutes. Each well was washed before addition of secondary (detection) antibody conjugated to horseradish peroxidase (HRP) and incubated at room temperature for 60±5 minutes. Tetramethylbenzidine (TMB) substrate was subsequently added to each well and incubated at room temperature for 20±5 minutes on a plate shaker, before addition of 2N $H_2SO_4$ to stop the enzymatic reaction. The absorbance of each well was read at 450 nm using the SpectraMax 190 microplate reader. Any commercially available or proprietary pair of anti-human IgG capture antibody and HRP conjugated anti-human IgG detection antibody that recognizes total IgG and is cross-reactive with cynomolgus monkey IgG can be used to measure total cynomolgus monkey IgG in an ELISA. The IgG detection antibody can be, for example, intact IgG, polyclonal serum antibody, monoclonal antibody, or a Fab (2) fragment.

TABLE 9

Methods

| Assay | Method |
|---|---|
| Total IgG EUSA | 1. Coat immunoassay plate with anti-human IgG. |
| | 2. Incubate with sample |
| | 3. Detect with HRP labeled and addition of TMB substrate |
| Receptor Occupancy by Fluorescence Activated Cell Sorting (FACS) | 1. Whole blood was treated with ammonium chloride to lyse RBC |
| | 2. Cells were spun, washed with PBS, stained with viability dye and incubated with Fc receptor blocking solution |
| | 3. Cells were washed with Perm/Wash buffer, suspended in buffer and incubated with fluor labeled N027 for 20 mins |
| | 4. Cells were then washed and resuspended in FACS buffer before analysis by FACS |

For all pregnant adult females assigned to study, blood was collected by venipuncture from the femoral vein (preferred) or cephalic/saphenous veins according to Table 10. For all fetuses obtained by C-section on GD100±2 or GD140±2, blood was collected from the umbilical cord according to Table 10. Samples (1 mL) were allowed to clot for at least 60 minutes; centrifuged and the resultant serum was separated, transferred to appropriately labeled (e.g., IgG) polypropylene tubes, and frozen immediately in a freezer set to maintain −80° C.

TABLE 10

Sample Collection Timepoints for Evaluation

| Gestation Day[b] | Time Points Relative to Dosing | Samples Collected |
|---|---|---|
| GD381 (prestudy) | Prestudy | Adult female: IgG |
| GD44-46 (first dose) | Predose | Adult female: IgG |
| GD44-46 (first dose) | Postdose: 2 hr | Adult female: IgG |
| GD44-46 | Postdose: 4 hr | — |
| GD45-47 | GD45: 24 hr | Adult female: IgG |
| GD47-49 | GD45: 72 hr | Adult female: IgG |
| GD48-50 | GD45: 96 hr | Adult female: IgG |
| GD51-53 | GD52: Predose | Adult female: IgG |
| GD58-60 | GD59:Predose | Adult female: IgG |

TABLE 10-continued

Sample Collection Timepoints for Evaluation

| Gestation Day[b] | Time Points Relative to Dosing | Samples Collected |
|---|---|---|
| GD6b-67 | GD66: Predose | Adult female: IgG |
| GD72-74 | GD73: Predose | Adult female: IgG |
| GD79-81 | GD80: Predose | Adult female: IgG |
| GD86-88 | GD87: Predose | Adult female: IgG |
| GD93-95 | GD94: Predose | Adult female: IgG |
| GD93-95[a] | GD94: 2 hr | Adult female: IgG |
| GD93-95[a] | GD94: 4 hr | — |
| GD94-96[a] | GD94: 24 hr | Adult female: IgG |
| GD96-98[a] | GD94: 72 hr | Adult female: IgG |
| GD97-99[a] | GD94: 96 hr | Adult female: IgG |
| GD100 ± 2 | NA | Adult female: IgG; |
| (1st C-section cohort) | | Fetus: IgG |
| GD100-102 | GD101: Predose | Adult female: IgG |
| GD107-109 | GD108: Predose | Adult female: IgG |
| GD114-1 16 | GD115: Predose | Adult female: IgG |
| GD121-123 | GD122: Predose | Adult female: IgG |
| GD128-130 | GD129: Predose | Adult female: igG |
| GD135-137 (last dose) | GDl36: Predose | Adult female: IgG |
| GD135-137 | GD136: 2 hr | Adult female: IgG |
| GD135-137 | GD136: 4 hr | — |
| GD136-138 | GD136: 24 hr | Adult female: IgG |
| GD138-140 | GD136: 72 hr | Adult female: IgG |
| GD139-1 41 | GD136: 96 hr | Adult female: IgG |
| GD140 ± 2 | NA | Adult female: IgG |
| (2nd C-section cohort) | | Fetus: IgG total |
| Day of parturition | NA | Adult female: IgG |
| (Maternal: PPD1) | | Neonate: IgG |
| (Neonate: BD1) | | |

[a]Time points were only collected from animals in the GD100 C-section cohorts.
[b]Collection ranges listed based on potential dose days of GD44 to 46. All time points were based off of the dose day.

Suppression of Endogenous Maternal IgG

N027 administration resulted in dose-independent reductions in serum IgG levels in adult females beginning 72 hours postdose, and the greatest reductions in serum IgG concentrations were observed for both the 100 and 300 mg/kg dosed animals at the GD51-53: predose time point (FIG. 19). The serum IgG values for Group 2 (100 mg/kg) trended toward predose levels in a dose-dependent manner, beginning at the GD65-67: predose time point and continuing until the next dose administrations on GD93-95 and GD135-137, after which, reductions of a similar magnitude were present within 72 hours of dosing. Group 3 animals (300 mg/kg) remained at a nadir IgG value at all pre-dose timepoints (as referred to in Table 10) throughout the dosing period. No change in IgG from baseline was observed in animals treated with vehicle (Group 1).

Dose-dependent increases in serum IgG concentrations were present 2 hours after dose administration on GD44-46, GD93-95, and GD135-137. These increases were likely the result of the detection of N027 by the total IgG assay and were not considered to be related to the pharmacology of N027. Dose-dependent reductions in fetal serum IgG levels were present relative to control values at the GD100 and GD140, and in neonates at the BD1 time point (FIG. 20).

Lack of N027 Transfer from Maternal to Fetal Circulation

The transfer of N027 from maternal circulation to fetal circulation was evaluated by measuring the level of N027 FcRn occupancy in fetal circulating monocytes. N027 receptor occupancy was assessed on monocytes, granulocytes, B-lymphocytes, and T-lymphocytes using a flow cytometric (FACS) assay to measure the binding of fluorescent-labeled N027 to free/unbound FcRn in the presence and absence of saturating concentrations of N027. The unsaturated samples demonstrated the percentages of free or unbound FcRn receptor present on each leukocyte subset at each predose and postdose time point. The saturated samples were spiked with concentrations of unlabeled N027 that were determined to completely saturate any FcRn receptors that remained free/unbound at each postdose time point. N027 receptor occupancy was not detected in the whole blood of fetuses on day GD100 and GD140, or in neonates on BD1, in the context of the unsaturated sample analysis as described above.

Example 19—Evaluation of the Transplacental Transfer of N027

Human placenta obtained from uncomplicated term pregnancies were utilized in an ex-vivo dual perfusion single placental lobule method to evaluate the transplacental transfer of N027. Briefly, each placenta was examined for tears, and two chorionic vessels (one artery and vein) supplying a single intact peripheral cotyledon were cannulated with 3F and 5F umbilical catheters, respectively. The cotyledon was trimmed and placed in the perfusion chamber with the maternal surface upward. The intervillous space on the maternal side was perfused by two catheters piercing the basal plate. The flow rate of the perfusate medium in the fetal and maternal circuits was 3.0 and 12 mL/min, respectively. The maternal perfusate was equilibrated with a gas mixture made of 95% 02 and 5% $CO_2$, and the fetal perfusate with a mixture of 95% N2 and 5% $CO_2$. All experiments were carried out at a temperature of 37° C.

Each placental lobule was perfused for an initial control period of one hour to allow the tissue to stabilize to its new environment using an open-open configuration of the perfusion system. Perfusion was terminated if one of the following occurred during the control period: a volume loss in the fetal circuit in an excess of 3 mL/h, or a $pO_2$ difference between the fetal vein and the artery less than 60 mmHg, indicating inadequate perfusion overlap between the two circuits. The control period was followed by an experimental period of four hours using a closed-closed configuration (i.e., re-circulation of the medium) of the perfusion system. The latter was initiated by replacing the medium of the maternal and fetal reservoirs and the addition of 3 mg/ml of BSA.

Figure 17:
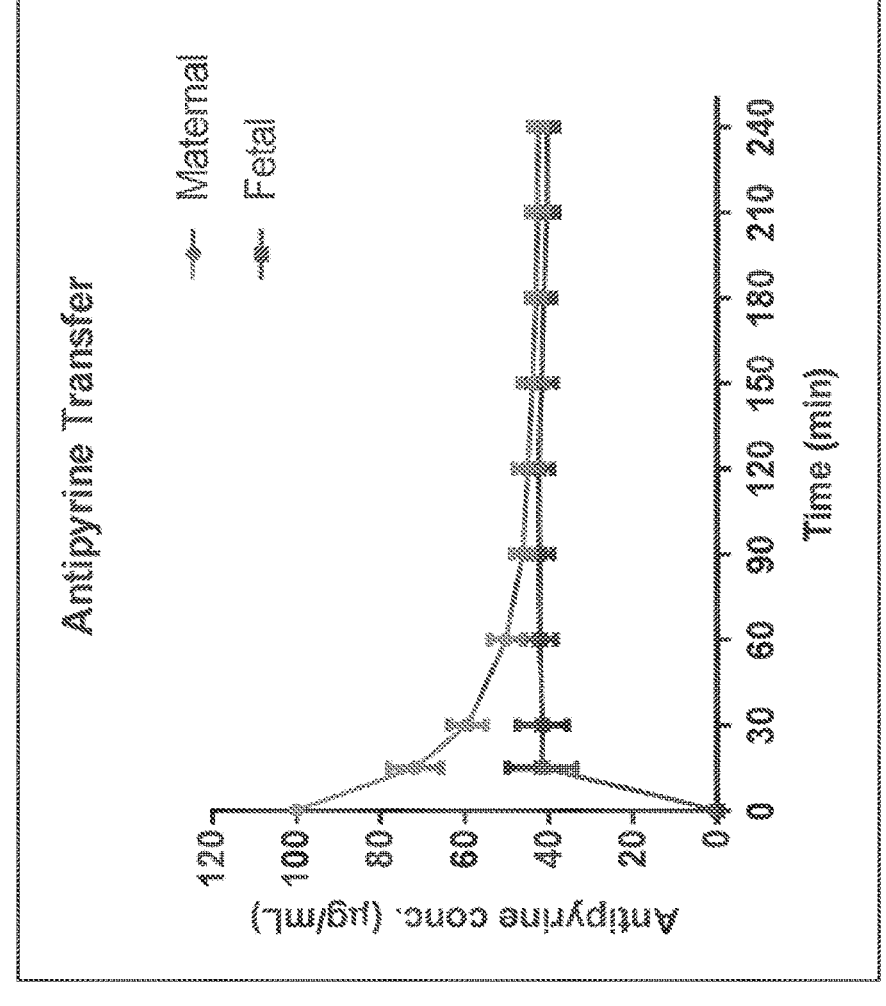
FIG. 17 is a graph that shows transplacental transfer of antipyrine over four hours of perfusion (n=14). The data represent antipyrine concentrations as mean±standard deviation (SD) in the fetal (squares) and maternal (circles) circulation after maternal administration of 100 µg/ml antipyrine at t=0.
Figure 18:
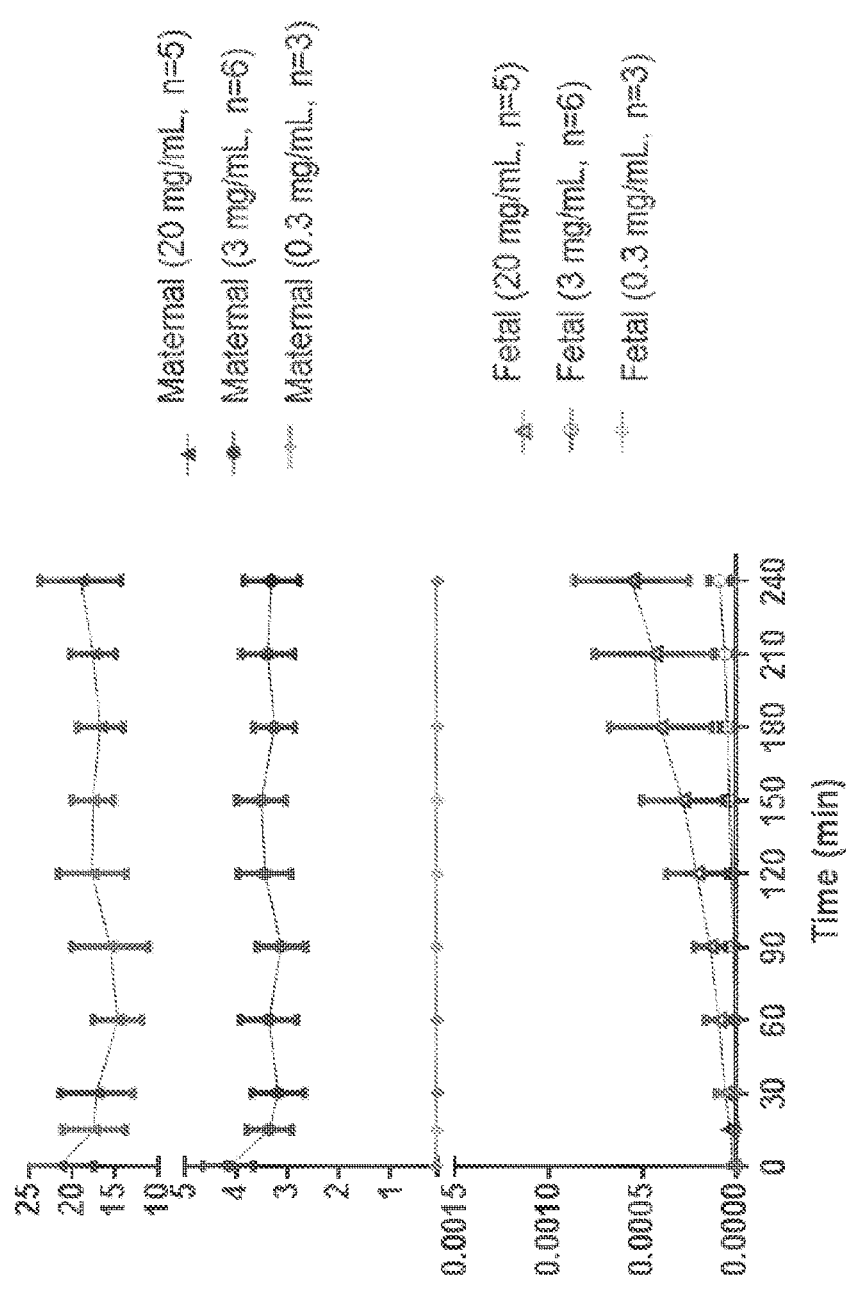
FIG. 18 is a graph that shows transplacental transfer of N027 over four hours of perfusion. The data represent N027 concentrations as mean±SD in the fetal and maternal circulation after maternal administration of the indicated concentration of N027 at t=0.

The transfer of N027 across the human placental lobule was tested for three different concentrations: 0.3 mg/ml, 3 mg/ml, and 30 mg/ml. Fourteen individual placentae were perfused for four hours with N027 being added to the maternal perfusate at 0.3 mg/ml, 3 mg/ml, and 30 mg/ml. Samples from the maternal artery and fetal vein, in 0.5 mL aliquots, were taken at 0, 15, 30, 60, 90, 120, 150, 180, 210 and 240 minutes during the experimental period. Antipyrine was employed as a positive control to validate the integrity of the circuits (FIGS. 17-18). Concentrations of N027 in maternal and fetal samples were determined using a sensitive meso scale discovery (MSD) immunoassay with a lower limit of quantification of 5 ng/ml. This assay involved a sandwich format using an anti-idiotypic antibody pair; wherein the MSD plate was coated with an anti-idiotypic Ab followed by incubation with sample and revealed with the second biotinylated anti-idiotypic Ab followed by detection with MSD tagged streptavidin and addition of read buffer. The concentration of antipyrine was determined using a HPLC assay with UV detection at 260 nm after a liquid-liquid extraction. The mean fetal transfer rate for antipyrine across fourteen experiments was 41±2.8%. The mean fetal transfer rate for N027 across fourteen experiments was 0.0027±0.0021% indicating very low levels of transfer. The results suggest that N027 could be used in methods of treating pregnant patients without causing fetal exposure.

OTHER EMBODIMENTS

While the disclosure has described specific embodiments, it will be understood that it is capable of further modifications and this application is intended to cover any variations, uses, or adaptations of the disclosure following, in general, the principles of the disclosure and including such departures from the present disclosure come within known or customary practice within the art to which the disclosure pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

```
                          SEQUENCE LISTING

<160> NUMBER OF SEQ ID NOS: 62

<210> SEQ ID NO 1
<211> LENGTH: 14
<212> TYPE: PRT
<213> ORGANISM: Homo sapiens

<400> SEQUENCE: 1

Thr Gly Thr Gly Ser Asp Val Gly Ser Tyr Asn Leu Val Ser
1               5                   10

<210> SEQ ID NO 2
<211> LENGTH: 7
<212> TYPE: PRT
<213> ORGANISM: Homo sapiens

<400> SEQUENCE: 2

Gly Asp Ser Glu Arg Pro Ser
1               5

<210> SEQ ID NO 3
<211> LENGTH: 10
<212> TYPE: PRT
<213> ORGANISM: Homo sapiens

<400> SEQUENCE: 3

Ser Ser Tyr Ala Gly Ser Gly Ile Tyr Val
1               5                   10

<210> SEQ ID NO 4
<211> LENGTH: 5
<212> TYPE: PRT
<213> ORGANISM: Homo sapiens

<400> SEQUENCE: 4

Thr Tyr Ala Met Gly
1               5

<210> SEQ ID NO 5
<211> LENGTH: 5
<212> TYPE: PRT
<213> ORGANISM: Homo sapiens

<400> SEQUENCE: 5

Asp Tyr Ala Met Gly
1               5

<210> SEQ ID NO 6
<211> LENGTH: 5
<212> TYPE: PRT
<213> ORGANISM: Homo sapiens

<400> SEQUENCE: 6

Asn Tyr Ala Met Gly
```

-continued

```
1               5

<210> SEQ ID NO 7
<211> LENGTH: 14
<212> TYPE: PRT
<213> ORGANISM: Homo sapiens

<400> SEQUENCE: 7

Ser Ile Gly Ser Ser Gly Ala Gln Thr Arg Tyr Ala Asp Ser
1               5                   10

<210> SEQ ID NO 8
<211> LENGTH: 14
<212> TYPE: PRT
<213> ORGANISM: Homo sapiens

<400> SEQUENCE: 8

Ser Ile Gly Ala Ser Gly Ser Gln Thr Arg Tyr Ala Asp Ser
1               5                   10

<210> SEQ ID NO 9
<211> LENGTH: 14
<212> TYPE: PRT
<213> ORGANISM: Homo sapiens

<400> SEQUENCE: 9

Ser Ile Gly Ala Ser Gly Ala Gln Thr Arg Tyr Ala Asp Ser
1               5                   10

<210> SEQ ID NO 10
<211> LENGTH: 14
<212> TYPE: PRT
<213> ORGANISM: Homo sapiens

<400> SEQUENCE: 10

Ser Ile Gly Ala Ser Gly Gly Gln Thr Arg Tyr Ala Asp Ser
1               5                   10

<210> SEQ ID NO 11
<211> LENGTH: 7
<212> TYPE: PRT
<213> ORGANISM: Homo sapiens

<400> SEQUENCE: 11

Leu Ala Ile Gly Asp Ser Tyr
1               5

<210> SEQ ID NO 12
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Gly, Leu, Ile, Ala, Phe, Met, Trp, Val,
      Pro, Ser, Thr, Cys, His, Tyr, Asn, or Gln
<220> FEATURE:
<221> NAME/KEY: MISC_FEATURE
<222> LOCATION: (12)..(12)
<223> OTHER INFORMATION: Xaa is Gly, Leu, Ile, Ala, Phe, Met, Trp, Val,
      or Pro

<400> SEQUENCE: 12

Xaa Gly Thr Gly Ser Asp Val Gly Ser Tyr Asn Xaa Val Ser
1               5                   10
```

```
<210> SEQ ID NO 13
<211> LENGTH: 7
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Ser, Thr, Cys, His, Met, Tyr, Trp, Asn,
      or Gln
<220> FEATURE:
<221> NAME/KEY: MISC_FEATURE
<222> LOCATION: (4)..(4)
<223> OTHER INFORMATION: Xaa is Ser, Thr, Cys, His, Met, Tyr, Trp, Asn,
      Gln, Asp or Glu

<400> SEQUENCE: 13

Gly Asp Xaa Xaa Arg Pro Ser
1               5

<210> SEQ ID NO 14
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Gly, Leu, Ile, Ala, Phe, Met, Trp, Val,
      Pro, Ser, Thr, Cys, His, Tyr, Asn, or Gln
<220> FEATURE:
<221> NAME/KEY: MISC_FEATURE
<222> LOCATION: (4)..(4)
<223> OTHER INFORMATION: Xaa is Gly, Leu, Ile, Ala, Phe, Met, Trp, Val,
      or Pro

<400> SEQUENCE: 14

Xaa Ser Tyr Xaa Gly Ser Gly Ile Tyr Val
1               5                   10

<210> SEQ ID NO 15
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ser, Thr, Cys, His, Met, Tyr, Trp, Asn,
      Gln, Asp or Glu

<400> SEQUENCE: 15

Xaa Tyr Ala Met Gly
1               5

<210> SEQ ID NO 16
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ser or Thr
<220> FEATURE:
<221> NAME/KEY: MISC_FEATURE
<222> LOCATION: (4)..(4)
<223> OTHER INFORMATION: Xaa is Gly, Leu, Ile, Ala, Phe, Met, Trp, Val,
      Pro, Ser, Thr, Cys, His, Tyr, Asn, or Gln
<220> FEATURE:
<221> NAME/KEY: MISC_FEATURE
<222> LOCATION: (7)..(7)
<223> OTHER INFORMATION: Xaa is Gly, Ser, or Ala
<220> FEATURE:
<221> NAME/KEY: MISC_FEATURE
<222> LOCATION: (10)..(10)
<223> OTHER INFORMATION: Xaa is His, Lys, or Arg
```

-continued

<400> SEQUENCE: 16

Xaa Ile Gly Xaa Ser Gly Xaa Gln Thr Xaa Tyr Ala Asp Ser
1               5                   10

<210> SEQ ID NO 17
<211> LENGTH: 7
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Gly, Leu, Ile, Ala, Phe, Met, Trp, Val,
      Pro, His, Lys, or Arg
<220> FEATURE:
<221> NAME/KEY: MISC_FEATURE
<222> LOCATION: (4)..(4)
<223> OTHER INFORMATION: Xaa is Gly, Ser, Asp, Gln, or His

<400> SEQUENCE: 17

Leu Ala Xaa Xaa Asp Ser Tyr
1               5

<210> SEQ ID NO 18
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ser or Thr
<220> FEATURE:
<221> NAME/KEY: MISC_FEATURE
<222> LOCATION: (4)..(4)
<223> OTHER INFORMATION: Xaa is Ser or Ala
<220> FEATURE:
<221> NAME/KEY: MISC_FEATURE
<222> LOCATION: (7)..(7)
<223> OTHER INFORMATION: Xaa is Gly, Ser, or Ala

<400> SEQUENCE: 18

Xaa Ile Gly Xaa Ser Gly Xaa Gln Thr Arg Tyr Ala Asp Ser
1               5                   10

<210> SEQ ID NO 19
<211> LENGTH: 216
<212> TYPE: PRT
<213> ORGANISM: Homo sapiens

<400> SEQUENCE: 19

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Gly Ile Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu

```
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Lys Ser Tyr Ser Cys Gln Val Thr His Glu Gly Ser Thr Val Glu Lys
                195                 200                 205

Thr Val Ala Pro Thr Glu Cys Ser
    210                 215

<210> SEQ ID NO 20
<211> LENGTH: 445
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1                   5                   10                  15

Ser Leu Arg Leu Ser Cys Ala Ala Ser Gly Phe Thr Phe Ser Thr Tyr
                20                  25                  30

Ala Met Gly Trp Val Arg Gln Ala Pro Gly Lys Gly Leu Glu Trp Val
            35                  40                  45

Ser Ser Ile Gly Ser Ser Gly Ala Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
        275             280             285

Lys Pro Arg Glu Glu Gln Tyr Ala Ser Thr Tyr Arg Val Val Ser Val
        290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335

Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Thr Cys Leu Val
        355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly
            435             440             445

<210> SEQ ID NO 21
<211> LENGTH: 445
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Asp Tyr
            20              25              30

Ala Met Gly Trp Val Arg Gln Ala Pro Gly Lys Gly Leu Glu Trp Val
            35              40              45

Ser Ser Ile Gly Ala Ser Gly Ser Gln Thr Arg Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Leu Ala Ile Gly Asp Ser Tyr Trp Gly Gln Gly Thr Met Val
            100             105             110

Thr Val Ser Ser Ala Ser Thr Lys Gly Pro Ser Val Phe Pro Leu Ala
            115             120             125

Pro Ser Ser Lys Ser Thr Ser Gly Gly Thr Ala Ala Leu Gly Cys Leu
        130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
        195             200             205
```

```
Lys Val Asp Lys Lys Val Glu Pro Lys Ser Cys Asp Lys Thr His Thr
    210             215                 220

Cys Pro Pro Cys Pro Ala Pro Glu Leu Leu Gly Gly Pro Ser Val Phe
225             230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
            435                 440                 445

<210> SEQ ID NO 22
<211> LENGTH: 445
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
            35                  40                  45

Ser Ser Ile Gly Ala Ser Gly Ala Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
```

-continued

```
         130              135              140

Val Lys Asp Tyr Phe Pro Glu Pro Val Thr Val Ser Trp Asn Ser Gly
145              150              155              160

Ala Leu Thr Ser Gly Val His Thr Phe Pro Ala Val Leu Gln Ser Ser
                 165              170              175

Gly Leu Tyr Ser Leu Ser Ser Val Val Thr Val Pro Ser Ser Ser Leu
                 180              185              190

Gly Thr Gln Thr Tyr Ile Cys Asn Val Asn His Lys Pro Ser Asn Thr
                 195              200              205

Lys Val Asp Lys Lys Val Glu Pro Lys Ser Cys Asp Lys Thr His Thr
         210              215              220

Cys Pro Pro Cys Pro Ala Pro Glu Leu Leu Gly Gly Pro Ser Val Phe
225              230              235              240

Leu Phe Pro Pro Lys Pro Lys Asp Thr Leu Met Ile Ser Arg Thr Pro
                 245              250              255

Glu Val Thr Cys Val Val Val Asp Val Ser His Glu Asp Pro Glu Val
                 260              265              270

Lys Phe Asn Trp Tyr Val Asp Gly Val Glu Val His Asn Ala Lys Thr
                 275              280              285

Lys Pro Arg Glu Glu Gln Tyr Ala Ser Thr Tyr Arg Val Val Ser Val
         290              295              300

Leu Thr Val Leu His Gln Asp Trp Leu Asn Gly Lys Glu Tyr Lys Cys
305              310              315              320

Lys Val Ser Asn Lys Ala Leu Pro Ala Pro Ile Glu Lys Thr Ile Ser
                 325              330              335

Lys Ala Lys Gly Gln Pro Arg Glu Pro Gln Val Tyr Thr Leu Pro Pro
                 340              345              350

Ser Arg Glu Glu Met Thr Lys Asn Gln Val Ser Leu Thr Cys Leu Val
                 355              360              365

Lys Gly Phe Tyr Pro Ser Asp Ile Ala Val Glu Trp Glu Ser Asn Gly
                 370              375              380

Gln Pro Glu Asn Asn Tyr Lys Thr Thr Pro Pro Val Leu Asp Ser Asp
385              390              395              400

Gly Ser Phe Phe Leu Tyr Ser Lys Leu Thr Val Asp Lys Ser Arg Trp
                 405              410              415

Gln Gln Gly Asn Val Phe Ser Cys Ser Val Met His Glu Ala Leu His
                 420              425              430

Asn His Tyr Thr Gln Lys Ser Leu Ser Leu Ser Pro Gly
                 435              440              445
```

```
<210> SEQ ID NO 23
<211> LENGTH: 445
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Thr Tyr
                 20              25              30

Ala Met Gly Trp Val Arg Gln Ala Pro Gly Lys Gly Leu Glu Trp Val
                 35              40              45

Ser Ser Ile Gly Ala Ser Gly Gly Gln Thr Arg Tyr Ala Asp Ser Val
         50              55              60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445
```

<210> SEQ ID NO 24
<211> LENGTH: 445
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ser Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Leu Ala Ile Gly Asp Ser Tyr Trp Gly Gln Gly Thr Met Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415
```

-continued

```
Gln Gln Gly Asn Val Phe Ser Cys Ser Val Met His Glu Ala Leu His
          420                 425                 430

Asn His Tyr Thr Gln Lys Ser Leu Ser Leu Ser Pro Gly
          435                 440                 445

<210> SEQ ID NO 25
<211> LENGTH: 13
<212> TYPE: PRT
<213> ORGANISM: Homo sapiens

<400> SEQUENCE: 25

Lys Gln Gly Thr Trp Gly Gly Asp Trp Pro Glu Ala Leu
1                 5                 10

<210> SEQ ID NO 26
<211> LENGTH: 12
<212> TYPE: PRT
<213> ORGANISM: Homo sapiens

<400> SEQUENCE: 26

Phe Lys Ala Leu Gly Gly Lys Gly Pro Tyr Thr Leu
1                 5                 10

<210> SEQ ID NO 27
<211> LENGTH: 13
<212> TYPE: PRT
<213> ORGANISM: Homo sapiens

<400> SEQUENCE: 27

Gly Glu Glu Phe Met Asn Phe Asp Leu Lys Gln Gly Thr
1                 5                 10

<210> SEQ ID NO 28
<211> LENGTH: 8
<212> TYPE: PRT
<213> ORGANISM: Homo sapiens

<400> SEQUENCE: 28

Glu Glu Phe Met Asn Phe Asp Leu
1                 5

<210> SEQ ID NO 29
<211> LENGTH: 9
<212> TYPE: PRT
<213> ORGANISM: Homo sapiens

<400> SEQUENCE: 29

Trp Gly Gly Asp Trp Pro Glu Ala Leu
1                 5

<210> SEQ ID NO 30
<211> LENGTH: 280
<212> TYPE: PRT
<213> ORGANISM: Homo sapiens

<400> SEQUENCE: 30

Ala Glu Ser His Leu Ser Leu Leu Tyr His Leu Thr Ala Val Ser Ser
1                 5                 10                 15

Pro Ala Pro Gly Thr Pro Ala Phe Trp Val Ser Gly Trp Leu Gly Pro
                20                 25                 30

Gln Gln Tyr Leu Ser Tyr Asn Ser Leu Arg Gly Glu Ala Glu Pro Cys
          35                 40                 45

Gly Ala Trp Val Trp Glu Asn Gln Val Ser Trp Tyr Trp Glu Lys Glu
```

-continued

```
        50                    55                    60

Thr Thr Asp Leu Arg Ile Lys Glu Lys Leu Phe Leu Glu Ala Phe Lys
65                      70                      75                      80

Ala Leu Gly Gly Lys Gly Pro Tyr Thr Leu Gln Gly Leu Leu Gly Cys
                        85                      90                      95

Glu Leu Gly Pro Asp Asn Thr Ser Val Pro Thr Ala Lys Phe Ala Leu
                        100                     105                     110

Asn Gly Glu Glu Phe Met Asn Phe Asp Leu Lys Gln Gly Thr Trp Gly
                        115                     120                     125

Gly Asp Trp Pro Glu Ala Leu Ala Ile Ser Gln Arg Trp Gln Gln Gln
            130                     135                     140

Asp Lys Ala Ala Asn Lys Glu Leu Thr Phe Leu Leu Phe Ser Cys Pro
145                     150                     155                     160

His Arg Leu Arg Glu His Leu Glu Arg Gly Arg Gly Asn Leu Glu Trp
                        165                     170                     175

Lys Glu Pro Pro Ser Met Arg Leu Lys Ala Arg Pro Ser Ser Pro Gly
                        180                     185                     190

Phe Ser Val Leu Thr Cys Ser Ala Phe Ser Phe Tyr Pro Pro Glu Leu
                        195                     200                     205

Gln Leu Arg Phe Leu Arg Asn Gly Leu Ala Ala Gly Thr Gly Gln Gly
            210                     215                     220

Asp Phe Gly Pro Asn Ser Asp Gly Ser Phe His Ala Ser Ser Ser Leu
225                     230                     235                     240

Thr Val Lys Ser Gly Asp Glu His His Tyr Cys Cys Ile Val Gln His
                        245                     250                     255

Ala Gly Leu Ala Gln Pro Leu Arg Val Glu Leu Glu Ser Pro Ala Lys
                        260                     265                     270

Ser Ser His His His His His His
            275                     280
```

```
<210> SEQ ID NO 31
<211> LENGTH: 99
<212> TYPE: PRT
<213> ORGANISM: Homo sapiens

<400> SEQUENCE: 31
```

```
Ile Gln Arg Thr Pro Lys Ile Gln Val Tyr Ser Arg His Pro Ala Glu
1                       5                       10                      15

Asn Gly Lys Ser Asn Phe Leu Asn Cys Tyr Val Ser Gly Phe His Pro
                        20                      25                      30

Ser Asp Ile Glu Val Asp Leu Leu Lys Asn Gly Glu Arg Ile Glu Lys
            35                      40                      45

Val Glu His Ser Asp Leu Ser Phe Ser Lys Asp Trp Ser Phe Tyr Leu
            50                      55                      60

Leu Tyr Tyr Thr Glu Phe Thr Pro Thr Glu Lys Asp Glu Tyr Ala Cys
65                      70                      75                      80

Arg Val Asn His Val Thr Leu Ser Gln Pro Lys Ile Val Lys Trp Asp
                        85                      90                      95

Arg Asp Met
```

```
<210> SEQ ID NO 32
<211> LENGTH: 220
<212> TYPE: PRT
<213> ORGANISM: Homo sapiens

<400> SEQUENCE: 32
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ser Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp
    210                 215                 220

<210> SEQ ID NO 33
<211> LENGTH: 216
<212> TYPE: PRT
<213> ORGANISM: Homo sapiens

<400> SEQUENCE: 33

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Gly Ile Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
```

-continued

```
145              150              155              160

Ala Gly Val Glu Thr Thr Thr Pro Ser Lys Gln Ser Asn Asn Lys Tyr
                165              170              175

Ala Ala Ser Ser Tyr Leu Ser Leu Thr Pro Glu Gln Trp Lys Ser His
            180              185              190

Lys Ser Tyr Ser Cys Gln Val Thr His Glu Gly Ser Thr Val Glu Lys
        195              200              205

Thr Val Ala Pro Thr Glu Cys Ser
    210              215

<210> SEQ ID NO 34
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is any amino acid

<400> SEQUENCE: 34

Val Gly Xaa Tyr Asn Leu
1               5

<210> SEQ ID NO 35
<211> LENGTH: 4
<212> TYPE: PRT
<213> ORGANISM: Homo sapiens

<400> SEQUENCE: 35

Gly Asp Ser Glu
1

<210> SEQ ID NO 36
<211> LENGTH: 7
<212> TYPE: PRT
<213> ORGANISM: Homo sapiens

<400> SEQUENCE: 36

Tyr Ala Gly Ser Gly Ile Tyr
1               5

<210> SEQ ID NO 37
<211> LENGTH: 3
<212> TYPE: PRT
<213> ORGANISM: Homo sapiens

<400> SEQUENCE: 37

Thr Tyr Ala
1

<210> SEQ ID NO 38
<211> LENGTH: 10
<212> TYPE: PRT
<213> ORGANISM: Homo sapiens

<400> SEQUENCE: 38

Ser Ile Gly Ala Ser Gly Ser Gln Thr Arg
1               5               10

<210> SEQ ID NO 39
<211> LENGTH: 10
<212> TYPE: PRT
<213> ORGANISM: Homo sapiens
<220> FEATURE:
```

```
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid

<400> SEQUENCE: 39

Ser Ile Xaa Ala Ser Xaa Ser Gln Xaa Arg
1               5                   10

<210> SEQ ID NO 40
<211> LENGTH: 3
<212> TYPE: PRT
<213> ORGANISM: Homo sapiens

<400> SEQUENCE: 40

Leu Ala Ile
1

<210> SEQ ID NO 41
<211> LENGTH: 14
<212> TYPE: PRT
<213> ORGANISM: Homo sapiens

<400> SEQUENCE: 41

Thr Ile Gly Ser Ser Gly Ala Gln Thr Arg Tyr Ala Asp Ser
1               5                   10

<210> SEQ ID NO 42
<211> LENGTH: 14
<212> TYPE: PRT
<213> ORGANISM: Homo sapiens

<400> SEQUENCE: 42

Ser Ile Gly Ala Ser Gly Ser Gln Thr Arg Tyr Ala Asp Ser
1               5                   10

<210> SEQ ID NO 43
<211> LENGTH: 14
<212> TYPE: PRT
<213> ORGANISM: Homo sapiens

<400> SEQUENCE: 43

Thr Ile Gly Ala Ser Gly Ala Gln Thr Arg Tyr Ala Asp Ser
1               5                   10

<210> SEQ ID NO 44
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Ser or Ala
<220> FEATURE:
<221> NAME/KEY: MISC_FEATURE
<222> LOCATION: (7)..(7)
<223> OTHER INFORMATION: Xaa is Gly, Ser, or Ala

<400> SEQUENCE: 44

Ser Ile Gly Xaa Ser Gly Xaa Gln Thr Arg Tyr Ala Asp Ser
1               5                   10
```

```
<210> SEQ ID NO 45
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Gly, Leu, Ile, Ala, Phe, Met, Trp, Val,
      Pro, Ser, Thr, Cys, His, Tyr, Asn, or Gln
<220> FEATURE:
<221> NAME/KEY: MISC_FEATURE
<222> LOCATION: (7)..(7)
<223> OTHER INFORMATION: Xaa is Gly, Ser, or Ala
<220> FEATURE:
<221> NAME/KEY: MISC_FEATURE
<222> LOCATION: (10)..(10)
<223> OTHER INFORMATION: Xaa is His, Lys, or Arg

<400> SEQUENCE: 45

Ser Ile Gly Xaa Ser Gly Xaa Gln Thr Xaa Tyr Ala Asp Ser
1               5                   10

<210> SEQ ID NO 46
<211> LENGTH: 14
<212> TYPE: PRT
<213> ORGANISM: Homo sapiens

<400> SEQUENCE: 46

Thr Ile Gly Ala Ser Gly Gly Gln Thr Arg Tyr Ala Asp Ser
1               5                   10

<210> SEQ ID NO 47
<211> LENGTH: 8
<212> TYPE: PRT
<213> ORGANISM: Homo sapiens

<400> SEQUENCE: 47

Ser Asp Val Gly Ser Tyr Asn Leu
1               5

<210> SEQ ID NO 48
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Gly, Leu, Ile, Ala, Phe, Met, Trp, Val,
      Pro, Ser, Thr, Cys, His, Tyr, Asn, or Gln

<400> SEQUENCE: 48

Xaa Gly Thr Gly Ser Asp Val Gly Ser Tyr Asn Leu Val Ser
1               5                   10

<210> SEQ ID NO 49
<211> LENGTH: 14
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: Xaa is Gly, Leu, Ile, Ala, Phe, Met, Trp, Val,
      or Pro

<400> SEQUENCE: 49

Thr Gly Thr Gly Ser Asp Val Gly Ser Tyr Asn Xaa Val Ser
1               5                   10
```

```
<210> SEQ ID NO 50
<211> LENGTH: 7
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Ser, Thr, Cys, His, Met, Tyr, Trp, Asn,
      or Gln

<400> SEQUENCE: 50

Gly Asp Xaa Glu Arg Pro Ser
1               5

<210> SEQ ID NO 51
<211> LENGTH: 7
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Ser, Thr, Cys, His, Met, Tyr, Trp, Asn,
      Gln, Asp or Glu

<400> SEQUENCE: 51

Gly Asp Ser Xaa Arg Pro Ser
1               5

<210> SEQ ID NO 52
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Gly, Leu, Ile, Ala, Phe, Met, Trp, Val,
      Pro, Ser, Thr, Cys, His, Tyr, Asn, or Gln

<400> SEQUENCE: 52

Xaa Ser Tyr Ala Gly Ser Gly Ile Tyr Val
1               5                   10

<210> SEQ ID NO 53
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Gly, Leu, Ile, Ala, Phe, Met, Trp, Val,
      or Pro

<400> SEQUENCE: 53

Ser Ser Tyr Xaa Gly Ser Gly Ile Tyr Val
1               5                   10

<210> SEQ ID NO 54
<211> LENGTH: 7
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Gly, Leu, Ile, Ala, Phe, Met, Trp, Val,
      Pro, His, Lys, or Arg

<400> SEQUENCE: 54

Leu Ala Xaa Gly Asp Ser Tyr
1               5
```

```
<210> SEQ ID NO 55
<211> LENGTH: 7
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Gly, Ser, Asp, Gln, or His

<400> SEQUENCE: 55

Leu Ala Ile Xaa Asp Ser Tyr
1               5

<210> SEQ ID NO 56
<211> LENGTH: 3
<212> TYPE: PRT
<213> ORGANISM: Homo sapiens

<400> SEQUENCE: 56

Lys Ser Gly
1

<210> SEQ ID NO 57
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Gly, Leu, Ile, Ala, Phe, Met, Trp, Val,
      or Pro

<400> SEQUENCE: 57

Val Gly Xaa Tyr Asn Xaa
1               5

<210> SEQ ID NO 58
<211> LENGTH: 4
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Ser, Thr, Cys, His, Met, Tyr, Trp, Asn,
      or Gln
<220> FEATURE:
<221> NAME/KEY: MISC_FEATURE
<222> LOCATION: (4)..(4)
<223> OTHER INFORMATION: Xaa is Ser, Thr, Cys, His, Met, Tyr, Trp, Asn,
      Gln, Asp or Glu

<400> SEQUENCE: 58

Gly Asp Xaa Xaa
1

<210> SEQ ID NO 59
<211> LENGTH: 7
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Gly, Leu, Ile, Ala, Phe, Met, Trp, Val,
      or Pro
```

-continued

```
<400> SEQUENCE: 59

Tyr Xaa Gly Ser Gly Ile Tyr
1               5

<210> SEQ ID NO 60
<211> LENGTH: 3
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ser, Thr, Cys, His, Met, Tyr, Trp, Asn,
      Gln, Asp or Glu

<400> SEQUENCE: 60

Xaa Tyr Ala
1

<210> SEQ ID NO 61
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Ser or Thr
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Gly, Leu, Ile, Ala, Phe, Met, Trp, Val,
      Pro, Ser, Thr, Cys, His, Tyr, Asn, or Gln
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Gly, Leu, Ile, Ala, Phe, Met, Trp, Val,
      Pro, His, Lys, or Arg
<220> FEATURE:
<221> NAME/KEY: MISC_FEATURE
<222> LOCATION: (9)..(9)
<223> OTHER INFORMATION: Xaa is any amino acid

<400> SEQUENCE: 61

Xaa Ile Xaa Xaa Ser Xaa Xaa Gln Xaa Arg
1               5                   10

<210> SEQ ID NO 62
<211> LENGTH: 3
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Gly, Leu, Ile, Ala, Phe, Met, Trp, Val,
      Pro, His, Lys, or Arg

<400> SEQUENCE: 62

Leu Ala Xaa
1
```

What is claimed is:

1. A method of treating lupus in a pregnant subject, wherein the method comprises administering an antibody to the pregnant subject, wherein the antibody comprises: (1) a light chain variable region comprising a CDR L1, a CDR L2, and a CDR L3 and (2) a heavy chain variable region comprising a CDR H1, a CDR H2, and a CDR H3, wherein the CDR L1 comprises a sequence X$_1$GTGSDVGSYNX$_2$VS (SEQ ID NO: 12), the CDR L2 comprises a sequence GDX$_3$X$_4$RPS (SEQ ID NO: 13), the CDR L3 comprises a sequence X$_5$SYX$_6$GSGIYV (SEQ ID NO: 14), the CDR H1 comprises a sequence Z$_1$YAMG (SEQ ID NO: 15), the CDR H2 comprises a sequence Z$_7$IGZ$_2$SGZ$_3$QTZ$_4$YADS (SEQ ID NO: 16), and the CDR H3 comprises a sequence LAZ$_5$Z$_6$DSY (SEQ ID NO: 17), wherein X$_1$ is a polar or hydrophobic amino acid, X$_2$ is a hydrophobic amino acid, X$_3$ is a polar amino acid, X$_4$ is a polar or acidic amino acid, X$_5$ is a polar or hydrophobic amino acid, X$_6$ is a hydrophobic amino acid, Z is a polar or acidic amino acid, Z$_2$ is a polar or hydrophobic amino acid, Z$_3$ is G, S, or A, Z$_4$ is a basic amino acid, Z$_5$ is a hydrophobic or basic amino acid, Z$_6$ is G, S, D, Q, or H, and Z$_7$ is S or T, and wherein administering the antibody treats lupus in the pregnant subject.

2. The method of claim 1, wherein the antibody comprises: (1) a light chain variable region comprising a CDR L1, a CDR L2, and a CDR L3 and (2) a heavy chain variable region comprising a CDR H1, a CDR H2, and a CDR H3, wherein the CDR L1 comprises the sequence XIGTGSDVGSYN-LVS (SEQ ID NO: 48) or TGTGSDVGSYNX$_2$VS (SEQ ID NO: 49), the CDR L2 comprises the sequence GDX$_3$ERPS (SEQ ID NO: 50) or GDSX$_4$RPS (SEQ ID NO: 51), the CDR L3 comprises the sequence XsSYAGSGIYV (SEQ ID NO: 52) or SSYX$_6$GSGIYV (SEQ ID NO: 53), the CDR H1 comprises the sequence of TYAMG (SEQ ID NO: 4), DYAMG (SEQ ID NO: 5), or NYAMG (SEQ ID NO: 6), the CDR H2 comprises the sequence of SIGASGSQTRY-ADS (SEQ ID NO: 8), SIGSSGAQTRYADS (SEQ ID NO: 7), SIGASGAQTRYADS (SEQ ID NO: 9), SIGASGGQTRYADS (SEQ ID NO: 10), TIGSSGAQTRYADS (SEQ ID NO: 41), SIGASGSQTRYADS (SEQ ID NO: 42), TIGASGAQTRYADS (SEQ ID NO: 43), or TIGASGGQTRYADS (SEQ ID NO: 46), and the CDR H3 comprises the sequence LAZ$_5$GDSY (SEQ ID NO: 54) or LAIZ$_6$DSY (SEQ ID NO: 55).

3. The method of claim 2, wherein the antibody comprises (1) a light chain variable region comprising a CDR L1, a CDR L2, and a CDR L3 and (2) a heavy chain variable region comprising a CDR H1, a CDR H2, and a CDR H3, wherein the CDR L1 comprises the sequence TGTGSDVGSYN-LVS (SEQ ID NO: 1);

the CDR L2 comprises the sequence GDSERPS (SEQ ID NO: 2);

the CDR L3 comprises the sequence SSYAGSGIYV (SEQ ID NO: 3);

the CDR H1 comprises the sequence TYAMG (SEQ ID NO: 4);

the CDR H2 comprises the sequence SIGSSGAQTRY-ADS (SEQ ID NO: 7), or TIGSSGAQTRYADS (SEQ ID NO: 41); and the CDR H3 comprises the sequence LAIGDSY (SEQ ID NO: 11).

4. The method of claim 1, wherein the method reduces IgG autoantibodies in the pregnant subject.

5. The method of claim 1, wherein the light chain comprises an amino acid sequence having at least 90% identity to the sequence:

```
                                      (SEQ ID NO: 19)
QSALTQPASVSGSPGQSITISCTGTGSDVGSYNLV

SWYQQHPGKAPKLMIYGDSERPSGVSNRFSGSKSG

NTASLTISGLQAEDEADYYCSSYAGSGIYVFGTGT

KVTVLGQPKAAPSVTLFPPSSEELQANKATLVCLI

SDFYPGAVTVAWKADSSPVKAGVETTTPSKQSNNK

YAASSYLSLTPEQWKSHKSYSCQVTHEGSTVEKTV

APTECS.
```

6. The method of claim 1, wherein the heavy chain comprises an amino acid sequence selected from the group consisting of:

a sequence having at least 90% identity to the sequence of

```
                                      (SEQ ID NO: 20)
EVQLLESGGGLVQPGGSLRLSCAASGFTFSTYAMG

WVRQAPGKGLEWVSSIGSSGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG;
``` a sequence having at least 90% identity to the sequence of

```
                                      (SEQ ID NO: 21)
EVQLLESGGGLVQPGGSLRLSCAASGFTFSDYAMG

WVRQAPGKGLEWVSSIGASGSQTRYADSVKGRFTI

SRDNSKNTLYLQMNSLRAEDTAVYYCARLAIGDSY
```

-continued

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSRDELTKNQVSLTCLVKGFYPSDIAVEWESNGQ

PENNYKTTPPVLDSDGSFFLYSKLTVDKSRWQQGN

VFSCSVMHEALHNHYTQKSLSLSPG;

a sequence having at least 90% identity to the sequence of (SEQ ID NO: 22)

EVQLLESGGGLVQPGGSLRLSCAASGFTFSNYAMG

WVRQAPGKGLEWVSSIGASGAQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG;

a sequence having at least 90% identity to the sequence of (SEQ ID NO: 23)

EVQLLESGGGLVQPGGSLRLSCAASGFTFSTYAMGWVRQAPGKGLEWVS

SIGASGGQTRYADSVKGRFTISRDNSKNTLYLQMNSLRAEDTAVYYCAR

LAIGDSYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YASTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLS

LSPG;

and a sequence having at least 90% identity to the sequence of (SEQ ID NO: 24)

EVQLLESGGGLVQPGGSLRLSCAASGFTFSTYAMG

WVRQAPGKGLEWVSSIGASGSQTRYADSVKGRFTI

SRDNSKNTLYLQMNSLRAEDTAVYYCARLAIGDSY

WGQGTMVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKKVEPKSCDKTHTCPPCPAPELLGGPSVFLFPPK

PKDTLMISRTPEVTCVVVDVSHEDPEVKFNWYVDG

VEVHNAKTKPREEQYASTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPG.

7. The method of claim 1, wherein the isolated antibody comprises:

(1) a light chain variable region comprising a CDR L1, a CDR L2, and a CDR L3 and (2) a heavy chain variable region comprising a CDR H1, a CDR H2, and a CDR H3, wherein:

the CDR L1 comprises a sequence having no more than two amino acid substitutions relative to the sequence of TGTGSDVGSYNLVS (SEQ ID NO: 1);

the CDR L2 comprises a sequence having no more than one amino acid substitution relative to the sequence of GDSERPS (SEQ ID NO: 2);

the CDR L3 comprises a sequence having no more than one amino acid substitution relative to the sequence of SSYAGSGIYV (SEQ ID NO: 3);

the CDR H1 comprises a sequence having no more than one amino acid substitution relative to the sequence of TYAMG (SEQ ID NO: 4), DYAMG (SEQ ID NO: 5), or NYAMG (SEQ ID NO: 6);

the CDR H2 comprises a sequence having no more than two amino acid substitutions relative to the sequence of SIGASGSQTRYADS (SEQ ID NO: 8), SIGSSGAQTRYADS (SEQ ID NO: 7), SIGASGAQTRYADS (SEQ ID NO: 9), SIGASGGQTRYADS (SEQ ID NO: 10), TIGSSGAQTRYADS (SEQ ID NO: 41), SIGASGSQTRYADS (SEQ ID NO: 42), TIGASGAQTRYADS (SEQ ID NO: 43), or TIGASGGQTRYADS (SEQ ID NO: 32); and the CDR H3 comprises a sequence having no more than one amino acid substitution relative to the sequence of LAIGDSY (SEQ ID NO: 11).

8. The method of claim 1, wherein:

the CDR L1 of the isolated antibody comprises the sequence TGTGSDVGSYNLVS (SEQ ID NO: 1);

the CDR L2 of the isolated antibody comprises the sequence GDSERPS (SEQ ID NO: 2);

the CDR L3 of the isolated antibody comprises the sequence SSYAGSGIYV (SEQ ID NO: 3);

the CDR H1 of the isolated antibody comprises the sequence DYAMG (SEQ ID NO: 5);

the CDR H2 of the isolated antibody comprises the sequence SIGASGSQTRYADS (SEQ ID NO: 8); and the CDR H3 of the isolated antibody comprises the sequence LAIGDSY (SEQ ID NO: 11).

9. The method of claim 1, wherein:

the CDR L1 of the isolated antibody comprises the sequence TGTGSDVGSYNLVS (SEQ ID NO: 1);

the CDR L2 of the isolated antibody comprises the sequence GDSERPS (SEQ ID NO: 2);

the CDR L3 of the isolated antibody comprises the sequence SSYAGSGIYV (SEQ ID NO: 3);

the CDR H1 of the isolated antibody comprises the sequence NYAMG (SEQ ID NO: 6);

the CDR H2 of the isolated antibody comprises the sequence SIGASGAQTRYADS (SEQ ID NO: 9) or TIGASGAQTRYADS (SEQ ID NO: 43); and the CDR H3 of the isolated antibody comprises the sequence LAIGDSY (SEQ ID NO: 11).

10. The method of claim 1, wherein:

the CDR L1 of the isolated antibody comprises the sequence TGTGSDVGSYNLVS (SEQ ID NO: 1);

the CDR L2 of the isolated antibody comprises the sequence GDSERPS (SEQ ID NO: 2);

the CDR L3 of the isolated antibody comprises the sequence SSYAGSGIYV (SEQ ID NO: 3);

the CDR H1 of the isolated antibody comprises the sequence TYAMG (SEQ ID NO: 4);

the CDR H2 of the isolated antibody comprises the sequence SIGASGGQTRYADS (SEQ ID NO: 10) or TIGASGGQTRYADS (SEQ ID NO: 32); and the CDR H3 of the isolated antibody comprises the sequence LAIGDSY (SEQ ID NO: 11).

11. The method of claim 1, wherein:

the CDR L1 of the isolated antibody comprises the sequence TGTGSDVGSYNLVS (SEQ ID NO: 1);

the CDR L2 of the isolated antibody comprises the sequence GDSERPS (SEQ ID NO: 2);

the CDR L3 of the isolated antibody comprises the sequence SSYAGSGIYV (SEQ ID NO: 3);

the CDR H1 of the isolated antibody comprises the sequence TYAMG (SEQ ID NO: 4);

the CDR H2 of the isolated antibody comprises the sequence SIGASGSQTRYADS (SEQ ID NO: 8); and the CDR H3 of the isolated antibody comprises the sequence LAIGDSY (SEQ ID NO: 11).

12. The method of claim 1, wherein the heavy chain of the isolated antibody comprises a sequence of SEQ ID NO: 19 and the light chain of the isolated antibody comprises a sequence of SEQ ID NO: 24.

13. The method of claim 1, wherein the heavy chain of the isolated antibody comprises a sequence having at least 95%, 97%, 99%, or 100% identity to the sequence of any one of SEQ ID NOs: 20-24.

14. The method of claim 1, wherein the light chain of the isolated antibody comprises a sequence having at least 95%, 97%, 99%, or 100% identity to the sequence of SEQ ID NO: 19.

\* \* \* \* \*